(12) United States Patent
Eberle et al.

(10) Patent No.: US 7,612,064 B2
(45) Date of Patent: Nov. 3, 2009

(54) SULFOPYRROLES

(75) Inventors: Martin Eberle, Bottmingen (CH); Philipp Ermert, Allschwil (CH); Daniel Obrecht, Battwil (CH); Frank Lach, Mulhouse (FR); Anatol Luther, Grenzach-Wyhlen (DE); Felix Bachmann, Basel (CH); Allessandro Strebel, Oberwil (CH)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/557,664

(22) PCT Filed: May 24, 2004

(86) PCT No.: PCT/IB2004/001818

§ 371 (c)(1),
(2), (4) Date: Nov. 22, 2005

(87) PCT Pub. No.: WO2004/103968

PCT Pub. Date: Dec. 2, 2004

(65) Prior Publication Data

US 2007/0060570 A1    Mar. 15, 2007

(30) Foreign Application Priority Data

May 26, 2003  (EP) ................................ 03405380

(51) Int. Cl.
*C07D 233/00* (2006.01)
*C07D 249/08* (2006.01)
*C07D 413/00* (2006.01)
*A61K 31/535* (2006.01)
*A01N 43/50* (2006.01)
*A01N 43/64* (2006.01)

(52) U.S. Cl. .................. 514/231.5; 514/397; 514/383; 548/311.1; 548/266.2; 544/141

(58) Field of Classification Search ................ None
See application file for complete search history.

(56) References Cited

FOREIGN PATENT DOCUMENTS

WO    WO00/69847    * 11/2000

OTHER PUBLICATIONS

Sun et al., CAPLUS AN 2004:570508, priority date Oct. 11, 2002, (2pages).*
Kazuaki Okabe et al., "The Second Generation Synthesis of a Tumor Promoter Pendolmycin," Tetrahedron, vol. 47, No. 36, Jul. 1, 1997, pp. 7615-7624, XP001155513.

* cited by examiner

*Primary Examiner*—Golam M. M. Shameem
*Assistant Examiner*—Sun Jae Y Loewe
(74) *Attorney, Agent, or Firm*—Hamre, Schumann, Mueller & Larson, P.C.

(57) ABSTRACT

The invention relates to compounds of formula (I) wherein $R^1$ represents aryl, aralkyl or heteroaryl, $R^2$ is aryl or heteroaryl and $R^3$ is aryl, heteroaryl or optionally substituted aminomethyl, to methods of synthesis of such compounds, to pharmaceutical compositions containing compounds of formula (I), to the use of a compounds of formula (I) for the preparation of a pharmaceutical composition for the treatment of neoplastic and autoimmune diseases, and to methods of treatment of neoplastic and autoimmune diseases using compounds of formula (I) or of pharmaceutical compositions containing same.

9 Claims, No Drawings

SULFOPYRROLES

The invention relates to novel substituted sulfopyrroles, processes for the preparation thereof, pharmaceutical compositions containing same, the use thereof optionally in combination with one or more other pharmaceutically active compounds for the therapy of neoplastic diseases and autoimmune diseases, and a method for the treatment of such a diseases.

BACKGROUND OF THE INVENTION

Cancer is one of the leading causes of death in humans. Although a variety of drugs against neoplastic diseases have been developed and techniques are available such as surgery and radiation therapy, there is still a need for alternative and improved methods of treatment of neoplastic diseases.

Autoimmune diseases are associated with abnormal lymphoproliferation as a result of defects in the termination of lymphocyte activation and growth. Often, such diseases are associated with inflammation like rheumatoid arthritis, insulin dependent diabetes mellitus, multiple sclerosis, systemic lupus erythematosus and the like. The treatment of such diseases is focused on anti-inflammatory and immunosuppressive drugs which in numerous cases show severe side effects. Hence, there is a need for alternative drugs with a new mode of action showing less side effects.

Apoptosis is a term used to describe a series of cellular events which occur to bring about programmed cell death. There are various apoptotic pathways, some of which have been characterized, whereas others remain to be elucidated. If the balance between cell division and apoptosis is disturbed, life-threatening diseases including cancer, autoimmune disorders, neurodegenerative and cardiovascular diseases may occur.

In recent years it has become evident that programmed cell death (apoptosis) is as important to the health of a multicellular organism as cell division. By repeated cell division and differentiation throughout development or tissue repair, surplus or even harmful cells are generated. In order to maintain tissue homeostasis these cells have to be removed or killed. The delicate interplay between cell growth and apoptosis in an organism is mirrored in the complex molecular balance that determines whether an individual cell undergoes division, arrests in the cell cycle or commits to programmed cell death.

Dysregulation of cell proliferation, or lack of appropriate cell death, has wide ranging clinical implications. A number of diseases associated with such dysregulation involve hyperproliferation, inflammation, tissue remodeling and repair. Familiar indications in this category include cancers, restenosis, neointimal hyperplasia, angiogenesis, endometriosis, lymphoproliferative disorders, transplantation related pathologies (graft rejection), polyposis, loss of neural function in the case of tissue remodeling and the like. Such cells may lose the normal regulatory control of cell division, and may also fail to undergo appropriate cell death.

As apoptosis is inhibited or delayed in most types of proliferative, neoplastic diseases, induction of apoptosis is an option for treatment of cancer, especially in cancer types which show resistance to classic chemotherapy, radiation and immunotherapy (Apoptosis and Cancer Chemotherapy, Hickman and Dive, eds., Blackwell Publishing, 1999). Also in autoimmune and transplantation related diseases and pathologies compounds inducing apoptosis may be used to restore normal cell death processes and therefore can eradicate the symptoms and might cure the diseases. Further applications of compounds inducing apoptosis may be in restenosis, i.e. accumulation of vascular smooth muscle cells in the walls of arteries, and in persistent infections caused by a failure to eradicate bacteria- and virus-infected cells. Furthermore, apoptosis can be induced or re-established in epithelial cells, in endothelial cells, in muscle cells, and in others which have lost contact with extracellular matrix. These cells are potentially able to colonize other organs and therefore can develop into pathologies like neoplasias, endometriosis and the like.

SUMMARY OF THE INVENTION

Sulfopyrroles of formula (I) are selectively inducing apoptosis in cancer cells, and can be used for the treatment of neoplastic and autoimmune diseases. The invention relates to novel compounds of formula (I) as defined hereinafter, to methods of synthesis of such compounds, to compounds of formula (I) for use as medicaments, to pharmaceutical compositions containing compounds of formula (I), to the use of a compounds of formula (I) for the preparation of a pharmaceutical composition for the treatment of neoplastic and autoimmune diseases, and to methods of treatment of neoplastic and autoimmune diseases using such compounds of formula (I) or of pharmaceutical compositions containing same.

DETAILED DESCRIPTION OF THE INVENTION

The invention relates to compounds of formula (I)

(I)

wherein $R^1$ represents aryl, aralkyl, arylalkenyl or heteroaryl, wherein aryl, aryl in aralkyl and arylalkenyl and heteroaryl may be substituted by one to five substituents independently selected from lower alkyl, cycloalkyl, halo-lower alkyl, lower alkoxy-lower alkyl, lower alkenyl, lower alkinyl, optionally substituted phenyl, heteroaryl, heterocyclyl, lower alkoxy, lower alkoxy-lower alkoxy, lower alkenyloxy, lower alkinyloxy, optionally substituted phenoxy, dialkylamino, lower alkylsulfonyl, halo-lower alkylsulfonyl, halo-lower alkylsulfinyl, halogen, cyano and nitro; and wherein two adjacent substituents together with the atoms of aryl or heteroaryl may form a 5, 6 or 7 membered carbocyclic or heterocyclic ring;

$R^2$ is aryl or heteroaryl wherein aryl or heteroaryl may be substituted by one to five substituents independently chosen from lower alkyl, halo-lower alkyl, cycloalkyl, cycloalkyl-lower alkyl, hydroxy-lower alkyl, lower alkoxy-lower alkyl, lower alkoxy-lower alkoxy-lower alkyl, halo-lower alkoxy-lower alkyl, heterocyclyl, heterocyclyl-lower alkyl, optionally substituted phenyl, optionally substituted phenyl-lower alkyl, optionally substituted heteroaryl, optionally substituted heteroaryl-lower alkyl, optionally substituted alkenyl, optionally substituted alkinyl, hydroxy, lower alkoxy, optionally substituted alkenyloxy, optionally substituted alkinyloxy, halo-lower alkoxy, cycloalkoxy, cycloalkyl-lower alkoxy, hydroxy-lower alkoxy, lower alkoxy-lower alkoxy, heterocyclyloxy, heterocyclyl-lower alkoxy, optionally substituted phenyloxy, optionally substituted phenyl-lower alkoxy, optionally substituted heteroaryloxy, optionally substituted heteroaryl-lower alkoxy, sulfamoyloxy, carbamoyloxy, lower alkylcarbonyloxy, amino, carbamoyl, sulfamoyl, amino-lower alkyl or amino-lower alkylamino, wherein in each case the nitrogen atom is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl and lower alkylcarbonyl, or wherein the two substituents on nitrogen form together with the nitrogen heteroaryl or heterocyclyl;

lower alkylcarbonyl, cycloalkylcarbonyl, optionally substituted phenylcarbonyl, optionally substituted heteroarylcarbonyl, heterocyclylcarbonyl, carboxy, lower alkoxycarbonyl, hydroxy-lower alkoxycarbonyl, lower alkoxy-lower alkoxycarbonyl, optionally substituted phenyl-lower alkoxycarbonyl, cyano, mercapto, lower alkylmercapto, optionally substituted phenylmercapto, lower alkylsulfinyl, halo-lower alkylsulfinyl, optionally substituted phenylsulfinyl, lower alkylsulfonyl, halo-lower alkylsulfonyl, optionally substituted phenylsulfonyl, optionally substituted phenyl-lower alkylsulfonyl, halogen, and cyano;

and wherein two adjacent substituents together with the atoms of aryl or heteroaryl may form a 5, 6 or 7 membered carbocyclic or heterocyclic ring;

$R^3$ represents unsubstituted aryl;

aryl substituted by one substituent selected from formyl, lower alkylcarbonyl, hydroxy-lower alkylcarbonyl, alkoxy-lower alkylcarbonyl, amino-lower alkylcarbonyl, carboxy, lower alkoxycarbonyl, hydroxy-lower alkoxycarbonyl, lower alkoxy-lower alkoxycarbonyl, optionally substituted phenyl-lower alkoxycarbonyl, heteroaryl, heterocycyl, a carbamoyl group $CONR^4R^5$, and a sulfamoyl group $SO_2NR^4R^5$, wherein such substituents on aryl may be directly linked or linked via a spacer selected from lower alkylidene, oxygen, oxymethyl, nitrogen optionally substituted by lower alkyl, or aminomethyl wherein the amino nitrogen is optionally substituted by lower alkyl; and optionally one or two further substituents selected from lower alkyl, halo-lower alkyl, lower alkoxy-lower alkyl, lower alkoxy, lower alkoxy-lower alkoxy, halo and nitro;

aryl substituted by one substituent selected from amino optionally substituted by one or two substituents selected from lower alkyl, hydroxyalkyl, alkoxyalkyl, aminoalkyl and optionally substituted alkylcarbonyl, and an aminocarbonylamino group $NHCONR^4R^5$, wherein such substituents on aryl may be directly linked or linked via a lower alkylidene spacer; and optionally one or two further substituents selected from lower alkyl, halo-lower alkyl, lower alkoxy-lower alkyl, lower alkoxy, lower alkoxy-lower alkoxy, halo and nitro;

aryl substituted by one substituent selected from cyano, cyanomethyl, sulfo, lower alkoxysulfonyl, hydroxy-lower alkoxysulfonyl, lower alkoxy-lower alkoxysulfonyl and optionally substituted phenyl-lower alkoxysulfonyl; and optionally one or two further substituents selected from lower alkyl, halo-lower alkyl, lower alkoxy-lower alkyl, lower alkoxy, lower alkoxy-lower alkoxy, halo and nitro;

heteroaryl, optionally substituted by one or two substituents selected from lower alkyl, halo-lower alkyl, lower alkoxy-lower alkyl, lower alkoxy, lower alkoxy-lower alkoxy, carboxy, lower alkoxycarbonyl, a carbamoyl group $CONR^4R^5$, a sulfamoyl group $SO_2NR^4R^5$, amino optionally substituted by one or two substituents selected from lower alkyl, hydroxyalkyl, alkoxyalkyl, aminoalkyl and optionally substituted alkylcarbonyl, an aminocarbonylamino group $NHCONR^4R^5$, cyano, and halo; and wherein substituents carboxy, lower alkoxycarbonyl, carbamoyl or sulfamoyl may be directly linked or linked via a spacer selected from lower alkylidene, oxygen, oxymethyl, nitrogen optionally substituted by lower alkyl, and aminomethyl wherein the amino nitrogen is optionally substituted by lower alkyl, alkylcarbonyl, alkoxycarbonyl or aminocarbonyl; and wherein substituents amino and aminocarbonylamino may be directly linked or linked via a lower alkylidene spacer;

or a group $CH_2NR^6R^7$;

$R^4$ represents hydrogen, alkyl, cycloalkyl, cycloalkylalkyl, hydroxyalkyl, alkoxyalkyl, hydroxyalkoxyalkyl, alkoxyalkoxyalkyl, optionally substituted alkenyl, optionally substituted alkinyl, aminoalkyl, wherein the nitrogen can be substituted by up to two substituents selected from lower alkyl, cycloalkyl, cycloalkyl-lower alkyl, hydroxy-lower alkyl, lower alkoxy-lower alkyl, hydroxy-lower alkoxy-lower alkyl or lower alkoxy-lower alkoxy-lower alkyl; optionally substituted phenyl, optionally substituted phenyl-lower alkyl, optionally substituted heteroaryl, optionally substituted heteroaryl-lower alkyl, heterocyclyl, optionally substituted alkenyl, optionally substituted alkinyl, lower alkylcarbonyl, cycloalkylcarbonyl, optionally substituted phenylcarbonyl, lower alkylsulfonyl, or optionally substituted phenylsulfonyl;

$R^5$ represents hydrogen or lower alkyl;

or $R^4$ and $R^5$ together with the nitrogen they are bound to represent a five, six or seven membered heterocyclic ring that can be partially or fully unsaturated and may be optionally substituted by one or more substituents selected from oxo, lower alkyl, halo-lower alkyl, hydroxy-lower alkyl, lower alkoxy-lower alkyl or lower alkoxy;

$R^6$ represents hydrogen, alkyl, cycloalkyl, cycloalkylalkyl, hydroxyalkyl, alkoxyalkyl, hydroxyalkoxyalkyl, alkoxyalkoxyalkyl, optionally substituted phenyl-lower alkyl, optionally substituted heteroaryl-lower alkyl, heterocyclyl, optionally substituted alkenyl, optionally substituted alkinyl, aminoalkyl or aminoalkylcarbonyl, wherein the nitrogen can be substituted by up to two substituents selected from lower alkyl, cycloalkyl, cycloalkyl-lower alkyl, hydroxy-lower alkyl, lower alkoxy-lower alkyl, hydroxy-lower alkoxy-lower alkyl and lower alkoxy-lower alkoxy-lower alkyl; optionally substituted alkenyl, optionally substituted alkinyl, lower alkylcarbonyl, cycloalkylcarbonyl, optionally substituted phenylcarbonyl, lower alkylsulfonyl, or optionally substituted phenylsulfonyl;

unsubstituted aryl;

aryl substituted by one substituent selected from formyl, lower alkylcarbonyl; hydroxy-lower alkylcarbonyl, alkoxy-lower alkylcarbonyl, amino-lower alkylcarbonyl, carboxy, lower alkoxycarbonyl, hydroxy-lower alkoxycarbonyl, lower alkoxy-lower alkoxycarbonyl, optionally substituted phenyl-lower alkoxycarbonyl, heteroaryl, heterocycyl, a carbamoyl group $CONR^4R^5$, and a sulfamoyl group $SO_2NR^4R^5$, wherein such substituents on aryl may be directly linked or linked via a spacer selected from lower alkylidene, oxygen, oxymethyl, nitrogen optionally substituted by lower alkyl, or aminomethyl wherein the amino nitrogen is optionally substituted by lower alkyl; and optionally one or two further substituents selected from lower alkyl, halo-lower alkyl, lower alkoxy-lower alkyl, lower alkoxy, lower alkoxy-lower alkoxy, halo and nitro;

aryl substituted by one substituent selected from amino optionally substituted by one or two substituents selected from lower alkyl, hydroxyalkyl, alkoxyalkyl, aminoalkyl and optionally substituted alkylcarbonyl, and an aminocarbonylamino group $NHCONR^4R^5$, wherein such substituents on aryl may be directly linked or linked via a lower alkylidene spacer; and optionally one or two further substituents selected from lower alkyl, halo-lower alkyl, lower alkoxy-lower alkyl, lower alkoxy, lower alkoxy-lower alkoxy, halo and nitro;

aryl substituted by one substituent selected from cyano, cyanomethyl, sulfo, lower alkoxysulfonyl, hydroxy-lower alkoxysulfonyl, lower alkoxy-lower alkoxysulfonyl and optionally substituted phenyl-lower alkoxysulfonyl; and optionally one or two further substituents selected from lower alkyl, halo-lower alkyl, lower alkoxy-lower alkyl, lower alkoxy, lower alkoxy-lower alkoxy, halo and nitro; or heteroaryl, optionally substituted by one or two substituents selected from lower alkyl, halo-lower alkyl, lower alkoxy-lower alkyl, lower alkoxy, lower alkoxy-lower alkoxy, carboxy, lower alkoxycarbonyl, a carbamoyl group $CONR^4R^5$, a sulfamoyl group $SO_2NR^4R^5$, amino optionally substituted by one or two substituents selected from lower alkyl, hydroxyalkyl, alkoxyalkyl, aminoalkyl and optionally substituted alkylcarbonyl, an aminocarbonylamino group $NHCONR^4R^5$, cyano, and halo; and wherein substituents carboxy, lower alkoxycarbonyl, carbamoyl or sulfamoyl may be directly linked or linked via a spacer selected from lower alkylidene, oxygen, oxymethyl, nitrogen optionally substituted by lower alkyl, and aminomethyl wherein the amino nitrogen is optionally substituted by lower alkyl, alkylcarbonyl, alkoxycarbonyl or aminocarbonyl; and wherein substituents amino and aminocarbonylamino may be directly linked or linked via a lower alkylidene spacer;

$R^7$ represents hydrogen, lower alkyl, lower alkylcarbonyl, lower alkoxycarbonyl or lower alkoxysulfonyl;

or $R^6$ and $R^7$ together with the nitrogen they are bound to represent a five, six or seven membered heterocyclic ring that can be partially or fully unsaturated and may be optionally substituted by one or more groups selected from oxo, lower alkyl, halo-lower alkyl, hydroxy-lower alkyl, lower alkoxy-lower alkyl or lower alkoxy;

and salts thereof.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Double bonds in principle can have E- or Z-configuration. The compounds of this invention may therefore exist as isomeric mixtures or single isomers. If not specified both isomeric forms are intended.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention relates also to possible tautomers of the compounds of formula (I).

Alkyl has from 1 to 12, preferably from 1 to 7 carbon atoms, and is linear or branched. Alkyl is preferably lower alkyl.

Lower alkyl has 1 to 4 carbon atoms and is butyl, such as n-butyl, sec-butyl, isobutyl, tert-butyl, propyl, such as n-propyl or isopropyl, ethyl or methyl. Preferably lower alkyl is methyl or ethyl.

Cycloalkyl has preferably 3 to 7 ring carbon atoms, and may be unsubstituted or substituted, e.g. by lower alkyl or lower alkoxy. Cycloalkyl is, for example, cyclohexyl, cyclopentyl, or methylcyclopentyl.

Aryl stands for a mono- or bicyclic fused ring aromatic group with 5 to 10 carbon atoms, such as phenyl, 1-naphthyl or 2-naphthyl, or also a partially saturated bicyclic fused ring comprising a phenyl group, such as indanyl, dihydro- or tetrahydronaphthyl.

In optionally substituted phenyl, substituents are preferably lower alkyl, lower alkoxy, lower alkoxy-lower alkoxy, methylenedioxy, halo-lower alkyl, lower alkoxy-lower alkyl, halo, or nitro.

Heteroaryl represents an aromatic group containing at least one heteroatom selected from nitrogen, oxygen and sulfur, and is mono- or bicyclic. Monocyclic heteroaryl includes 5 or 6 membered heteroaryl groups containing 1, 2, 3 or 4 heteroatoms selected from nitrogen, sulfur and oxygen. Bicyclic heteroaryl includes 9 or 10 membered fused-ring heteroaryl groups. Examples of heteroaryl include pyrrolyl, thienyl, furyl, pyrazolyl, imidazolyl, triazolyl, oxazolyl, isoxazolyl, oxadiazolyl, thiazolyl, isothiazolyl, thiadiazolyl, pyridyl, pyridazinyl, pyrimidinyl, pyrazinyl, and benzo fused derivatives of such monocyclic heteroaryl groups, such as indolyl, benzimidazolyl or benzofuryl, quinolinyl, isoquinolinyl, quinazolinyl, quinoxalinyl or purinyl.

In optionally substituted heteroaryl, substituents are preferably lower alkyl, halo-lower alkyl, lower alkoxy-lower alkyl, lower alkoxy, lower alkoxy-lower alkoxy, amino optionally substituted by one or two substituents lower alkyl and one substituent lower alkylcarbonyl, halo, or nitro.

Alkenyl contains one or more, e.g. two or three, double bonds, and is preferably lower alkenyl, such as 1- or 2-butenyl, 1-propenyl, allyl or vinyl. Arylalkenyl is preferably 2-aryl-vinyl.

Alkinyl is preferably lower alkinyl, such as propargyl or acetylenyl.

In optionally substituted alkenyl or alkinyl, substituents are preferably lower alkyl, lower alkoxy, halo or di(lower alkyl) amino, and are connected with a saturated carbon atom of alkenyl or alkinyl or with an unsaturated carbon atom of alkenyl.

Heterocyclyl designates preferably a saturated, partially saturated or unsaturated, mono- or bicyclic ring containing 4-10 atoms comprising one, two or three heteroatoms selected from nitrogen, oxygen and sulfur, which may, unless otherwise specified, be carbon or nitrogen linked, wherein a ring nitrogen atom may optionally be substituted by a group selected from lower alkyl, amino-lower alkyl, aryl, aryl-lower alkyl and acyl, and a ring carbon atom may be substituted by lower alkyl, amino-lower alkyl, aryl, aryl-lower alkyl, heteroaryl, lower alkoxy, hydroxy or oxo. Examples of heterocyclyl are pyrrolidinyl, oxazolidinyl, thiazolidinyl, piperidinyl, morpholinyl, piperazinyl, dioxolanyl and tetrahydropyranyl.

Acyl designates, for example, alkylcarbonyl, cyclohexylcarbonyl, arylcarbonyl, aryl-lower alkylcarbonyl, or heteroarylcarbonyl. Lower acyl is preferably lower alkylcarbonyl, in particular propionyl or acetyl. Optionally substituted alkylcarbonyl is preferably substituted by hydroxy, alkoxy or amino.

Hydroxyalkyl is especially hydroxy-lower alkyl, preferably hydroxymethyl, 2-hydroxyethyl or 2-hydroxy-2-propyl.

Haloalkyl is preferably fluoroalkyl, especially trifluoromethyl, pentafluoroethyl or 3,3,3-trifluoroethyl.

Halogen is fluorine, chlorine, bromine, or iodine.

Lower alkoxy is especially methoxy, ethoxy, isopropyloxy, or tert-butyloxy.

Arylalkyl includes aryl and alkyl as defined hereinbefore, and is e.g. benzyl, 1-phenethyl or 2-phenethyl.

Heteroarylalkyl includes heteroaryl and alkyl as defined hereinbefore, and is e.g. 2-pyridyl-methyl, 3-pyridyl-methyl, 4-pyridyl-methyl, 1- or 2-pyrrolyl-methyl, 1-imidazolyl-methyl, 2-(1-imidazolyl)-ethyl or 3-(1-imidazolyl)-propyl.

Two adjacent substituents which together with the atoms of aryl or heteroaryl may form a 5, 6 or 7 membered carbocyclic or heterocyclic ring are, for example, propylene, 1- or 2-oxopropylene, 1- or 2-oxapropylene, 1-oxapropylidene, methylenedioxy, difluoromethylenedioxy, 1- or 2-azapropylene, 1- or 2-azapropylidene, 1,2- or 1,3-diazapropylidene, 1,3-diaza-2-oxopropylene, butylene, 1- or 2-oxabutylene, ethylenedioxy, 1- or 2-azabutylene, or 1- or 2-azabutadienylidene, pentylene, 1-, 2- or 3-oxapentylene, propylenedioxy, 1-, 2- or 3-azapentylene, or such groups carrying further substituents as defined hereinbefore.

In substituted amino, the substituents are preferably those mentioned as substituents $R^4$ and $R^5$. In particular, substituted amino is alkylamino, dialkylamino, optionally substituted arylamino or optionally substituted arylalkylamino.

A spacer as defined for substituents on aryl and heteroaryl in $R^3$ and in $R^6$ connecting carbonyl, carboxy and derivatives of carboxy, heteroaryl, heterocyclyl or sulfamoyl to the aryl or heteroaryl group is lower alkylidene, e.g. a residue —$CH_2)_n$— wherein n is between 1 and 7, preferably between 1 and 4, e.g. methylene, 1,2-ethylene, or 1,3-propylene, oxygen, i.e. an ether bridge —O—, oxymethyl, i.e. an ether bridge —$OCH_2$—, nitrogen optionally substituted by lower alkyl, i.e. a secondary or tertiary amine bridge —NR— wherein R is hydrogen or lower alkyl, or aminomethyl wherein the amino nitrogen is optionally substituted by lower alkyl, i.e. a secondary or tertiary amine bridge —NR—$CH_2$— wherein R is hydrogen or lower alkyl. A spacer connecting substituents amino or aminocarbonylamino to the aryl or heteroaryl group is lower alkylidene as defined hereinbefore.

Salts are especially the pharmaceutically acceptable salts of compounds of formula (I).

Such salts are formed, for example, as acid addition salts, preferably with organic or inorganic acids, from compounds of formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantine-carboxylic acid, benzoic acid, salicylic acid, 4-aminosalicylic acid, phthalic acid, phenyl-acetic acid, mandelic acid, cinnamic acid, methane- or ethane-sulfonic acid, 2-hydroxy-ethanesulfonic acid, ethane-1,2-disulfonic acid, benzenesulfonic acid, 2-naphthalene-sulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compound of the formula (I) may be administered in the form of a pro-drug which is broken down in the human or animal body to give a compound of the formula (I). Examples of pro-drugs include in vivo hydrolysable esters and amides of a compound of the formula (I). Particular pro-drugs considered are ester and amides of naturally occurring amino acids and ester or amides of small peptides, in particular small peptides consisting of up to five, preferably two or three amino acids. Pro-drug esters are formed from the acid function of the amino acid or the C terminal of the peptide and suitable hydroxy group(s) in the compound of formula (I). Pro-drug amides are formed from the amino function of the amino acid or the N terminal of the peptide and suitable carboxy group(s) in the compound of formula (I).

The compounds of formula (I) have valuable pharmacological properties. The invention also relates to compounds of formula (I) as defined hereinbefore for use as medicaments.

The efficacy of the compounds of the invention in inducing apoptosis in tumor cells can be demonstrated as follows:

Relative fluorescent activities of suitable tumor cell lines transfected with green fluorescent protein (GFP) are measured in the presence of compounds of the invention and of standard tumor drugs, using the method described in WO 99/35493. Suitable tumor cell lines are A20.2J, a BALB/c B cell lymphoma, PB-3c, an IL-3 dependent, non tumorigenic mastocyte line isolated from the bone marrow of a DBA/2 mouse, Jurkat, a human acute T cell leukemia cell line, K562, a human chronic myelogenous leukemia cell line, HL60, a human acute promyelocytic leukemia cell line, Ramos and Raji, human B-cell lymphoma cell lines, H9 and Hut78, human T-cell lymphoma cell lines, HeLa and KB, human squamous cell carcinoma cell lines, MCF7, SK-BR-3, PC3, HBL-100, SW480, H460 and H1792, human adenocarcinoma cell lines and HT-1080, a human fibrosarcoma cell line.

Preferred standard drugs as compounds for comparisons are: a) antimetabolites such as 5-fluorouracil (ICN), gemcitabine HCl (Gemzar™, Eli Lilly), b) alkylating agents such as oxaliplatin (Eloxantin™, Sanofi-Synthélabo), dacarbazin (Detimedac™, Medac), cyclo-phosphamide (Endoxan™, Asta) and carboplatin (Paraplatin™, Bristol-Meyers Squibb), c) cell-cycle inhibitor such as vinorelbine (Navelbine™, Robapharm), vinblastine (Velbe™, Eli Lilly), docetaxel (Taxotere™, Aventis), d) DNA breaker (topo-isomerase inhibitor, intercalator; strand breaker) such as doxorubicin HCl (Adriblastin™, Pharmacia-Upjohn), bleomycin (Asta-Medica), irinotecan (Campto™, Aventis), etoposide phosphate (Etopophos™, Bristol-Meyers Squibb), topotecan HCl, (Hycamtin™, GlaxoSmithKline), e) mixtures thereof, f) compounds interfering with the signal transduction pathway, such as caspase activity modifiers, agonists and antagonists of cell death receptors, modifiers of nucleases, phosphatases and kinases such as imatinib mesylate (Gleevec™, Novartis), dexamethasone, phorbol myristate acetate, cyclosporin A, quercetin, tamoxifen (Alexis Corporation, Switzerland).

Apoptosis is determined in a primary screen using a fluorescence plate reader and then in a secondary screen using FACS (fluorescence activated cell scanning). Compounds causing apoptosis without substantial cytotoxic side effects are chosen for further testing and characterization by using a combination of the following well established assays: A) Nuclear staining with Hoechst 33342 dye providing information about nuclear morphology and DNA fragmentation which are hallmarks of apoptosis. B) MTS proliferation assay measuring the metabolic activity of cells. Viable cells are metabolically active whereas cells with compromised respiratory chain show a reduced activity in this test. C) AnnexinV binding assay which reflects the phosphatidylserine content of the outer lipid bilayer of the plasma membrane. This event is considered an early hallmark of apoptosis. D) PI staining for cell cycle distribution which shows any alterations in the distribution among the different phases of the cell cycle. Cell cycle arresting points can be determined. E) Proliferation assay monitoring DNA synthesis by incorporating bromodeoxyuridine (BrdU). Inhibitory effects on growth/proliferation can be directly determined. F) Cystein proteinase dependency, respectively caspase dependency are determined by using specific inhibitors. This provides information about possible involvement of specific proteases in the mechanisms.

On the basis of these studies, a compound of formula (I) according to the invention shows therapeutic efficacy especially against neoplastic diseases and autoimmune diseases. In particular, the compounds of the invention are active against malignancies, e.g. epithelial neoplasms, squamous cell neoplasms, basal cell neoplasms, transitional cell papillomas and carcinomas, adenomas und adenocarcinomas, adnexal and skin appendage neoplasms, mucoepidermoid neoplasms, cystic neoplasms, mucinous and serous neoplasms, ductal-, lobular and medullary neoplasms, acinar cell neoplasms, complex epithelial neoplasms, specialized gonadal neoplasms, paragangliomas and glomus tumors, naevi and melanomas, soft tissue tumors and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, odontogenic tumors, gliomas, neuro-epitheliomatous neoplasms, meningiomas, nerve sheath tumors, granular cell tumors and alveolar soft part sarcomas, Hodgkin's and non Hodgkin's lymphomas, other lymphoreticular neoplasms, plasma cell tumors, mast cell tumors, immunoproliferative diseases, leukemias, miscellaneous myeloproliferative disorders, lymphoproliferative disorders and myelodysplastic syndromes.

The compounds of the invention are likewise active against autoimmune diseases, e.g. against systemic, discoid or subacute cutaneous lupus erythematosus, rheumatoid arthritis, antiphospholipid syndrome, CREST, progressive systemic sclerosis, mixed connective tissue disease (Sharp syndrome), Reiter's syndrome, juvenile arthritis, cold agglutinin disease, essential mixed cryoglobulinemia, rheumatic fever, ankylosing spondylitis, chronic polyarthritis, myasthenia gravis, multiple sclerosis, chronic inflammatory demyelinating polyneuropathy, Guillan-Barré syndrome, dermatomyositis/polymyositis, autoimmune hemolytic anemia, thrompocytopenic purpura, neutropenia, type I diabetes mellitus, thyroiditis (including Hashimoto's and Grave' disease), Addison's disease, polyglandular syndrome, pemphigus (vulgaris, foliaceus, sebaceous and vegetans), bullous and cicatricial pemphigoid, pemphigoid gestationis, epidermolysis bullosa acquisita, linear IgA disease, lichen sclerosus et atrophicus, morbus Duhring, psoriasis vulgaris, guttate, generalized pustular and localized pustular psoriasis, vitiligo, alopecia areata, primary biliary cirrhosis, autoimmune hepatitis, all forms of glomerulonephritis, pulmonal hemorrhage (goodpasture syndrome), IgA nephropathy, pernicious anemia and autoimmune gastritis, inflammatory bowel diseases (including colitis ulcerosa and morbus Crohn), Behcet's disease, Celic-Sprue disease, autoimmune uveitis, autoimmune myocarditis, granulomatous orchitis, aspermatogenesis without orchitis, idiopathic and secondary pulmonary fibrosis, inflammatory diseases with a possibility of autoimmune pathogensesis, such as pyoderma gangrensosum, lichen ruber, sarcoidosis (including Löfgren and cutaneous/subcutaneous type), granuloma anulare, allergic type I and type IV immunological reaction, asthma bronchiale, pollinosis, atopic, contact and airborne dermatitis, large vessel vasculitis (giant cell and Takayasu's arteritis), medium sized vessel vasculitis (polyarteritis nodosa, Kawasaki disease), small vessel vasculitis (Wegener's granulomatosis, Churg Strauss syndrome, microscopic polangiitis, Henoch-Schoenlein purpura, essential cryoglobulinemic vasculitis, cutaneous leukoklastic angiitis), hypersensitivity syndromes, toxic epidermal necrolysis (Stevens-Johnson syndrome, erythema multiforme), diseases due to drug side effects, all forms of cutaneous, organ-specific and systemic effects due to type I-VI (Coombs classification) immunologic forms of reaction, transplantation related pathologies, such as acute and chronic graft versus host and host versus graft disease, involving all organs (skin, heart, kidney, bone marrow, eye, liver, spleen, lung, muscle, central and peripheral nerve system, connective tissue, bone, blood and lymphatic vessel, genito-urinary system, ear, cartilage, primary and secondary lymphatic system including bone marrow, lymph node, thymus, gastro-intestinal tract, including oro-pharynx, esophageus, stomach, small intestine, colon, and rectum, including parts of above mentioned organs down to single cell level and substructures, e.g. stem cells).

A compound of formula (I) can be administered alone or in combination with one or more other therapeutic agents, possible combination therapy taking the form of fixed combinations, or the administration of a compound of the invention and one or more other therapeutic agents being staggered or given independently of one another, or the combined administration of fixed combinations and one or more other therapeutic agents. A compound of formula (I) can, besides or in addition, be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk. Particularly preferred is the use of compounds of formula (I) in combination with radiotherapy.

Therapeutic agents for possible combination are especially one or more cytostatic or cytotoxic compounds, for example a chemotherapeutic agent or several selected from the group comprising indarubicin, cytarabine, interferon, hydroxyurea, bisulfan, or an inhibitor of polyamine biosynthesis, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, a classical cytostatic, an inhibitor of the interaction of an SH2 domain with a phosphorylated protein, an inhibitor of Bcl-2 and modulators of the Bcl-2 family members such as Bax, Bid, Bad, Bim, Nip3 and BH3-only proteins.

A compound according to the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds.

With the groups of preferred compounds of formula (I) mentioned hereinafter, definitions of substituents from the general definitions mentioned hereinbefore may reasonably be used, for example, to replace more general definitions with more specific definitions or especially with definitions characterized as being preferred.

In particular, the invention refers to compounds of formula (I) wherein $R^1$ represents optionally substituted aryl or heteroaryl, wherein aryl and heteroaryl may be substituted by one to five substituents selected from lower alkyl, halo-lower alkyl, lower alkoxy-lower alkyl, lower alkenyl, optionally substituted phenyl, heteroaryl, heterocyclyl, lower alkoxy, lower alkoxy-lower alkoxy, lower alkenyloxy, phenoxy, dialkylamino, lower alkylsulfonyl, halo-lower alkylsulfinyl, halogen, cyano and nitro;

$R^2$ is aryl or heteroaryl wherein aryl or heteroaryl may be substituted by one to five substituents independently chosen from lower alkyl, halo-lower alkyl, cycloalkyl, cycloalkyl-lower alkyl, hydroxy-lower alkyl, lower alkoxy-lower alkyl, lower alkoxy-lower alkoxy-lower alkyl, halo-lower alkoxy-lower alkyl, heterocyclyl, heterocyclyl-lower alkyl, optionally substituted phenyl, optionally substituted phenyl-lower alkyl, optionally substituted heteroaryl, optionally substituted heteroaryl-lower alkyl, optionally substituted alkenyl, optionally substituted alkinyl, hydroxy, lower alkoxy, optionally substituted alkenyloxy, optionally substituted alkinyloxy, halo-lower alkoxy, cycloalkoxy, cycloalkyl-lower alkoxy, hydroxy-lower alkoxy, lower alkoxy-lower alkoxy, heterocyclyloxy, heterocyclyl-lower alkoxy, optionally substituted phenyloxy, optionally substituted phenyl-lower alkoxy, optionally substituted heteroaryloxy, optionally substituted heteroaryl-lower alkoxy, sulfamoyloxy, carbamoyloxy, lower alkyl-carbonyloxy, amino, carbamoyl, sulfamoyl, amino-lower alkyl or amino-lower alkylamino, wherein in each case the nitrogen atom is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl and lower alkylcarbonyl, or wherein the two substituents on nitrogen form together with the nitrogen heteroaryl or heterocyclyl;

lower alkylcarbonyl, cycloalkylcarbonyl, optionally substituted phenylcarbonyl, optionally substituted heteroarylcarbonyl, heterocyclylcarbonyl, carboxy, lower alkoxycarbonyl, hydroxy-lower alkoxycarbonyl, lower alkoxy-lower alkoxycarbonyl, optionally substituted phenyl-lower alkoxycarbonyl, cyano, mercapto, lower alkylmercapto, optionally substituted phenylmercapto, lower alkylsulfinyl, halo-lower alkylsulfinyl, optionally substituted phenylsulfinyl, lower alkylsulfonyl, halo-lower alkylsulfonyl, optionally substituted phenylsulfonyl, optionally substituted phenyl-lower alkylsulfonyl, halogen, and cyano;

and wherein two adjacent substituents together with the atoms of aryl or heteroaryl may form a 5, 6 or 7 membered carbocyclic or heterocyclic ring;

$R^3$ represents a group $CH_2NR^6R^7$;

$R^4$ represents hydrogen, alkyl, cycloalkyl, cycloalkyl-alkyl, hydroxyalkyl, alkoxyalkyl, hydroxyalkoxyalkyl, alkoxyalkoxyalkyl, optionally substituted alkenyl, optionally substituted alkinyl, aminoalkyl, wherein the nitrogen can be substituted by up to two substituents selected from lower alkyl, cycloalkyl, cycloalkyl-lower alkyl, hydroxy-lower alkyl, lower alkoxy-lower alkyl, hydroxy-lower alkoxy-lower alkyl or lower alkoxy-lower alkoxy-lower alkyl; optionally substituted phenyl, optionally substituted phenyl-lower alkyl, optionally substituted heteroaryl, optionally substituted heteroaryl-lower alkyl, heterocyclyl, optionally substituted alkenyl, optionally substituted alkinyl, lower alkylcarbonyl, cycloalkylcarbonyl, optionally substituted phenylcarbonyl, lower alkylsulfonyl, or optionally substituted phenylsulfonyl;

$R^5$ represents hydrogen or lower alkyl;

or $R^4$ and $R^5$ together with the nitrogen they are bound to represent a five, six or seven membered heterocyclic ring that can be partially or fully unsaturated and may be optionally substituted by one or more substituents selected from oxo, lower alkyl, halo-lower alkyl, hydroxy-lower alkyl, lower alkoxy-lower alkyl or lower alkoxy;

$R^6$ represents hydrogen, alkyl, cycloalkyl, cycloalkyl-alkyl, hydroxyalkyl, alkoxyalkyl, hydroxyalkoxyalkyl, alkoxyalkoxyalkyl, optionally substituted phenyl-lower alkyl, optionally substituted heteroaryl-lower alkyl, heterocyclyl, optionally substituted alkenyl, optionally substituted alkinyl, aminoalkyl or aminoalkylcarbonyl, wherein the nitrogen can be substituted by up to two substituents selected from lower alkyl, cycloalkyl, cycloalkyl-lower alkyl, hydroxy-lower alkyl, lower alkoxy-lower alkyl, hydroxy-lower alkoxy-lower alkyl and lower alkoxy-lower alkoxy-lower alkyl; optionally substituted alkenyl, optionally substituted alkinyl, lower alkylcarbonyl, cycloalkylcarbonyl, optionally substituted phenylcarbonyl, lower alkylsulfonyl, or optionally substituted phenylsulfonyl;

or aryl substituted by one substituent selected from carboxy, lower alkoxycarbonyl, hydroxy-lower alkoxycarbonyl, lower alkoxy-lower alkoxycarbonyl, optionally substituted phenyl-lower alkoxycarbonyl, heteroaryl, heterocyclyl, a carbamoyl group $CONR^4R^5$, and a sulfamoyl group $SO_2NR^4R^5$, wherein such substituents on aryl may be directly linked or linked via a spacer selected from lower alkylidene, oxygen, oxymethyl, nitrogen optionally substituted by lower alkyl, or aminomethyl wherein the amino nitrogen is optionally substituted by lower alkyl; and optionally one or two further substituents selected from lower alkyl, halo-lower alkyl, lower alkoxy-lower alkyl, lower alkoxy, lower alkoxy-lower alkoxy, halo and nitro;

or aryl substituted by one substituent selected from amino optionally substituted by one or two substituents selected from lower alkyl, hydroxyalkyl, alkoxyalkyl, aminoalkyl and optionally substituted alkylcarbonyl, and an aminocarbonylamino group $NHCONR^4R^5$, wherein such substituents on aryl may be directly linked or linked via a lower alkylidene spacer; and optionally one or two further substituents selected from lower alkyl, halo-lower alkyl, lower alkoxy-lower alkyl, lower alkoxy, lower alkoxy-lower alkoxy, halo and nitro;

or aryl substituted by one substituent selected from cyano, cyanomethyl, sulfo, lower alkoxysulfonyl, hydroxy-lower alkoxysulfonyl, lower alkoxy-lower alkoxysulfonyl and optionally substituted phenyl-lower alkoxysulfonyl; and optionally one or two further substituents selected from lower alkyl, halo-lower alkyl, lower alkoxy-lower alkyl, lower alkoxy, lower alkoxy-lower alkoxy, halo and nitro;

or heteroaryl, optionally substituted by one or two substituents selected from lower alkyl, halo-lower alkyl, lower alkoxy-lower alkyl, lower alkoxy, lower alkoxy-lower alkoxy, carboxy, lower alkoxycarbonyl, a carbamoyl group $CONR^4R^5$, a sulfamoyl group $SO_2NR^4R^5$, amino optionally substituted by one or two substituents selected from lower alkyl, hydroxyalkyl, alkoxyalkyl, aminoalkyl and optionally substituted alkylcarbonyl, an aminocarbonylamino group $NHCONR^4R^5$, cyano, and halo; and wherein substituents carboxy, lower alkoxycarbonyl, carbamoyl or sulfamoyl may be directly linked or linked via a spacer selected from lower alkylidene, oxygen, oxymethyl, nitrogen optionally substituted by lower alkyl, and aminomethyl wherein the amino nitrogen is optionally substituted by lower alkyl, alkylcarbonyl, alkoxycarbonyl or aminocarbonyl; and wherein substituents amino and aminocarbonylamino may be directly linked or linked via a lower alkylidene spacer;

$R^7$ represents hydrogen, lower alkyl, lower alkylcarbonyl, lower alkoxycarbonyl or lower alkoxysulfonyl;

or $R^6$ and $R^7$ together with the nitrogen they are bound to represent a five, six or seven membered heterocyclic ring that can be partially or fully unsaturated and may be optionally substituted by one or more groups selected from oxo, lower alkyl, halo-lower alkyl, hydroxy-lower alkyl, lower alkoxy-lower alkyl or lower alkoxy;

and salts thereof.

More particularly, the invention refers to compounds of formula (I) wherein $R^1$ represents optionally substituted aryl or heteroaryl, wherein aryl and heteroaryl may be substituted by one to five substituents selected from lower alkyl, halo-lower alkyl, lower alkoxy-lower alkyl, optionally substituted phenyl, heteroaryl, heterocyclyl, lower alkoxy, phenoxy, dialkylamino, halo-lower alkylsulfinyl, halogen and cyano;

$R^2$ is aryl or heteroaryl wherein aryl or heteroaryl may be substituted by one to five substituents independently chosen from lower alkyl, halo-lower alkyl, lower alkoxy-lower alkyl, heterocyclyl, heterocyclyl-lower alkyl, optionally substituted phenyl, optionally substituted phenyl-lower alkyl, optionally substituted heteroaryl, optionally substituted heteroaryl-lower alkyl, optionally substituted alkinyl, hydroxy, lower alkoxy, optionally substituted alkenyloxy, optionally substituted alkinyloxy, halo-lower alkoxy, cycloalkoxy, cycloalkyl-lower alkoxy, lower alkoxy-lower alkoxy, heterocyclyloxy, heterocyclyl-lower alkoxy, optionally substituted phenyloxy, optionally substituted phenyl-lower alkoxy, optionally substituted heteroaryloxy, optionally substituted heteroaryl-lower alkoxy, sulfamoyloxy, carbamoyloxy, lower alkyl-carbonyloxy, amino, carbamoyl, sulfamoyl, amino-lower alkyl or amino-lower alkylamino, wherein in each case the nitrogen atom is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl and lower alkylcarbonyl, or wherein the two substituents on nitrogen form together with the nitrogen heteroaryl or heterocyclyl;

halo-lower alkylsulfinyl, optionally substituted phenylsulfinyl, lower alkylsulfonyl, halo-lower alkylsulfonyl, optionally substituted phenylsulfonyl, optionally substituted phenyl-lower alkylsulfonyl, halogen, and cyano;

and wherein two adjacent substituents together with the atoms of aryl or heteroaryl may form a 5, 6 or 7 membered carbocyclic or heterocyclic ring;

$R^3$ represents a group $CH_2NR^6R^7$;

$R^4$ represents hydrogen, alkyl, hydroxyalkyl, alkoxyalkyl, aminoalkyl, wherein the nitrogen can be substituted by up to two substituents selected from lower alkyl and lower alkoxy-lower alkyl;

$R^5$ represents hydrogen or lower alkyl;

or $R^4$ and $R^5$ together with the nitrogen they are bound to represent a five, six or seven membered heterocyclic ring that can be partially or fully unsaturated and may be optionally substituted by one or more substituents selected from oxo, lower alkyl, halo-lower alkyl, hydroxy-lower alkyl, lower alkoxy-lower alkyl or lower alkoxy;

$R^6$ represents hydrogen, alkyl, cycloalkyl, cycloalkylalkyl, hydroxyalkyl, alkoxyalkyl, optionally substituted phenyl-lower alkyl, optionally substituted heteroaryl-lower alkyl, heterocyclyl, optionally substituted alkenyl, optionally substituted alkinyl, aminoalkyl wherein the nitrogen can be substituted by up to two substituents selected from lower alkyl, cycloalkyl, cycloalkyl-lower alkyl, hydroxy-lower alkyl, lower alkoxy-lower alkyl, hydroxy-lower alkoxy-lower alkyl and lower alkoxy-lower alkoxy-lower alkyl; optionally substituted alkenyl, optionally substituted alkinyl, lower alkylcarbonyl, cycloalkylcarbonyl, optionally substituted phenylcarbonyl, lower alkylsulfonyl, or optionally substituted phenylsulfonyl;

or phenyl substituted by one substituent selected from carboxy, lower alkoxycarbonyl, hydroxy-lower alkoxycarbonyl, lower alkoxy-lower alkoxycarbonyl, optionally substituted phenyl-lower alkoxycarbonyl, heteroaryl, heterocyclyl, a carbamoyl group $CONR^4R^5$, and a sulfamoyl group $SO_2NR^4R^5$, wherein such substituents on phenyl may be directly linked or linked via a spacer selected from lower alkylidene, oxygen, oxymethyl, nitrogen optionally substituted by lower alkyl, or aminomethyl wherein the amino nitrogen is optionally substituted by lower alkyl; and optionally one or two further substituents selected from lower alkyl, halo-lower alkyl, lower alkoxy-lower alkyl, lower alkoxy, lower alkoxy-lower alkoxy, halo and nitro;

or phenyl substituted by one substituent selected from amino optionally substituted by one or two substituents selected from lower alkyl, hydroxyalkyl, alkoxyalkyl, aminoalkyl and optionally substituted alkylcarbonyl, and an aminocarbonylamino group $NHCONR^4R^5$, wherein such substituents on phenyl may be directly linked or linked via a lower alkylidene spacer; and optionally one or two further substituents selected from lower alkyl, halo-lower alkyl, lower alkoxy-lower alkyl, lower alkoxy, lower alkoxy-lower alkoxy, halo and nitro;

or phenyl substituted by one substituent selected from cyano, cyanomethyl, sulfo, lower alkoxysulfonyl, hydroxy-lower alkoxysulfonyl, lower alkoxy-lower alkoxysulfonyl and optionally substituted phenyl-lower alkoxysulfonyl; and optionally one or two further substituents selected from lower alkyl, halo-lower alkyl, lower alkoxy-lower alkyl, lower alkoxy, lower alkoxy-lower alkoxy, halo and nitro;

or pyridyl, pyridazinyl, pyrimidinyl, pyrazinyl, quinolinyl or isoquinolinyl, each optionally substituted by one or two substituents selected from lower alkyl, halo-lower alkyl, lower alkoxy-lower alkyl, lower alkoxy, lower alkoxy-lower alkoxy, carboxy, lower alkoxycarbonyl, a carbamoyl group $CONR^4R^5$, a sulfamoyl group $SO_2NR^4R^5$, amino optionally substituted by one or two substituents selected from lower alkyl, hydroxyalkyl, alkoxyalkyl, aminoalkyl and optionally substituted alkylcarbonyl, an aminocarbonylamino group NHCONR⁴R⁵, cyano, and halo; and wherein substituents carboxy, lower alkoxycarbonyl, carbamoyl or sulfamoyl may be directly linked or linked via a spacer selected from lower alkylidene, oxygen, oxymethyl, nitrogen optionally substituted by lower alkyl, and aminomethyl wherein the amino nitrogen is optionally substituted by lower alkyl, alkylcarbonyl, alkoxycarbonyl or aminocarbonyl; and wherein substituents amino and aminocarbonylamino may be directly linked or linked via a lower alkylidene spacer;

R⁷ represents hydrogen, lower alkyl, lower alkylcarbonyl, lower alkoxycarbonyl or lower alkoxysulfonyl;

or R⁶ and R⁷ together with the nitrogen they are bound to represent a five, six or seven membered heterocyclic ring that can be partially or fully unsaturated and may be optionally substituted by one or more groups selected from oxo, lower alkyl, halo-lower alkyl, hydroxy-lower alkyl, lower alkoxy-lower alkyl or lower alkoxy;

and salts thereof.

Preferably, the invention refers to compounds of formula (I) wherein

R¹ represents optionally substituted aryl or heteroaryl, wherein aryl and heteroaryl may be substituted by one to five substituents selected from lower alkyl, halo-lower alkyl, lower alkoxy-lower alkyl, optionally substituted phenyl, heteroaryl, heterocyclyl, lower alkoxy, lower alkoxy-lower alkoxy, phenoxy, dialkylamino, halo-lower alkylsulfinyl, halogen and cyano;

R² is aryl or heteroaryl wherein aryl or heteroaryl may be substituted by one to five substituents independently chosen from lower alkyl, halo-lower alkyl, lower alkoxy-lower alkyl, heterocyclyl, heterocyclyl-lower alkyl, optionally substituted phenyl, optionally substituted phenyl-lower alkyl, optionally substituted heteroaryl, optionally substituted heteroaryl-lower alkyl, optionally substituted alkenyloxy, optionally substituted alkinyloxy, halo-lower alkoxy, cycloalkoxy, cycloalkyl-lower alkoxy, lower alkoxy-lower alkoxy, heterocyclyloxy, heterocyclyl-lower alkoxy, optionally substituted phenyloxy, optionally substituted phenyl-lower alkoxy, optionally substituted heteroaryloxy, optionally substituted heteroaryl-lower alkoxy, sulfamoyloxy, carbamoyloxy, lower alkyl-carbonyloxy, dialkylamino, carbamoyl, sulfamoyl, halo-lower alkylsulfinyl, optionally substituted phenylsulfinyl, lower alkylsulfonyl, halo-lower alkylsulfonyl, optionally substituted phenylsulfonyl, optionally substituted phenyl-lower alkylsulfonyl and halogen;

and wherein two adjacent substituents together with the atoms of aryl or heteroaryl may form a 5, 6 or 7 membered carbocyclic or heterocyclic ring;

R³ represents a group CH₂NR⁶R⁷;

R⁴ represents hydrogen, alkyl, hydroxyalkyl, alkoxyalkyl, aminoalkyl, wherein the nitrogen can be substituted by up to two substituents selected from lower alkyl and lower alkoxy-lower alkyl;

R⁵ represents hydrogen or lower alkyl;

or R⁴ and R⁵ together with the nitrogen they are bound to represent a five, six or seven membered heterocyclic ring that can be partially or fully unsaturated and may be optionally substituted by one or more substituents selected from oxo, lower alkyl, halo-lower alkyl, hydroxy-lower alkyl, lower alkoxy-lower alkyl or lower alkoxy;

R⁶ represents hydrogen, lower alkyl, heterocyclyl, optionally substituted alkenyl, optionally substituted alkinyl, aminoalkyl wherein the nitrogen can be substituted by up to two substituents selected from lower alkyl, cycloalkyl, cycloalkyl-lower alkyl, hydroxy-lower alkyl, lower alkoxy-lower alkyl, hydroxy-lower alkoxy-lower alkyl and lower alkoxy-lower alkoxy-lower alkyl;

or phenyl substituted by one substituent selected from carboxy, lower alkoxycarbonyl, hydroxy-lower alkoxycarbonyl, lower alkoxy-lower alkoxycarbonyl, optionally substituted phenyl-lower alkoxycarbonyl, heteroaryl, heterocyclyl, a carbamoyl group CONR⁴R⁵, and a sulfamoyl group SO₂NR⁴R⁵, wherein such substituents on phenyl may be directly linked or linked via a spacer selected from lower alkylidene, oxygen, oxymethyl, nitrogen optionally substituted by lower alkyl, or aminomethyl wherein the amino nitrogen is optionally substituted by lower alkyl; and optionally one or two further substituents selected from lower alkyl, halo-lower alkyl, lower alkoxy-lower alkyl, lower alkoxy, lower alkoxy-lower alkoxy, halo and nitro;

or phenyl substituted by one substituent selected from amino optionally substituted by one or two substituents selected from lower alkyl, hydroxyalkyl, alkoxyalkyl, aminoalkyl and optionally substituted alkylcarbonyl, and an aminocarbonylamino group NHCONR⁴R⁵, wherein such substituents on phenyl may be directly linked or linked via a lower alkylidene spacer; and optionally one or two further substituents selected from lower alkyl, halo-lower alkyl, lower alkoxy-lower alkyl, lower alkoxy, lower alkoxy-lower alkoxy, halo and nitro;

or phenyl substituted by one substituent selected from cyano, cyanomethyl, sulfo, lower alkoxysulfonyl, hydroxy-lower alkoxysulfonyl, lower alkoxy-lower alkoxysulfonyl and optionally substituted phenyl-lower alkoxysulfonyl; and optionally one or two further substituents selected from lower alkyl, halo-lower alkyl, lower alkoxy-lower alkyl, lower alkoxy, lower alkoxy-lower alkoxy, halo and nitro;

or pyridyl optionally substituted by one or two substituents selected from lower alkyl, halo-lower alkyl, lower alkoxy-lower alkyl, lower alkoxy, lower alkoxy-lower alkoxy, carboxy, lower alkoxycarbonyl, a carbamoyl group CONR⁴R⁵, a sulfamoyl group SO₂NR⁴R⁵, amino optionally substituted by one or two substituents selected from lower alkyl, hydroxyalkyl, alkoxyalkyl, aminoalkyl and optionally substituted alkylcarbonyl, an aminocarbonylamino group NHCONR⁴R⁵, cyano, and halo; and wherein substituents carboxy, lower alkoxycarbonyl, carbamoyl or sulfamoyl may be directly linked or linked via a spacer selected from lower alkylidene, oxygen, oxymethyl, nitrogen optionally substituted by lower alkyl, and aminomethyl wherein the amino nitrogen is optionally substituted by lower alkyl, alkylcarbonyl, alkoxycarbonyl or aminocarbonyl; and wherein substituents amino and aminocarbonylamino may be directly linked or linked via a lower alkylidene spacer;

R⁷ represents hydrogen or lower alkyl;

or R⁶ and R⁷ together with the nitrogen they are bound to represent a five, six or seven membered heterocyclic ring that can be partially or fully unsaturated and may be optionally substituted by one or more groups selected from oxo, lower alkyl, halo-lower alkyl, hydroxy-lower alkyl, lower alkoxy-lower alkyl or lower alkoxy;

and salts thereof.

More particularly, the invention refers to compounds of formula (I) wherein

R¹ represents phenyl substituted by up to two substituents independently selected from lower alkyl, lower alkoxy-lower alkyl, lower alkoxy, lower alkoxy-lower alkoxy and halogen;

R² is aryl optionally substituted by one to three substituents independently chosen from lower alkyl, lower alkoxy-lower alkyl, optionally substituted alkenyloxy, optionally substituted alkinyloxy, halo-lower alkoxy, cycloalkoxy, cycloalkyl-lower alkoxy, lower alkoxy-lower alkoxy, heterocyclyloxy, heterocyclyl-lower alkoxy and halogen;

and wherein two adjacent substituents together with the atoms of aryl or heteroaryl may form a 5, 6 or 7 membered carbocyclic or heterocyclic ring;

$R^3$ represents a group $CH_2NR^6R^7$;

$R^4$ represents hydrogen, alkyl, alkoxyalkyl, hydroxyalkyl, aminoalkyl, wherein the nitrogen can be substituted by up to two substituents selected from lower alkyl and lower alkoxy-lower alkyl;

$R^5$ represents hydrogen or lower alkyl;

or $R^4$ and $R^5$ together with the nitrogen they are bound to represent a five, six or seven membered heterocyclic ring that can be partially or fully unsaturated and may be optionally substituted by one or more substituents selected from oxo, lower alkyl, halo-lower alkyl, hydroxy-lower alkyl, lower alkoxy-lower alkyl or lower alkoxy;

$R^6$ represents phenyl substituted by one substituent selected from heteroaryl, heterocyclyl, a carbamoyl group $CONR^4R^5$, and a sulfamoyl group $SO_2NR^4R^5$, wherein such substituents on phenyl may be directly linked or linked via a spacer selected from lower alkylidene, oxygen, oxymethyl, nitrogen optionally substituted by lower alkyl, or aminomethyl wherein the amino nitrogen is optionally substituted by lower alkyl;

or phenyl substituted by one substituent selected from amino optionally substituted by one or two substituents selected from lower alkyl, hydroxyalkyl, alkoxyalkyl, aminoalkyl and optionally substituted alkylcarbonyl, and an aminocarbonylamino group $NHCONR^4R^5$, wherein such substituents on phenyl may be directly linked or linked via a lower alkylidene spacer;

or pyridyl optionally substituted by one or two substituents selected from lower alkoxy, lower alkoxy-lower alkoxy, carboxy, lower alkoxycarbonyl, a carbamoyl group $CONR^4R^5$, a sulfamoyl group $SO_2NR^4R^5$, amino optionally substituted by one or two substituents selected from lower alkyl, hydroxyalkyl, alkoxyalkyl, aminoalkyl and optionally substituted alkylcarbonyl, an aminocarbonylamino group $NHCONR^4R^5$, cyano, and halo; and wherein substituents carboxy, lower alkoxycarbonyl, carbamoyl or sulfamoyl may be directly linked or linked via a spacer selected from lower alkylidene, oxygen, oxymethyl, nitrogen optionally substituted by lower alkyl, and aminomethyl wherein the amino nitrogen is optionally substituted by lower alkyl, alkylcarbonyl, alkoxycarbonyl or aminocarbonyl; and wherein substituents amino and aminocarbonylamino may be directly linked or linked via a lower alkylidene spacer;

$R^7$ represents hydrogen or lower alkyl;

and salts thereof.

In another aspect, the invention refers to compounds of formula (I) wherein $R^1$ represents optionally substituted aryl, aralkyl or heteroaryl, wherein aryl, aryl in aralkyl and heteroaryl may be substituted by one to five substituents selected from lower alkyl, halo-lower alkyl, lower alkoxy-lower alkyl, lower alkenyl, optionally substituted phenyl, heteroaryl, heterocyclyl, lower alkoxy, lower alkenyloxy, phenoxy, dialkylamino, lower alkylsulfonyl, halo-lower alkylsulfinyl, halogen, cyano and nitro;

$R^2$ is aryl or heteroaryl wherein aryl or heteroaryl may be substituted by one to five substituents independently chosen from lower alkyl, halo-lower alkyl, cycloalkyl, cycloalkyl-lower alkyl, hydroxy-lower alkyl, lower alkoxy-lower alkyl, lower alkoxy-lower alkoxy-lower alkyl, halo-lower alkoxy-lower alkyl, heterocyclyl, heterocyclyl-lower alkyl, optionally substituted phenyl, optionally substituted phenyl-lower alkyl, optionally substituted heteroaryl, optionally substituted heteroaryl-lower alkyl, optionally substituted alkenyl, optionally substituted alkinyl, hydroxy, lower alkoxy, optionally substituted alkenyloxy, optionally substituted alkinyloxy, halo-lower alkoxy, cycloalkoxy, cycloalkyl-lower alkoxy, hydroxy-lower alkoxy, lower alkoxy-lower alkoxy, heterocyclyloxy, heterocyclyl-lower alkoxy, optionally substituted phenyloxy, optionally substituted phenyl-lower alkoxy, optionally substituted heteroaryloxy, optionally substituted heteroaryl-lower alkoxy, sulfamoyloxy, carbamoyloxy, lower alkyl-carbonyloxy, amino, carbamoyl, sulfamoyl, amino-lower alkyl or amino-lower alkylamino, wherein in each case the nitrogen atom is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl and lower alkylcarbonyl, or wherein the two substituents on nitrogen form together with the nitrogen heteroaryl or heterocyclyl;

lower alkylcarbonyl, cycloalkylcarbonyl, optionally substituted phenylcarbonyl, optionally substituted heteroarylcarbonyl, heterocyclylcarbonyl, carboxy, lower alkoxycarbonyl, hydroxy-lower alkoxycarbonyl, lower alkoxy-lower alkoxycarbonyl, optionally substituted phenyl-lower alkoxycarbonyl, cyano, mercapto, lower alkylmercapto, optionally substituted phenylmercapto, lower alkylsulfinyl, halo-lower alkylsulfinyl, optionally substituted phenylsulfinyl, lower alkylsulfonyl, halo-lower alkylsulfonyl, optionally substituted phenylsulfonyl, optionally substituted phenyl-lower alkylsulfonyl, halogen, and cyano;

and wherein two adjacent substituents together with the atoms of aryl or heteroaryl may form a 5, 6 or 7 membered carbocyclic or heterocyclic ring;

$R^3$ represents phenyl substituted by one substituent selected from carboxy, lower alkoxycarbonyl, hydroxy-lower alkoxycarbonyl, lower alkoxy-lower alkoxycarbonyl, optionally substituted phenyl-lower alkoxycarbonyl, heteroaryl, heterocyclyl, a carbamoyl group $CONR^4R^5$, and a sulfamoyl group $SO_2NR^4R^5$, wherein such substituents on phenyl may be directly linked or linked via a spacer selected from lower alkylidene, oxygen, oxymethyl, nitrogen optionally substituted by lower alkyl, or aminomethyl wherein the amino nitrogen is optionally substituted by lower alkyl; and optionally one or two further substituents selected from lower alkyl, halo-lower alkyl, lower alkoxy-lower alkyl, lower alkoxy, lower alkoxy-lower alkoxy, halo and nitro;

or phenyl substituted by one substituent selected from amino optionally substituted by one or two substituents selected from lower alkyl, hydroxyalkyl, alkoxyalkyl, aminoalkyl and optionally substituted alkylcarbonyl, and an aminocarbonylamino group $NHCONR^4R^5$, wherein such substituents on phenyl may be directly linked or linked via a lower alkylidene spacer; and optionally one or two further substituents selected from lower alkyl, halo-lower alkyl, lower alkoxy-lower alkyl, lower alkoxy, lower alkoxy-lower alkoxy, halo and nitro;

or phenyl substituted by one substituent selected from cyano, cyanomethyl, sulfo, lower alkoxysulfonyl, hydroxy-lower alkoxysulfonyl, lower alkoxy-lower alkoxysulfonyl and optionally substituted phenyl-lower alkoxysulfonyl; and optionally one or two further substituents selected from lower alkyl, halo-lower alkyl, lower alkoxy-lower alkyl, lower alkoxy, lower alkoxy-lower alkoxy, halo and nitro;

or pyrazolyl, imidazolyl, oxazolyl, isoxazolyl, thiazolyl, isothiazolyl, oxadiazolyl, thiadiazolyl, pyridyl, pyridazinyl, pyrimidinyl, pyrazinyl, quinolinyl or isoquinolinyl, each optionally substituted by one or two substituents selected from lower alkyl, halo-lower alkyl, lower alkoxy-lower alkyl, lower alkoxy, lower alkoxy-lower alkoxy, carboxy, lower alkoxycarbonyl, a carbamoyl group $CONR^4R^5$, a sulfamoyl group $SO_2NR^4R^5$, amino optionally substituted by one or two substituents selected from lower alkyl, hydroxyalkyl, alkoxyalkyl, aminoalkyl and optionally substituted alkylcarbonyl, an aminocarbonylamino group $NHCONR^4R^5$, cyano, and halo; and wherein substituents carboxy, lower alkoxycarbonyl, carbamoyl or sulfamoyl may be directly linked or linked via a spacer selected from lower alkylidene, oxygen, oxymethyl, nitrogen optionally substituted by lower alkyl, and aminomethyl wherein the amino nitrogen is optionally substituted by lower alkyl, alkylcarbonyl, alkoxycarbonyl or aminocarbonyl; and wherein substituents amino and aminocarbonylamino may be directly linked or linked via a lower alkylidene spacer;

$R^4$ represents hydrogen, alkyl, cycloalkyl, cycloalkylalkyl, hydroxyalkyl, alkoxyalkyl, hydroxyalkoxyalkyl, alkoxyalkoxyalkyl, optionally substituted alkenyl, optionally substituted alkinyl, aminoalkyl, wherein the nitrogen can be substituted by up to two substituents selected from lower alkyl, cycloalkyl, cycloalkyl-lower alkyl, hydroxy-lower alkyl, lower alkoxy-lower alkyl, hydroxy-lower alkoxy-lower alkyl or lower alkoxy-lower alkoxy-lower alkyl; optionally substituted phenyl, optionally substituted phenyl-lower alkyl, optionally substituted heteroaryl, optionally substituted heteroaryl-lower alkyl, heterocyclyl, optionally substituted alkenyl, optionally substituted alkinyl, lower alkylcarbonyl, cycloalkylcarbonyl, optionally substituted phenylcarbonyl, lower alkylsulfonyl, or optionally substituted phenylsulfonyl;

$R^5$ represents hydrogen or lower alkyl;

or $R^4$ and $R^5$ together with the nitrogen they are bound to represent a five, six or seven membered heterocyclic ring that can be partially or fully unsaturated and may be optionally substituted by one or more substituents selected from oxo, lower alkyl, halo-lower alkyl, hydroxy-lower alkyl, lower alkoxy-lower alkyl or lower alkoxy;

and salts thereof.

Preferably, the invention refers to compounds of formula (I) wherein $R^1$ represents optionally substituted aryl or heteroaryl, wherein aryl and heteroaryl may be substituted by one to five substituents selected from lower alkyl, halo-lower alkyl, lower alkoxy-lower alkyl, optionally substituted phenyl, heteroaryl, heterocyclyl, lower alkoxy, phenoxy, dialkylamino, halo-lower alkylsulfinyl, halogen and cyano;

$R^2$ is aryl or heteroaryl wherein aryl or heteroaryl may be substituted by one to five substituents independently chosen from lower alkyl, halo-lower alkyl, lower alkoxy-lower alkyl, heterocyclyl, heterocyclyl-lower alkyl, optionally substituted phenyl, optionally substituted phenyl-lower alkyl, optionally substituted heteroaryl, optionally substituted heteroaryl-lower alkyl, optionally substituted alkinyl, hydroxy, lower alkoxy, optionally substituted alkenyloxy, optionally substituted alkinyloxy, halo-lower alkoxy, cycloalkoxy, cycloalkyl-lower alkoxy, lower alkoxy-lower alkoxy, heterocyclyloxy, heterocyclyl-lower alkoxy, optionally substituted phenyloxy, optionally substituted phenyl-lower alkoxy, optionally substituted heteroaryloxy, optionally substituted heteroaryl-lower alkoxy, sulfamoyloxy, carbamoyloxy, lower alkyl-carbonyloxy, amino, carbamoyl, sulfamoyl, amino-lower alkyl or amino-lower alkylamino, wherein in each case the nitrogen atom is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl and lower alkylcarbonyl, or wherein the two substituents on nitrogen form together with the nitrogen heteroaryl or heterocyclyl;

halo-lower alkylsulfinyl, optionally substituted phenylsulfinyl, lower alkylsulfonyl, halo-lower alkylsulfonyl, optionally substituted phenylsulfonyl, optionally substituted phenyl-lower alkylsulfonyl, halogen, and cyano;

and wherein two adjacent substituents together with the atoms of aryl or heteroaryl may form a 5, 6 or 7 membered carbocyclic or heterocyclic ring;

$R^3$ represents phenyl substituted by one substituent selected from carboxy, lower alkoxycarbonyl, hydroxy-lower alkoxycarbonyl, lower alkoxy-lower alkoxycarbonyl, optionally substituted phenyl-lower alkoxycarbonyl, heteroaryl, heterocyclyl, a carbamoyl group $CONR^4R^5$, and a sulfamoyl group $SO_2NR^4R^5$, wherein such substituents on phenyl may be directly linked or linked via a spacer selected from lower alkylidene, oxygen, oxymethyl, nitrogen optionally substituted by lower alkyl, or aminomethyl wherein the amino nitrogen is optionally substituted by lower alkyl; and optionally one or two further substituents selected from lower alkyl, halo-lower alkyl, lower alkoxy-lower alkyl, lower alkoxy, lower alkoxy-lower alkoxy, halo and nitro;

or phenyl substituted by one substituent selected from amino optionally substituted by one or two substituents selected from lower alkyl, hydroxyalkyl, alkoxyalkyl, aminoalkyl and optionally substituted alkylcarbonyl, and an aminocarbonylamino group $NHCONR^4R^5$, wherein such substituents on phenyl may be directly linked or linked via a lower alkylidene spacer; and optionally one or two further substituents selected from lower alkyl, halo-lower alkyl, lower alkoxy-lower alkyl, lower alkoxy, lower alkoxy-lower alkoxy, halo and nitro;

or phenyl substituted by one substituent selected from cyano, cyanomethyl, sulfo, lower alkoxysulfonyl, hydroxy-lower alkoxysulfonyl, lower alkoxy-lower alkoxysulfonyl and optionally substituted phenyl-lower alkoxysulfonyl; and optionally one or two further substituents selected from lower alkyl, halo-lower alkyl, lower alkoxy-lower alkyl, lower alkoxy, lower alkoxy-lower alkoxy, halo and nitro;

or pyrazolyl, imidazolyl, oxazolyl, isoxazolyl, thiazolyl, isothiazolyl, oxadiazolyl, thiadiazolyl, pyridyl, pyridazinyl, pyrimidinyl, pyrazinyl, quinolinyl or isoquinolinyl, each optionally substituted by one or two substituents selected from lower alkyl, halo-lower alkyl, lower alkoxy-lower alkyl, lower alkoxy, lower alkoxy-lower alkoxy, carboxy, lower alkoxycarbonyl, a carbamoyl group $CONR^4R^5$, a sulfamoyl group $SO_2NR^4R^5$, amino optionally substituted by one or two substituents selected from lower alkyl, hydroxyalkyl, alkoxyalkyl, aminoalkyl and optionally substituted alkylcarbonyl, an aminocarbonylamino group $NHCONR^4R^5$, cyano, and halo; and wherein substituents carboxy, lower alkoxycarbonyl, carbamoyl or sulfamoyl may be directly linked or linked via a spacer selected from lower alkylidene, oxygen, oxymethyl, nitrogen optionally substituted by lower alkyl, and aminomethyl wherein the amino nitrogen is optionally substituted by lower alkyl, alkylcarbonyl, alkoxycarbonyl or aminocarbonyl; and wherein substituents amino and aminocarbonylamino may be directly linked or linked via a lower alkylidene spacer;

$R^4$ represents hydrogen, alkyl, cycloalkyl, cycloalkylalkyl, hydroxyalkyl, alkoxyalkyl, hydroxyalkoxyalkyl, alkoxyalkoxyalkyl, optionally substituted alkenyl, optionally substituted alkinyl, aminoalkyl, wherein the nitrogen can be substituted by up to two substituents selected from lower alkyl, cycloalkyl, cycloalkyl-lower alkyl, hydroxy-lower alkyl, lower alkoxy-lower alkyl, hydroxy-lower alkoxy-lower alkyl or lower alkoxy-lower alkoxy-lower alkyl; optionally substituted phenyl, optionally substituted phenyl-lower alkyl, optionally substituted heteroaryl, optionally substituted heteroaryl-lower alkyl, heterocyclyl, optionally substituted alkenyl, optionally substituted alkinyl, lower alkylcarbonyl, cycloalkylcarbonyl, optionally substituted phenylcarbonyl, lower alkylsulfonyl, or optionally substituted phenylsulfonyl;

$R^5$ represents hydrogen or lower alkyl;

or $R^4$ and $R^5$ together with the nitrogen they are bound to represent a five, six or seven membered heterocyclic ring that can be partially or fully unsaturated and may be optionally substituted by one or more substituents selected from oxo, lower alkyl, halo-lower alkyl, hydroxy-lower alkyl, lower alkoxy-lower alkyl or lower alkoxy;

and salts thereof.

More preferably, the invention refers to compounds of formula (I) wherein $R^1$ represents optionally substituted aryl or heteroaryl, wherein aryl and heteroaryl may be substituted by one to five substituents selected from lower alkyl, halo-lower alkyl, lower alkoxy-lower alkyl, optionally substituted phenyl, heteroaryl, heterocyclyl, lower alkoxy, phenoxy, dialkylamino, halo-lower alkylsulfinyl, halogen and cyano;

$R^2$ is aryl or heteroaryl wherein aryl or heteroaryl may be substituted by one to five substituents independently chosen from lower alkyl, halo-lower alkyl, lower alkoxy-lower alkyl, heterocyclyl, heterocyclyl-lower alkyl, optionally substituted phenyl, optionally substituted phenyl-lower alkyl, optionally substituted heteroaryl, optionally substituted heteroaryl-lower alkyl, optionally substituted alkinyl, lower alkoxy, optionally substituted alkenyloxy, optionally substituted alkinyloxy, halo-lower alkoxy, cycloalkoxy, cycloalkyl-lower alkoxy, lower alkoxy-lower alkoxy, heterocyclyloxy, heterocyclyl-lower alkoxy, optionally substituted phenyloxy, optionally substituted phenyl-lower alkoxy, optionally substituted heteroaryloxy, optionally substituted heteroaryl-lower alkoxy, sulfamoyloxy, carbamoyloxy, lower alkyl-carbonyloxy, amino substituted by one or two substitutents selected from lower alkyl and lower alkylcarbonyl, or wherein the two substituents on nitrogen form together with the nitrogen heteroaryl or heterocyclyl;

halo-lower alkylsulfinyl, halogen and cyano;

and wherein two adjacent substituents together with the atoms of aryl or heteroaryl may form a 5, 6 or 7 membered carbocyclic or heterocyclic ring;

$R^3$ represents phenyl substituted by one substituent selected from carboxy, lower alkoxycarbonyl, hydroxy-lower alkoxycarbonyl, lower alkoxy-lower alkoxycarbonyl, optionally substituted phenyl-lower alkoxycarbonyl, heteroaryl, heterocyclyl, a carbamoyl group $CONR^4R^5$, and a sulfamoyl group $SO_2NR^4R^5$, wherein such substituents on phenyl may be directly linked or linked via a spacer selected from lower alkylidene, oxygen, oxymethyl, nitrogen optionally substituted by lower alkyl, or aminomethyl wherein the amino nitrogen is optionally substituted by lower alkyl; and optionally one or two further substituents selected from lower alkyl, halo-lower alkyl, lower alkoxy-lower alkyl, lower alkoxy, lower alkoxy-lower alkoxy, and halo;

or phenyl substituted by one substituent selected from amino optionally substituted by one or two substituents selected from lower alkyl, hydroxyalkyl, alkoxyalkyl, aminoalkyl and optionally substituted alkylcarbonyl, and an aminocarbonylamino group $NHCONR^4R^5$, wherein such substituents on phenyl may be directly linked or linked via a lower alkylidene spacer; and optionally one or two further substituents selected from lower alkyl, halo-lower alkyl, lower alkoxy-lower alkyl, lower alkoxy, lower alkoxy-lower alkoxy, and halo;

or phenyl substituted by one substituent selected from cyano, cyanomethyl, sulfo, lower alkoxysulfonyl, hydroxy-lower alkoxysulfonyl, lower alkoxy-lower alkoxysulfonyl and optionally substituted phenyl-lower alkoxysulfonyl; and optionally one or two further substituents selected from lower alkyl, halo-lower alkyl, lower alkoxy-lower alkyl, lower alkoxy, lower alkoxy-lower alkoxy and halo; or pyridyl, pyridazinyl, pyrimidinyl, pyrazinyl, quinolinyl or isoquinolinyl, each optionally substituted by one or two substituents selected from lower alkyl, halo-lower alkyl, lower alkoxy-lower alkyl, lower alkoxy, lower alkoxy-lower alkoxy, carboxy, lower alkoxycarbonyl, a carbamoyl group $CONR^4R^5$, a sulfamoyl group $SO_2NR^4R^5$, amino optionally substituted by one or two substituents selected from lower alkyl, hydroxyalkyl, alkoxyalkyl, aminoalkyl and optionally substituted alkylcarbonyl, an aminocarbonylamino group $NHCONR^4R^5$, cyano, and halo;

$R^4$ represents hydrogen, alkyl, cycloalkyl, cycloalkylalkyl, hydroxyalkyl, alkoxyalkyl, hydroxyalkoxyalkyl, alkoxyalkoxyalkyl, optionally substituted alkenyl, optionally substituted alkinyl, aminoalkyl, wherein the nitrogen can be substituted by up to two substituents selected from lower alkyl, cycloalkyl, cycloalkyl-lower alkyl, hydroxy-lower alkyl, lower alkoxy-lower alkyl, hydroxy-lower alkoxy-lower alkyl or lower alkoxy-lower alkoxy-lower alkyl; optionally substituted phenyl, optionally substituted phenyl-lower alkyl, optionally substituted heteroaryl, optionally substituted heteroaryl-lower alkyl, heterocyclyl, optionally substituted alkenyl, optionally substituted alkinyl, lower alkylcarbonyl, cycloalkylcarbonyl, optionally substituted phenylcarbonyl, lower alkylsulfonyl, or optionally substituted phenylsulfonyl;

$R^5$ represents hydrogen or lower alkyl;

or $R^4$ and $R^5$ together with the nitrogen they are bound to represent a five, six or seven membered heterocyclic ring that can be partially or fully unsaturated and may be optionally substituted by one or more substituents selected from oxo, lower alkyl, halo-lower alkyl, hydroxy-lower alkyl, lower alkoxy-lower alkyl or lower alkoxy;

and salts thereof.

More particularly, the invention refers to compounds of formula (I) wherein $R^1$ represents phenyl substituted by up to two substituents independently selected from lower alkyl, lower alkoxy lower alkyl, lower alkoxy, lower alkoxy lower alkoxy and halogen;

$R^2$ is aryl optionally substituted by one to three substituents independently chosen from lower alkyl, lower alkoxy-lower alkyl, optionally substituted alkenyloxy, optionally substituted alkinyloxy, halo-lower alkoxy, cycloalkoxy, cycloalkyl-lower alkoxy, lower alkoxy-lower alkoxy, heterocyclyloxy, heterocyclyl-lower alkoxy and halogen;

and wherein two adjacent substituents together with the atoms of aryl or heteroaryl may form a 5, 6 or 7 membered carbocyclic or heterocyclic ring;

$R^3$ represents phenyl substituted by one substituent selected from carboxy, lower alkoxycarbonyl, hydroxy-lower alkoxycarbonyl, lower alkoxy-lower alkoxycarbonyl, optionally substituted phenyl-lower alkoxycarbonyl, heteroaryl, heterocyclyl, a carbamoyl group $CONR^4R^5$, and a sulfamoyl group $SO_2NR^4R^5$, wherein such substituents on phenyl may be directly linked or linked via a spacer selected from lower alkylidene, oxygen, oxymethyl, nitrogen optionally substituted by lower alkyl, or aminomethyl wherein the amino nitrogen is optionally substituted by lower alkyl; and optionally one or two further substituents selected from lower alkyl, halo-lower alkyl, lower alkoxy-lower alkyl, lower alkoxy, lower alkoxy-lower alkoxy, and halo;

or phenyl substituted by one substituent selected from amino optionally substituted by one or two substituents selected from lower alkyl, hydroxyalkyl, alkoxyalkyl, aminoalkyl and optionally substituted alkylcarbonyl, and an aminocarbonylamino group NHCONR$^4$R$^5$, wherein such substituents on phenyl may be directly linked or linked via a lower alkylidene spacer; and optionally one or two further substituents selected from lower alkyl, halo-lower alkyl, lower alkoxy-lower alkyl, lower alkoxy, lower alkoxy-lower alkoxy, and halo;

or phenyl substituted by one substituent selected from cyano, cyanomethyl, sulfo, lower alkoxysulfonyl, hydroxy-lower alkoxysulfonyl, lower alkoxy-lower alkoxysulfonyl and optionally substituted phenyl-lower alkoxysulfonyl; and optionally one or two further substituents selected from lower alkyl, halo-lower alkyl, lower alkoxy-lower alkyl, lower alkoxy, lower alkoxy-lower alkoxy and halo;

or pyridyl, pyridazinyl, pyrimidinyl, pyrazinyl, quinolinyl or isoquinolinyl, each optionally substituted by one or two substituents selected from lower alkyl, halo-lower alkyl, lower alkoxy-lower alkyl, lower alkoxy, lower alkoxy-lower alkoxy, carboxy, lower alkoxycarbonyl, a carbamoyl group CONR$^4$R$^5$, a sulfamoyl group SO$_2$NR$^4$R$^5$, amino optionally substituted by one or two substituents selected from lower alkyl, hydroxyalkyl, alkoxyalkyl, aminoalkyl and optionally substituted alkylcarbonyl, an aminocarbonylamino group NHCONR$^4$R$^5$, cyano, and halo;

R$^4$ represents hydrogen, alkyl, cycloalkyl, cycloalkyl-alkyl, hydroxyalkyl, alkoxyalkyl, hydroxyalkoxyalkyl, alkoxyalkoxyalkyl, optionally substituted alkenyl, optionally substituted alkinyl, aminoalkyl, wherein the nitrogen can be substituted by up to two substituents selected from lower alkyl, cycloalkyl, cycloalkyl-lower alkyl, hydroxy-lower alkyl, lower alkoxy-lower alkyl, hydroxy-lower alkoxy-lower alkyl or lower alkoxy-lower alkoxy-lower alkyl; heterocyclyl, optionally substituted alkenyl, optionally substituted alkinyl, lower alkylcarbonyl or lower alkylsulfonyl;

R$^5$ represents hydrogen or lower alkyl;

or R$^4$ and R$^5$ together with the nitrogen they are bound to represent a five, six or seven membered heterocyclic ring that can be partially or fully unsaturated and may be optionally substituted by one or more substituents selected from oxo, lower alkyl, halo-lower alkyl, hydroxy-lower alkyl, lower alkoxy-lower alkyl or lower alkoxy;

and salts thereof.

Most preferred are the compounds of the Examples, especially the compounds of Examples 6, 55, 56, 57, 58, 60, 63, 64, 65, 68, 71, 76, 94, 100, 101 and 104 and salts thereof.

Especially, the invention relates to the use of a compound of formula (I), a prodrug or a pharmaceutically acceptable salt of such a compound for the preparation of a pharmaceutical composition for the treatment of a neoplastic disease, autoimmune disease, transplantation related pathology and/or degenerative disease.

Furthermore, the invention provides a method for the treatment of a neoplastic disease, autoimmune disease, transplantation related pathology and/or degenerative disease, which comprises administering a compound of formula (I), a prodrug or a pharmaceutically acceptable salt thereof, wherein the radicals and symbols have the meanings as defined above, in a quantity effective against said disease, to a warm-blooded animal requiring such treatment.

Method of Preparation

A compound of the invention may be prepared by processes that, though not applied hitherto for the new compounds of the present invention, are known per se, in particular A) for the preparation of a compound of formula (I) wherein R$^3$ is CH$_2$NR$^6$R$^7$, a process wherein an aldehyde of formula (II)

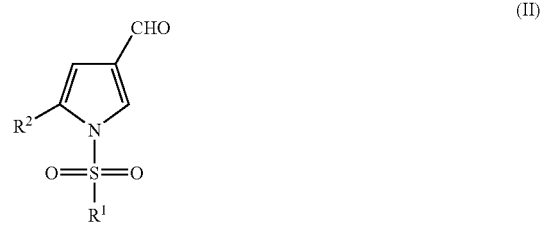

wherein R$^1$ and R$^2$ are as defined for a compound of formula (I), or a derivative thereof wherein functional groups are in protected form, is reacted with an amine of formula (III)

wherein R$^6$ and R$^7$ are as defined for a compound of formula (I), a salt thereof or a derivative thereof wherein functional groups are in protected form, in the presence of a reducing agent, optionally in the presence of an inert base and/or a suitable catalyst, and optionally in the presence of an inert solvent, and any protecting groups in a protected derivative of a compound of the formula (I) are removed; or B) for the preparation of a compound of formula (I) wherein R$^3$ is CH$_2$NR$^6$R$^7$, a process wherein a carboxamide of formula (IV)

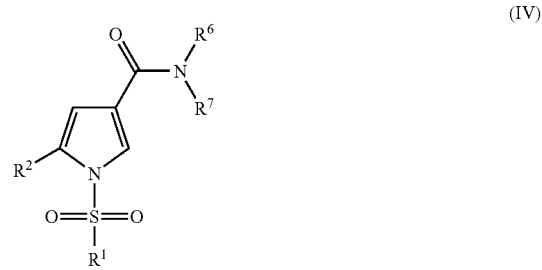

wherein R$^1$, R$^2$, R$^6$ and R$^7$ are as defined for a compound of formula (I), or a derivative thereof wherein functional groups are in protected form, is treated with a reducing agent, optionally in the presence of a suitable catalyst, and optionally in the presence of an inert solvent, and any protecting groups in a protected derivative of a compound of the formula (I) are removed;

C) for the preparation of a compound of formula (I) wherein R$^3$ is aryl or heteroaryl optionally substituted aryl or heteroaryl, a process wherein a compound of formula (V)

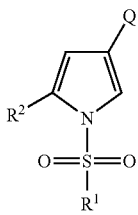

wherein R¹ and R² are as defined for a compound of formula (I) and Q is chlorine, bromine or iodine, or a derivative thereof wherein functional groups are in protected form, is reacted with a boronic acid of formula (VI)

R³—B(OH)₂ (VI)

wherein R³ is defined as for a compound of formula (I), an ester thereof, a salt thereof or a derivative thereof wherein functional groups are in protected form, in the presence of a suitable catalyst, and optionally in the presence of an inert solvent; and any protecting groups in a protected derivative of a compound of the formula (I) are removed; or D) for the preparation of a compound of formula (I) wherein R³ is optionally substituted aryl or heteroaryl, a process wherein a boronic acid of formula (VII)

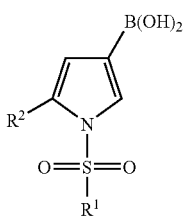

wherein R¹ and R² are as defined for a compound of formula (I), an ester thereof, a salt thereof or a derivative thereof wherein functional groups are in protected form, is reacted with a compound of formula (VII)

R³-Q (VII)

wherein R³ is defined as for a compound of formula (I) and Q is chlorine, bromine or iodine, an ester thereof, a salt thereof or a derivative thereof wherein functional groups are in protected form, in the presence of a suitable catalyst, and optionally in the presence of an inert solvent; and any protecting groups in a protected derivative of a compound of the formula (I) are removed;

E) for the preparation of a compound of formula (I) wherein R³ is optionally substituted aryl or heteroaryl, a process wherein a pyrrole of formula (IX)

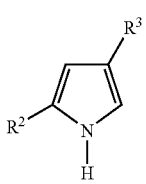

wherein R² and R³ are as defined for a compound of formula (I), is reacted with a sulfonic acid halide of formula (X)

R¹—SO₂-Q (X)

wherein R¹ is defined as for a compound of formula (I) and Q is chlorine or bromine, or a derivative thereof wherein functional groups are in protected form, in the presence of a suitable catalyst, and optionally in the presence of an inert solvent; and any protecting groups in a protected derivative of a compound of the formula (I) are removed;

and, if so desired, an obtainable compound of formula (I) is converted into another compound of formula (I), a free compound of formula (I) is converted into a salt, an obtainable salt of a compound of formula (I) is converted into the free compound or another salt, and/or a mixture of isomeric compounds of formula (I) is separated into the individual isomers.

The reaction of the pyrrolecarboxaldehyde of formula (II) with an amine of formula (III) is performed under customary reaction conditions used in reductive amination. For example, the carboxaldehyde of formula (II) is mixed with the amine of formula (III) in a pH range of about pH 3 to pH 6, for example in the presence of an organic acid such as acetic acid, and the imine formed in situ reduced with a metal hydride, for example a boron hydride, in particular sodium borohydride or, preferably, sodium cyanoborohydride or sodium triacetoxyborohydride. Alternatively the imine formed in situ may also be reduced by catalytic hydrogenation, e.g. with hydrogen gas under pressure in the presence of a suitable heterogeneous noble metal catalysts, such as palladium or platinum in suitable activated form, e.g. 10% palladium on carbon, or in the presence of a homogeneous hydrogenation catalyst.

The reaction can be carried out in a manner known per se, usually in the presence of a suitable solvent, e.g. a polar solvent such as methanol or a dipolar aprotic solvent such as dimethyl formamide or the like, with cooling or heating, for example in a temperature range from approximately −30° C. to approximately +150° C., especially approximately around room temperature.

The reduction of the compound of formula (IV) is performed under customary reaction conditions used in amide reduction. Suitable reducing agents are e.g. a metal hydride, for example a boron hydride, also sodium borohydride in the presence of an activating catalyst such as triethyloxonium tetrafluoroborate, cobalt chloride or trifluoroacetic acid, or preferably an aluminium hydride, in particular lithium aluminium hydride, or a partially alkoxylated lithium aluminium hydride, e.g. lithium trimethoxyaluminium hydride or lithium tert-butoxyaluminium hydride. Alternatively the amide may also be reduced by trichlorosilane.

The reaction can be carried out in a manner known per se, usually in the presence of a suitable solvent, e.g. an ether, such as diethyl ether or tetrahydrofuran. Sodium borohydride reduction is preferably conducted in an alcohol, such as ethanol. The reaction may be performed with cooling or heating, for example in a temperature range from approximately −30° C. to approximately +150° C., especially approximately around room temperature.

The reaction of a bromo or iodo substituted pyrrole of formula (V) with a suitable boronic acid of formula (VI) or the a corresponding boronic acid ester is known as Suzuki reaction, and is preferably executed under conditions known per se for a Suzuki reaction. Likewise the reaction of a pyrrole boronic acid of formula (VII) or the corresponding boronic acid ester, e.g. the cyclic ester with 2,2-dimethylpropane-1, 3-diol, with the corresponding halide of formula (VII) is performed. Preferably a dipolar aprotic solvent such as dimethyl formamide, or a polar ether, e.g. dioxane, tetrahydrofuran or dimethoxyethane, is used, and the reaction is performed with moderate heating, for example in a temperature range from approximately +30° C. to approximately +1 50° C., especially approximately around 40° C. to 80° C., in the presence of a soluble palladium(0) or related metal catalyst, for example tetrakis(triphenylphosphine)palladium. Alternatively, the reaction may also be performed with a compound of formula (V) or (VIII) wherein Q is chlorine. Further catalysts considered are tetrakis(trimethoxyphosphine)palladium, tris(dibenzylideneacetone)-palladium or dichlorobis(triphenylphosphine)palladium(II), and also nickel catalysts, e.g. dichlorobis(triethylamine)nickel(II). The reaction is preferably performed in the presence of a base, e.g. solid or aqueous sodium or potassium carbonate, potassium hydroxide or potassium phosphate.

The pyrrole of formula (IX) may be sulfonylated with a sulfonyl chloride or bromide of formula (X) in the presence of a base, preferably a tertiary amine, e.g. dimethylaniline or diethylisopropylamine.

If one or more other functional groups, for example carboxy, hydroxy or amino, are or need to be protected in a compound of formulas (II), (III), (IV), (V), (VI), (VII), (VIII), (IX) and (X), because they should not take part in the reaction, these are such protecting groups as are usually applied in the synthesis of amides, in particular peptide compounds, cephalosporins, penicillins, nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference books for peptide synthesis and in special books on protective groups such as J. F. W. McOmie, "Protective Groups in Organic Chemistry", Plenum Press, London and New York 1973, in "Methoden der organischen Chemie" (Methods of organic chemistry), Houben-Weyl, 4th edition, Volume 15/I, Georg Thieme Verlag, Stuttgart 1974, and in T. W. Greene, "Protective Groups in Organic Synthesis", Wiley, New York.

In the additional process steps, carried out as desired, functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

In the conversion of an obtainable compound of formula (I) into another compound of formula (I), an amino group may be alkylated or acylated to give the correspondingly substituted compounds. Alkylation may be performed with an alkyl halide or an activated alkyl ester. For methylation, diazomethane may be used. Alkylation may also be performed with an aldehyde under reducing conditions. For acylation the corresponding acyl chloride is preferred. Alternatively, an acid anhydride may be used, or acylation may be accomplished with the free acid under conditions used for amide formation known per se in peptide chemistry, e.g. with activating agents for the carboxy group, such as 1-hydroxybenzotriazole, optionally in the presence of suitable catalysts or co-reagents.

Reduction of a nitro group in an nitro-substituted aryl or heteroaryl group to give the corresponding amino group is done, e.g., with iron powder in alcohol or with other reducing agents.

A carboxy group in a carboxy-substituted aryl or heteroaryl group may be amidated under conditions used for amide formation known per se in peptide chemistry, e.g. with the corresponding amine and an activating agent for the carboxy group, such as 1-hydroxy-benzotriazole, optionally in the presence of suitable catalysts or co-reagents.

A bromo or iodo substituent in an aryl or heteroaryl group may be replaced by phenyl or a phenyl derivative by reaction with a suitable phenylboronic acid in a Suzuki reaction, preferably in a dipolar aprotic solvent such as dimethyl formamide, or in a polar ether, e.g. tetrahydrofuran or dimethoxyethane, in the presence of a soluble palladium(0) or related metal catalyst, for example tetrakis(triphenylphosphine)palladium.

Salts of a compound of formula (I) with a salt-forming group may be prepared in a manner known per se. Acid addition salts of compounds of formula (I) may thus be obtained by treatment with an acid or with a suitable anion exchange reagent.

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

It should be emphasized that reactions analogous to the conversions mentioned in this chapter may also take place at the level of appropriate intermediates.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example ion exchangers, typically cation exchangers, for example in the H$^+$ form, depending on the type of reaction and/or reactants at reduced, normal, or elevated temperature, for example in the range from −100° C. to about 190° C., preferably from about −80° C. to about 150° C., for example at −80 to +60° C., at −20 to +40° C., at room temperature, or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and further processes the said compound in situ. In the preferred embodiment, one starts from those starting materials which lead to the compounds described hereinabove as preferred, particularly as especially preferred, primarily preferred, and/or preferred above all.

In the preferred embodiment, a compound of formula (I) is prepared according to or in analogy to the processes and process steps defined in the Examples.

The compounds of formula (I), including their salts, are also obtainable in the form of hydrates, or their crystals can include for example the solvent used for crystallization, i.e. be present as solvates.

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of formula (II), (III), (IV), (V), (VI), (VII), (VIII), (IX) or (X) are known, commercially available, or can be synthesized in analogy to or according to methods that are known in the art. For example, pyrrolecarboxaldehydes of formula (II) are prepared by reaction of the corresponding 3-halopyrrole of formula (V), wherein $R^1$ and $R^2$ are as defined for a compound of formula (I) and Q is chlorine, bromine or iodine, or a derivative thereof wherein functional groups are in protected form, first with butyllithium to form the corresponding metallated pyrrole of formula (V) wherein Q represents lithium, and then with dimethylformamide or another suitable formamide, preferably in the presence of a suitable inert solvent and/or of an excess of the reagent dimethylformamide.

Compounds of formula (V) are known or can be synthesized in analogy to the reaction conditions described in Th. Masquelin and D. Obrecht, Synthesis 1995, 276.

Amides of formula (IV) are prepared by reaction of corresponding pyrrolecarboxylic acid of formula (XI)

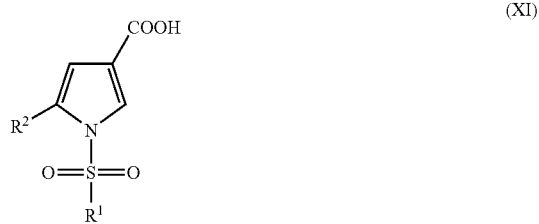

(XI)

or of an activated derivative thereof with an amine of formula (III). Preferred reaction conditions are those of amide formation known in peptide chemistry, for example using a carbodiimide derivative, a suitable hydroxyimide, 1-hydroxybenztriazole or the like as condensing agent.

Compounds of formula (XI) are known or can be synthesized in analogy to known reactions, for example by reaction of the 3-halopyrrole compound of formula (V) with butyllithium followed by carboxylation with carbon dioxide.

Boronic acid derivatives of formula (VI) and (VII) are known or may be synthesized from the corresponding halides by reaction with butyllithium followed by tri-isopropoxyborate and hydrolysis, or from corresponding halides and diborates in the presence of a suitable palladium catalyst. For example the cyclic boronic acid neopentylglycol ester is formed from the corresponding bromide with bis(2,2-dimethylpropane-1,3-dioxy)diboron in the presence of dichloro[1,1'bis(diphenylphosphino)ferrocene]palladium.

Pyrroles of formula (IX) and sulfonic acid derivatives of formula (X) are known or may be synthesized in analogy to known reactions.

Pharmaceutical Preparations, Methods, and Uses

The present invention relates also to pharmaceutical compositions that comprise a compound of formula (I) as active ingredient and that can be used especially in the treatment of the diseases mentioned at the beginning. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention relates especially to pharmaceutical compositions that comprise a compound of formula (I), a tautomer, a prodrug or a pharmaceutically acceptable salt, or a hydrate or solvate thereof, and at least one pharmaceutically acceptable carrier.

The invention relates also to pharmaceutical compositions for use in a method for the prophylactic or especially therapeutic management of the human or animal body, in particular in a method of treating neoplastic disease, autoimmune disease, transplantation related pathology and/or degenerative disease, especially those mentioned hereinabove.

The invention relates also to processes and to the use of compounds of formula (I) thereof for the preparation of pharmaceutical preparations which comprise compounds of formula (I) as active component (active ingredient).

A pharmaceutical composition for the prophylactic or especially therapeutic management of a neoplastic disease, autoimmune disease, transplantation related pathology and/ or degenerative disease, of a warm-blooded animal, especially a human or a commercially useful mammal requiring such treatment, comprising a novel compound of formula (I) as active ingredient in a quantity that is prophylactically or especially therapeutically active against the said diseases, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, lipsticks, drops, sprays, dispersions, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinyl-pyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropyl-methylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxy-ethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The present invention relates furthermore to a method for the treatment of a neoplastic disease, autoimmune disease, transplantation related pathology and/or degenerative disease, which comprises administering a compound of formula (I) or a pharmaceutically acceptable salt thereof, wherein the radicals and symbols have the meanings as defined above for formula (I), in a quantity effective against said disease, to a warm-blooded animal requiring such treatment. The compounds of formula (I) can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.05 g to approximately 5 g, preferably from approximately 0.25 g to approximately 1.5 g, of a compound of the present invention.

The present invention relates especially also to the use of a compound of formula (I), or a pharmaceutically acceptable salt thereof, especially a compound of formula (I) which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, in particular a neoplastic disease, autoimmune disease, transplantation related pathology and/or degenerative disease.

The preferred dose quantity, composition, and preparation of pharmaceutical formulations (medicines) which are to be used in each case are described above.

The following Examples serve to illustrate the invention without limiting the invention in its scope.

EXAMPLES

Abbreviations: DMF=dimethyl formamide; DMSO=dimethyl sulfoxide; HMPA=hexamethylphosphoric acid amide; THF=tetrahydrofuran; eq.=equivalent(s); h=hour; min=minutes; MS=mass spectrum; r.t.=room temperature; RT=retention time in minutes;

Analytical HPLC retention times (RT, in minutes) were determined using a Develosil RP Aqueous 4.6×50 mm column No. 1610101 (Phenomenex) with the following gradients:

program 1: 10% $CH_3CN$; 90% $H_2O$+0.1% trifluoroacetic acid; flow 1.5 ml/min for 2 min; within 5 min to 100% $CH_3CN$;

program 2: 20% $CH_3CN$; 80% $H_2O$+0.1% trifluoroacetic acid; flow 1.5 ml/min for 2 min; within 5 min to 100% $CH_3CN$;

program 3: 30% CH$_3$CN; 70% H$_2$O+0.1% trifluoroacetic acid; flow 1.5 ml/min for 2 min; within 5 min to 100% CH$_3$CN;

program 4: 40% CH$_3$CN; 60% H$_2$O+6.1% trifluoroacetic acid; flow 1.5 ml/min for 2 min; within 5 min to 100% CH$_3$CN;

program 5: 60% CH$_3$CN; 40% H$_2$O+0.1% trifluoroacetic acid; flow 1.5 ml/min for 2 min; within 5 min to 100% CH$_3$CN.

program 6: 5% CH$_3$CN; 95% H$_2$O+0.1% trifluoroacetic acid; flow 1.5 ml/min for 2 min; within 5 min to 100% CH$_3$CN.

program 7: 15% CH$_3$CN; 85% H$_2$O+0.1% trifluoroacetic acid; flow 1.5 ml/min for 2 min; within 5 min to 100% CH$_3$CN.

program 8: 50% CH$_3$CN; 50% H$_2$O+0.1% trifluoroacetic acid; flow 1.5 ml/min for 2 min; within 5 min to 100% CH$_3$CN.

Example 1

4(N-2,4-Dimethoxyphenyl-N-ethylaminomethyl)-2-(2-thienyl)-1-(p-toluene-sulfonyl)-pyrrole 2-(2-Thienyl)-1-(p-toluenesulfonyl)pyrrole-4-carboxaldehyde (80 mg, 0.24 mmol) is dissolved in THF (2 ml). A solution of 1 M acetic acid in THF and 2,4-dimethoxy-N-ethyl-aniline (71 μl, 0.48 mmol) are added and stirred at r.t. for 15 min. Then NaBH(OAc)$_3$ (153 mg, 0.72 mmol) is added and the solution stirred at r.t. for 12 h. The solution is partitioned between methylene chloride and aqueous sodium bicarbonate. The organic phase is filtered over a pad of celite/MgSO$_4$ and finally purified by preparative HPLC. RT (program 3) 3.35. MS: 467.0.

Example 1a 2-(2-Thienyl)-1-(p-toluenesulfonyl)pyrrole-4-carboxaldehyde

A butyllithium solution in pentane (1.7 M, 23.1 ml, 39.3 mmol) is added dropwise at −78° C. to a solution of 4-bromo-2-(2-thienyl)-1-p-toluenesulfonyl)-pyrrole (12.0 g, 31.4 mmol) [T. Masquelin and D. Obrecht, Synthesis 1995, 276-284] in dry diethyl ether (160 ml). The mixture is stirred for 15 min at −75° C. A solution of DMF (12.2 ml, 157 mmol) in dry diethyl ether (140 ml) is added dropwise. The mixture is stirred at −78° C. for 2.5 h, then warmed to 0° C. and poured into a mixture of 1 N HCl (200 ml) and ethyl acetate (600 ml). The organic layer is separated and the aqueous layer extracted with ethyl acetate. The combined organic layers are washed (sat. aq. NaHCO$_3$, sat aq. NaCl), dried (Na$_2$SO$_4$), filtered and evaporated. Flash chromatography (hexane/ethyl acetate 1:4) yields the pure aldehyde. MS: 332.0.

Example 2

4-(N-[3-Dimethylaminopropyl]-aminomethyl)-2-(3, 4-methylenedioxyphenyl)-1-(p-toluenesulfonyl)-pyrrole 2-(3,4-Methylenedioxyphenyl)-1-(p-toluenesulfonyl)-pyrrole-4-carboxaldehyde (80 mg, 0.22 mmol, prepared analogously to Example 1a) is dissolved in THF (2 ml). A solution of 1 M acetic acid in THF and 3-dimethylamino-1-propylamine (54 μl, 0.44 mmol) are added and stirred at r.t. for 15 min. Then NaBH(OAc)$_3$ (138 mg, 0.66 mmol) is added and the solution stirred at r.t. for 12 h. The solution is extracted with CH$_2$Cl$_2$/sat. NaHCO$_3$, filtered over a celite/MgSO$_4$ pad and purified by preparative HPLC. RT: 3.6, MS: 456.1.

For the preparation of the dihydrochloride, this diamine (40 mg, 87.7 μmol) in 1 ml ethanol is treated with 10 drops of 4 M HCl in dioxane. The mixture is evaporated under reduced pressure. The residue is suspended in ethanol/ethyl acetate (1:10), filtered and dried to give the dihydrochloride of the title compound as a colorless crystalline solid.

Example 3

4-(N-[3-{4-Methylpiperazinyl}-1-propyl]-aminomethyl-1-(p-toluenesulfonyl)-2-(3,4,5-trimethoxyphenyl)-pyrrole 1-(p-Toluenesulfonyl)-2-(3,4,5-trimethoxyphenyl)-pyrrole-4-carboxaldehyde and 1-(3-aminopropyl)-4-methylpiperazine are condensed and reduced with NaBH(OAc)$_3$ following the procedure of Example 2. HPLC: RT (program 1) 2.93, MS: 557.0.

$^1$H-NMR: (DMSO-d$_6$, 300 MHz): 7.53-7.26 (m, 5H), 6.39 (s, 2H), 6.24 (s, 1H), 3.71 (s, 3H), 3.69 (s, 6H), 3.48 (br.s, 2H), 2.50 (m, 2H), 2.34 (s, 3H), 2.30-2.25 (m, 10H), 2.12 (s, 3H), 2.02 (br.s, 1H), 1.53 (m, 2H).

Example 3a 1-(p-Toluenesulfonyl)-2-(3,4,5-trimethoxyphenyl)-pyrrole-4-carboxaldehyde To a stirred solution of 4-bromo-1-(p-toluenesulfonyl)-2-(3,4,5-trimethoxyphenyl)-pyrrole (2.33 g, 5.0 mmol) in dry ethyl ether (20 ml), a tert-butyl lithium solution (3.82 ml, 1.3 equiv., 1.7 M in pentane) is added at −78° C. The reaction mixture is stirred for 15 min at −78° C. DMF (1.93 ml, 5 equiv.) is added, and stirring continued at −78° C. for 2 h. The reaction mixture is slowly brought to 4° C., quenched with cooled aqueous 1 N HCl solution and ethyl acetate. The organic layer is extracted with brine, dried over MgSO$_4$, the solvents evaporated and the residue chromatographed with gradients of hexane/ethyl acetate (2:1 to 1:1) to yield the title compound as a greenish solid. $^1$H-NMR (300 MHz, CDCl$_3$): 9.9 (s, 1H); 8.13 (d, J=2.0 Hz, 1H); 7.3-7.1 (m, 4H); 6.57 (d, J=2.0 Hz, 1H); 3.36 (s, 2H); 6.36 (s, 2H); 3.92 (s, 3H); 3.76 (s, 6H); 2.39 (s, 3H).

Example 3b

4-Bromo-1-(p-toluenesulfonyl)-2-(3,4,5-trimethoxyphenyl)-pyrrole

To a stirred solution of 3-(p-toluenesulfonylamino)-1-propinyl 3,4,5-trimethoxyphenyl ketone (4.03 g, 10.0 mmol) in CH$_2$Cl$_2$ (40 ml), a 33% HBr/acetic acid solution (2.63 ml, 15.0 mmol) is added dropwise at 4° C. within 10 min. The reaction mixture is stirred for 1 h at 40° C. and extracted with CH$_2$Cl$_2$ and aqueous 1 N HCl solution. The organic layer is dried over MgSO$_4$, the solvents evaporated, and the residue chromatographed on SiO$_2$ with gradients of hexane/ethyl acetate (4:1 to 3:1) to yield the title compound as a greyish solid. $^1$H-NMR (300 MHz, CDCl$_3$): 7.49 (d, J=2.0 Hz, 1H);

7.3-7.2; 7.2-7.1 (2m, 4H); 6.38 (s, 2H); 6.17 (d, J=2.0 Hz, 1H); 3.92 (s, 3H); 3.77 (s, 6H); 2.38 (s, 3H).

Example 3c 3-(p-Toluenesulfonylamino)-1-propinyl 3,4,5-trimethoxyphenyl ketone To a stirred solution of propargyl p-toluenesulfonamide (2.09 g, 10.0 mmol) in dry THF (30 ml) and HMPA (5 ml), a 2 M solution of lithium diisopropylamide in THF (11.0 ml, 22.0 mmol) is added under argon at −78° C. The reaction mixture is stirred for 2 h at −78° C. 3,4,5-Trimethoxybenzaldehyde (13.0 mmol, 1.3 equiv.) is added, and the reaction mixture stirred for 30 min at −78° C., slowly brought to 4° C., stirred for an additional hour at 4° C., and poured onto a mixture of aqueous 1 N HCl solution, ice and ethyl acetate. The organic layer is dried over $MgSO_4$, the solvents evaporated and the residue chromatographed on $SiO_2$ with gradients of hexane/ethyl acetate (1:1 to 1:3) to yield the intermediate alcohol as a pale yellow oil. This oil is dissolved in $CH_2Cl_2$ (20 ml) and slowly added to a stirred suspension of $MnO_2$ (26 g, 30 equiv.) in $CH_2Cl_2$ (120 ml) at 4° C. The reaction mixture is stirred for 30 min at 4° C., filtered over a plug of $MgSO_4$, and the filtrate evaporated. The residue is dried under reduced pressure and the resulting solids suspended in hexane/ethyl acetate (1:8), filtered and dried to yield the title compound as beige solid. $^1$H-NMR (300 MHz, $CDCl_3$): 7.85-7.75; 7.4-7.25 (2m, 6H); 5.0-4.95 (m, 1H); 4.11 (d, J=6.2 Hz, 2H); 3.96 (s, 3H); 3.94 (s, 6H); 2.35 (s, 3H).

Example 4

1-(m-Chlorobenzenesulfonyl)-2-(3,4-methylenedioxyphenyl)-4-(N-[3-{4-methylpiperazinyl}-propyl]-aminomethyl)-pyrrole 1-(m-Chlorobenzensulfonyl)2-(3,4methylenedioxyphenyl)-pyrrole-4-carboxaldehyde and 1-(3-aminopropyl)-4-methylpiperazine are condensed and reduced with NaBH(OAc)$_3$ following the procedure of Example 2. HPLC: RT (program 1) 3.26, MS: 531.0.

Example 4a 1-(m-Chlorobenzenesulfonyl)-2-(3,4-methylenedioxyphenyl)-pyrrole-4-carboxaldehyde The title compound is prepared from 4-bromo-1-(m-chlorobenzensulfonyl)-2-(3,4-methylenedioxyphenyl)-pyrrole, tert-butyl lithium and DMF following the procedure of Example 3a. $^1$H-NMR (300 MHz, $CDCl_3$): 9.89 (s, 1H); 8.08 (d, J=2.0 Hz, 1H); 7.6-7.5 (m, 1H); 7.4-7.25 (m, 4H); 6.8-6.7 (m, 1H); 6.65-6.55 (m, 1H); 6.55 (d, J=2.0, 1H); 6.05 (s, 2H).

Example 4b

4-Bromo-1-(m-chlorobenzensulfonyl)-2-(3,4-methylenedioxyphenyl)-pyrrole

The title compound is prepared from 3-(m-chlorobenzenesulfonylamino)-1-propinyl 3,4-methylenedioxyphenyl ketone and HBr in acetic acid following the procedure of Example 3b. $^1$H-NMR (300 MHz, $CDCl_3$): 7.6-7.5 (m, 1H); 7.54 (d, J=2.0 Hz, 1H); 7.4-7.3 (m, 3H); 6.8-6.7 (m, 1H); 6.7-6.6 (m, 2H); 6.16 (d, J=2.0 Hz, 1H); 6.05 (s, 2H).

Example 4c 3-(m-Chlorobenzenesulfonylamino)-1-propinyl 3,4-methylenedioxyphenyl ketone The title compound is prepared from lithiated propargyl m-chlorobenzenesulfonamide and 3,4-methylendioxybenzaldehyde followed by oxidation with $MnO_2$ following the procedure of Example 3c. $^1$H-NMR (300 MHz, $CDCl_3$): 7.94 (~s, 1H); 7.9-7.8; 7.6-7.35 (2 m, 5H); 6.9-6.8 (m, 1H); 6.10 (s, 2H); 5.1-4.95 (br.m, H); 4.20 (d, J=6.2 Hz, 2H).

Example 4d

Propargyl m-chlorobenzenesulfonamide

To a stirred solution of propargylamine (0.78 ml, 12.0 mmol) and pyridine (3.0 ml) in $CH_2Cl_2$ (30 ml), 4-dimethylaminopyridine (122 mg, 1.0 mmol) and a solution of m-chlorobenzenesulfonyl chloride (2.11 g, 10.0 mmol) in $CH_2Cl_2$ are added at 4° C. The reaction mixture is stirred for 30 min at 4° C. and for 12 h at room temperature. The reaction mixture is extracted with $CH_2Cl_2$ and aqueous 1 N HCl solution, the organic layer dried over $MgSO_4$, the solvents evaporated and the solid residue suspended in a mixture of hexane/ethyl acetate (1:8), filtered and dried under reduced pressure to yield the title compound as beige solid. $^1$H-NMR (300 MHz, $CDCl_3$): 7.95-7.9; 7.9-7.75; 7.65-45 (3m, 4H); 4.85 (br.s, 1H); 3.95-3.9 (m, 2H); 2.14 (t, J=2.5 Hz, 1H).

Example 5 p-(1-[m-chlorobenzenesulfonyl]-2-[3,4-methylenedioxyphenyl]-4pyrrolyl)-benzamide A mixture of 1-(m-chlorobenzensulfonyl)-2-(3,4-methylenedioxyphenyl)-pyrrole-4-boronic acid 2,2-dimethylpropane-1,3-diyl ester (100 mg, 0.2 mmol), p-bromobenzamide (0.18 mmol), $K_3PO_4$ (145 mg, 0.7 mmol), and tetrakis(triphenylphosphine)palladium(0) (30 mg) is dried in vacuo for 15 min. 1,2-Dimethoxyethane (2.5 ml) is added under argon atmosphere, and the mixture is stirred at 80° C. for 16 h, then cooled to r.t. and extracted with ethyl acetate and half saturated aqueous $NaHCO_3$ solution. The organic layer is dried over $Na_2SO_4$ and concentrated. The crude residue is purified by chromatography with hexane/ethyl acetate to yield the pure title compound.

HPLC: RT (program 1) 4.86. MS: 481.0. $^1$H NMR: (DMSO-d$_6$, 300 MHz): 8.10 (d, J=1.9 Hz, 1H), 7.96 (br. s, 1H), 7.89 (d, J=8.5 Hz, 2H), 7.80-7.77 (m, 3H), 7.68-7.50 (m, 3H), 7.43 (t, J=1.8 Hz, 1H), 7.42 (br s, 1H), 6.93 (d, J=8.0 Hz, 1H), 6.83 (d, J=1.9 Hz, 1H), 6.77 (d, J=1.6 Hz, 1H), 6.68 (dd, J=1.7 and 8.0 Hz, 1H), 6.10 (s, 2H).

Example 5a 1-(m-Chlorobenzensulfonyl)-2-(3,4-methylenedioxyphenyl)-pyrrole-4-boronic acid 2,2-dimethylpropane-1,3-diyl ester A mixture of 4-bromo-1-(m-chlorobenzensulfonyl)-2-(3,4-methylenedioxyphenyl)-pyrrole (Example 4b, 2.20 g, 5.0 mmol), bis(2,2-dimethylpropane-1,3-dioxy)diboron (2.26 g, 10.0 mmol), potassium acetate (2.94 g, 30.0 mmol) and-dichloro[1,1'-bis(diphenylphosphino)-ferrocene]palladium (Pd(dppf)Cl$_2$×CH$_2$Cl$_2$, 408 mg, 0.5 mmol) is dried for 1 h at high vacuum. Degassed dioxane (25 ml) is added, and the reaction mixture stirred for 24 h at 80° C., cooled to room temperature and extracted with brine, water and ethyl acetate. The organic layer is dried over $MgSO_4$, the solvents evaporated and the residue chromatographed on deactivated $SiO_2$ (treated with a 5% solution of triethylamine in diethyl ether)

with gradients of ethyl acetate/hexane (1:3 to 1:1 to 3:1) to yield the title compound as a colourless foam. $^1$H-NMR (300 MHz, DMSO-$d_6$): 7.8-7.75 (m, 1H); 7.67 (d, J=2.0 Hz, 1H); 7.6-7.5 (m, 1H); 7.5-7.4 (m, 1H); 7.35-7.25 (m, 1H); 6.9-6.85 (m, 1H); 6.65 (s, 2H); 6.5-6.45 (m, 1H); 6.27 (d, J=2.0, 1H); 6.08 (s, 2H); 3.69 (s, 4H); 0.94 (s, 6H).

Example 6 p-(1-[p-Toluenesulfonyl]-2-[3,4,5-trimethoxyphenyl]-4-pyrrolyl)-benzamide 1-(p-Toluenesulfonyl)-2-(3,4,5-trimethoxyphenyl)-pyrrole-4-boronic acid 2,2-dimethyl-propane-1,3-diyl ester is reacted with p-bromobenzamide in the presence of $K_3PO_4$ and tetrakis(triphenylphosphine)palladium(0), following the procedure of Example 5.

HPLC: RT (program 1) 4.58, MS: 482.0.

Example 6a 1-(p-Toluenesulfonyl)-2-(3,4,5-trimethoxyphenyl)-pyrrole-4-boronic acid 2,2-dimethylpropane-1,3-diyl ester 4-Bromo-1-(p-toluenesulfonyl)-2-(3,4,5-trimethoxyphenyl)-pyrrole (Example 3b) is treated with bis(2,2-dimethylpropane-1,3-dioxy)diboron in the presence of Pd(dppf)C$_2$× CH$_2$Cl$_2$ following the procedure of Example 5a. $^1$H-NMR (300 MHz, DMSO-$d_6$): 7.61 (d, J=2.0 Hz, 1H); 7.29 (s, 4H); 6.35 (s, 2H); 6.31 (d, J=2.0, 1H); 3.71 (s, 4H); 3.68 (s, 3H); 3.66 (s, 2×3H); 2.34 (s, 3H); 0.95 (s, 6H).

The following compounds are synthesised according to Example 1

TABLE 1

| No. | $R^6$ | $R^7$ | Salt | HPLC: RT (program) | MS |
|---|---|---|---|---|---|
| 7 | phenyl-CH$_2$CH$_2$— | H | — | 4.08 (6) | 437.0 |
| 8 | CH$_3$O-phenyl-CH$_2$CH$_2$— | H | — | 3.35 (3) | 367.0 |
| 9 | morpholino-phenyl- | H | — | 3.24 (3) | 494.0 |

The following compounds are synthesised according to Example 2:

TABLE 2

| No. | $R^6$ | $R^7$ | Salt | HPLC: RT (program) | MS |
|---|---|---|---|---|---|
| 10 | phenyl-CH$_2$CH$_2$CH$_2$— | H | — | 3.47 (3) | 489.0 |
| 11 | CH$_3$O-phenyl-CH$_2$CH$_2$— | H | — | 3.34 (3) | 505.0 |

TABLE 2-continued

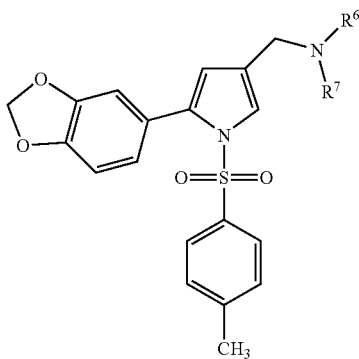

| No. | R⁶ | R⁷ | Salt | HPLC: RT (program) | MS |
|---|---|---|---|---|---|
| 12 | 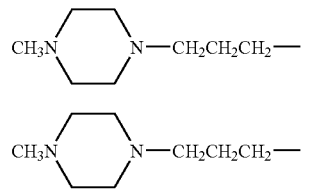 CH₃N⟨piperazine⟩N—CH₂CH₂CH₂— | H | — | 3.57 (6) | 511.0 |
| 13 | CH₃N⟨piperazine⟩N—CH₂CH₂CH₂— | H | 2 HCl | 3.10 (2) | 511.0 |
| 14 | 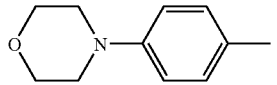 O⟨morpholine⟩N—C₆H₄—CH₃ | H | HCl | 3.84 (2) | 532.0 |
| 15 | CH₃CH₂N⟨piperazine⟩N—CH₂CH₂— | H | — | 3.53 (1) | 511.1 |
| 16 | 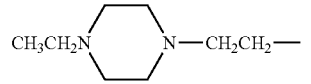 PhCH₂—N⟨piperazine⟩N—CH₂CH₂— | H | — | 3.33 (1) | 573.1 |
| 17 | 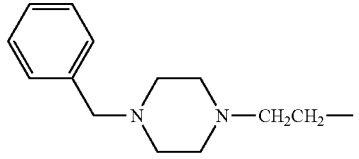 pyrrolidine-N—CH₂CH₂— | H | — | 3.12 (1) | 468.0 |
| 18 | 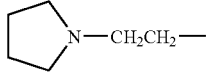 piperidine-N—CH₂CH₂— | H | — | 3.17 (1) | 482.0 |
| 19 | (CH₃CH₂)₂NCH₂CH₂— | CH₃ | — | 3.17 (1) | 484.0 |
| 20 | (CH₃CH₂)₂NCH₂CH₂— | H | — | 3.15 (1) | 470.0 |
| 21 | 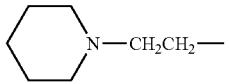 (N-ethylpyrrolidin-2-yl)CH₂— | H | — | 3.13 (1) | 482.0 |
| 22 | 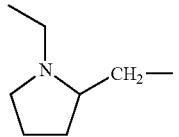 pyrrolidine-N—CH₂CH₂CH₂— | H | — | 3.13 (2) | 482.0 |
| 23 | 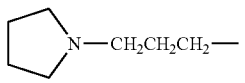 PhCH₂—N⟨piperazine⟩N—CH₂CH₂CH₂— | H | — | 3.17 (2) | 587.1 |

TABLE 2-continued
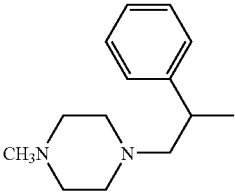
| No. | R⁶ | R⁷ | Salt | HPLC: RT (program) | MS |
|---|---|---|---|---|---|
| 24 | 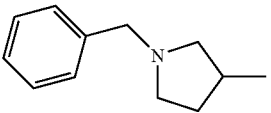 | H | — | 3.33 (2) | 573.1 |
| 25 |  | CH₃ | — | 3.39 (2) | 544.0 |
| 26 | 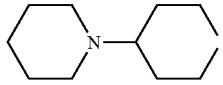 | CH₃ | — | 3.05 (2) | 482.0 |
| 27 | 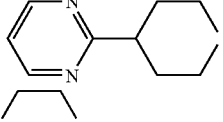 | | — | 3.13 (2) | 522.0 |
| 28 | 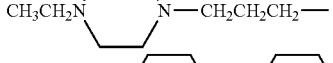 | | — | 3.71 (2) | 518.0 |
| 29 | CH₃CH₂N⟩N—CH₂CH₂CH₂— | H | — | 3.00 (2) | 525.1 |
| 30 | 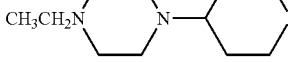 | | — | 3.06 (2) | 551.1 |
| 31 | (CH₃)₂NCH₂CH₂— | CH₃ | — | 3.50 (2) | 456.0 |
| 32 | 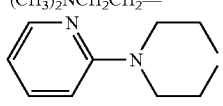 | | — | 3.23 (2) | 517.0 |
| 33 | 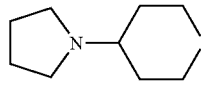 | | — | 3.12 (2) | 508.0 |
| 34 | (CH₃CH₂)₂NCH₂CH₂CH₂— | H | — | 3.14 (2) | 484.0 |
| 35 | (CH₃)₂N | | — | 3.50 (2) | 511.1 |
| 36 | 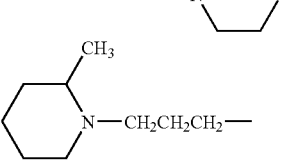 | H | — | 3.59 (2) | 510.0 |

TABLE 2-continued
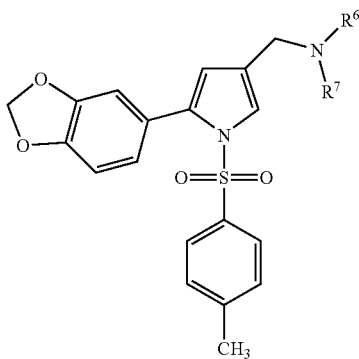
| No. | R⁶ | R⁷ | Salt | HPLC: RT (program) | MS |
|---|---|---|---|---|---|
| 37 | 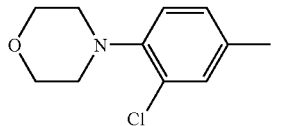 | H | — | 3.59 (2) | 559.1 |
| 38 | 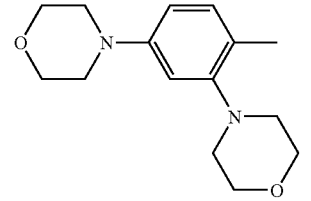 | H | — | 3.93 (4) | 566.0 |
| 39 | 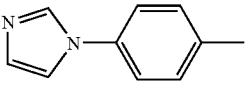 | H | — | 3.94 (2) | 617.1 |
| 40 | 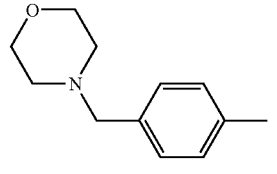 | H | — | 3.43 (3) | 513.0 |
| 41 | 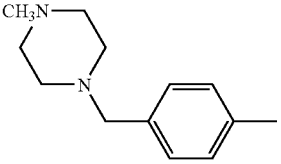 | H | — | 3.36 (3) | 546.0 |
| 42 | 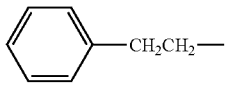 | H | — | 3.42 (1) | 559.0 |
| 43 | 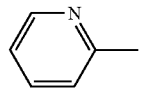 | H | — | 4.33 (6) | 475.0 |
| 44 |  | H | — | 2.98 (3) | 448.0 |

TABLE 2-continued
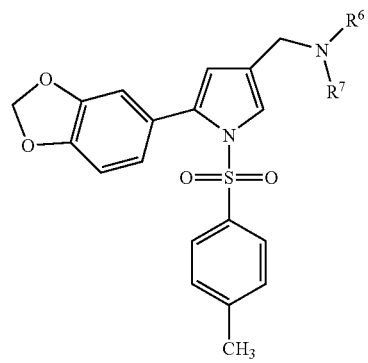
| No. | R6 | R7 | Salt | HPLC: RT (program) | MS |
|---|---|---|---|---|---|
| 45 | H2N-SO2-C6H4-CH3 | H | — | 4.76 (1) | 526.0 |
The following compounds are prepared according to Example 5
TABLE 3
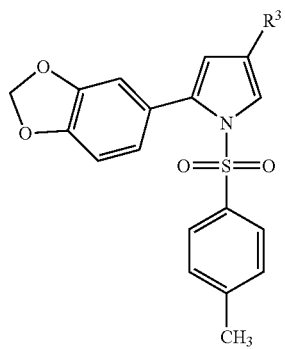
| No. | R3 | Salt | HPLC: RT (program) | MS |
|---|---|---|---|---|
| 46 | pyrimidin-5-yl | — | 4.34 (3) | 420.2 |
| 47 | 4-(H2N-CO)-C6H4- | — | 4.45 (3) | 461.0 |
| 48 | 4-NC-C6H4- | — | 3.80 (5) | 443.0 |
TABLE 3-continued
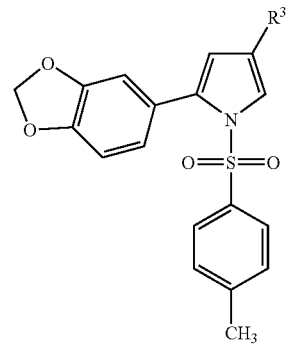
| No. | R3 | Salt | HPLC: RT (program) | MS |
|---|---|---|---|---|
| 49 | pyridin-3-yl | — | 3.23 (3) | 418.9 |
| 50 | 5-(H2N-CO)-pyridin-3-yl | — | 4.52 (6) | 461.9 |
| 51 | 4-(H2N-SO2)-C6H4- | — | 4.04 (3) | 497.0 |

The following compounds are prepared according to Example 5

TABLE 4

[Structure: 2-(thiophen-2-yl)-1-(p-toluenesulfonyl)-pyrrole with R³ at 4-position]

| No. | R³ | Salt | HPLC: RT (program) | MS |
|---|---|---|---|---|
| 52 | 4-(aminocarbonyl)phenyl (H₂N-C(O)-C₆H₄-) | — | 4.50 (3) | 423.0 |
| 53 | 5-methyl-3-(aminocarbonyl)pyridin-3-yl | — | 4.57 (6) | 423.8 |
| 54 | 4-cyanophenyl (N≡C-C₆H₄-) | — | 3.87 (5) | 405.0 |

The following compounds are prepared according to Example 3 and 6, respectively

TABLE 5

[Structure: 2-(3,4,5-trimethoxyphenyl)-1-(p-toluenesulfonyl)-pyrrole with R³ at 4-position]

| No. | R³ | Salt | HPLC: RT (program) | MS |
|---|---|---|---|---|
| 55 | 4-(imidazol-1-yl)phenyl-NHCH₂- | — | 4.06 (1) | 559.0 |

TABLE 5-continued

| No. | R³ | Salt | HPLC: RT (program) | MS |
|---|---|---|---|---|
| 56 | 5-methyl-3-(aminocarbonyl)pyridin-3-yl | — | 3.72 (1) | 508.0 |
| 57 | 4-(aminosulfonyl)phenyl | — | 4.62 (6) | 542.8 |
| 58 | 5-methyl-3-(aminomethyl)pyridin-3-yl | — | 3.69 (6) | 494 |
| 59 | 5-methyl-3-((dimethylamino)methyl)pyridin-3-yl | — | 3.83 (6) | 522.3 |
| 60 | 5-methyl-3-((acetamido)methyl)pyridin-3-yl | — | 3.87 (6) | 536 |
| 61 | 4-(3-(pyrrolidin-1-yl)propoxy)phenyl | HCl | 4.20 (1) | 576.8 |
| 62 | 5-methyl-N-(2-(1-methylpyrrolidin-2-yl)ethyl)nicotinamide | HCl | 3.70 (1) | 618.9 |
| 63 | 5-methyl-N-(1-hydroxypropan-2-yl)nicotinamide | HCl | 3.94 (1) | 565.8 |

TABLE 5-continued

[Structure: 2-(3,4,5-trimethoxyphenyl)-1-(4-methylphenylsulfonyl)-pyrrole with R³ substituent]

| No. | R³ | Salt | HPLC: RT (program) | MS |
|---|---|---|---|---|
| 64 | morpholine-ethyl-NHC(O)-5-methylpyridin-3-yl | HCl | 3.69 (1) | 620.8 |
| 65 | H₃C-O-propyl-NHC(O)-5-methylpyridin-3-yl | HCl | 4.24 (1) | 579.8 |
| 66 | HOOC-5-methylpyridin-3-yl | NH₃ | 4.22 (1) | 508.8 |
| 67 | imidazol-1-yl-phenyl-N(CH₃)C(O)-CH₂- | — | | |
| 68 | 1,2,4-triazol-1-yl-phenyl-NH-CH₂- | — | 3.17 (4) | 559.7 |
| 69 | 1H-benzotriazol-5-yl-NH-CH₂- | — | 2.45 (4) | 533.7 |
| 70 | H₂N-SO₂-phenyl-NH-CH₂- | — | 2.99 (4) | 571.6 |
| 71 | morpholin-4-yl-phenyl-NH-CH₂- | — | 3.07 (3) | 577.7 |

TABLE 5-continued

[Structure: same core as above]

| No. | R³ | Salt | HPLC: RT (program) | MS |
|---|---|---|---|---|
| 72 | 3-cyanophenyl-NH-CH₂- | — | 3.31 (8) | 515.7 |
| 73 | 4-(1H-tetrazol-5-yl)phenyl-NH-CH₂- | — | 4.64 (6) | 560.7 |

The following compounds are prepared according to Example 4 and 5, respectively

TABLE 6

[Structure: 2-(benzo[1,3]dioxol-5-yl)-1-(3-chlorophenylsulfonyl)-pyrrole with R³ substituent]

| No. | R³ | Salt | HPLC: RT (program) | MS |
|---|---|---|---|---|
| 74 | imidazol-1-yl-phenyl-N(H)CH₂- | — | 4.19 (1) | 533.0 |
| 75 | H₂N-C(O)-5-methylpyridin-3-yl | — | 4.01 (1) | 482.0 |

Example 76

1-p-Methoxyphenylsulfonyl-4-(3-pyridyl)-2-(3,4,5-trimethoxyphenyl)-pyrrole

To a stirred solution of 4-(3-pyridyl)-2-(3,4,5-trimethoxyphenyl)-pyrrole (155 mg, 0.5 mmol, Example 76a) in dry DMF or THF (1.5 ml) NaH dispersion (48 mg, 2 equiv.) and p-methoxyphenylsulfonyl chloride (103 mg, 0.5 mmol) is added under a stream of nitrogen at 4° C. The reaction mixture is subsequently stirred for 12-18 h at room temperature and extracted with saturated aqueous NaHCO$_3$ solution and ethyl acetate. The organic layer is dried and purified by flash chromatography and preparative HPLC. RT (program 1) 3.79. MS: 480.7.

Example 76a

4-(3-pyridyl)-2-(3,4,5-trimethoxyphenyl)-pyrrole

A mixture of 4-bromo-1-tert-butoxycarbonyl-2-(3,4,5-trimethoxyphenyl)-pyrrole (2.0 g, 5.0 mmol, Example 76b), Pd(PPh$_3$)$_4$ (290 mg, 0.25 mmol) and pyridine-3-boronic acid (614 mg, 5.0 mmol) are evacuated for 10 min and set under argon atmosphere, followed by addition of degassed dimethoxyethane (DME, 10 ml) and 2 M aqueous Na$_2$CO$_3$ solution (10 ml). The reaction mixture is heated for 20 h to 80° C., cooled to room temperature and diluted with water and ethyl acetate. The organic layer is dried (MgSO$_4$), filtered and the solvents are evaporated. The residue is chromatographed with ethyl acetate/hexane (1:1) to yield first 1-tert-butoxycarbonyl-4-(3-pyridyl)-2-(3,4,5-trimethoxy-phenyl)-pyrrole (280 mg, 12%) as a yellowish amorphous solid and then the title compound (700 mg, 45%) as a yellowish solid, $^1$H-NMR (300 MHz, DMSO-d$_6$): 11.52 (br.s, 1H); 7.88 (br. s, 1H); 8.33 (br.d; J=6.0, 1H); 8.0-7.95 (m, 1H); 7.48 (br.s, 1H); 7.35-7.3 (m, 1H); 7.07 (br.s, 1H); 7.02 (s, 2H); 3.85 (s, 2MeO); 3.67 (s, MeO).

The side product containing the tert-butoxycarbonyl protecting group can be converted to the title compound using the following procedure: The compound is dissolved in CH$_2$Cl$_2$ (2 ml), trifluoroacetic acid (2 ml) is added at 0° C., and the mixture is stirred at r.t. for 1 h.

The solvents are evaporated, the residue is redissolved in ethyl acetate and washed with sat. aq. NaHCO$_3$ solution and dried (MgSO$_4$). Purification by flash chromatography (ethyl acetate/hexane, 1:1) gives the title compound in 90% yield.

Example 76b

4-Bromo-1-tert-butoxycarbonyl-2-(3,4,5-trimethoxyphenyl)-pyrrole

To a stirred solution of 3-(tert-butoxycarbonylamino)-1-propinyl 3,4,5-trimethoxyphenyl ketone (1.0 g, 2.78 mmol, Example 76c) in CH$_2$Cl$_2$ (10 ml) a solution of HBr (732 µl, 1.5 equiv., 33% in acetic acid) is added at 4° C. The reaction mixture is stirred for 45 min at 4° C., and poured onto ice, saturated aqueous NaHCO$_3$ solution and ethyl acetate. The organic layer is dried (MgSO$_4$), the solvents are evaporated and the residue chromatographed on SiO$_2$ with ethyl acetate/hexane (1:3) to yield the title compound (1.0 g, 89.9%) as a white solid. $^1$H-NMR (300 MHz, DMSO-d$_6$): 7.45 (d, J=2.0, 1H); 6.66 (s, 2H); 6.38 (d, J=2.0, 1H); 3.77 (s, 2MeO); 3.67 (s, MeO); 1.33 (s, tBu).

Example 76c

3-(tert-Butoxycarbonylamino)-1-propinyl 3,4,5-trimethoxyphenyl ketone

To a stirred solution of propargyl tert-butoxycarbonylamide (5.0 g, 32.3 mmol) in dry THF (120 ml) lithium diisopropylamide solution (35.5 ml, 2.2 equiv., 2 M in THF) is added under argon at −78° C. The reaction mixture is stirred for 1 h at −78° C. followed by addition of 3,4,5-trimethoxybenzaldehyde (7.44 g, 38.8 mmol, 1.2 equiv.), then again stirred for 30 min at −78° C. and allowed to come to 4° C. After stirring for 1 h at 4° C., the reaction mixture is poured onto ice, saturated ammonium chloride solution and ethyl acetate. The organic layer is extracted with brine, dried (MgSO$_4$), the solvents are evaporated and the residue chromatographed on SiO$_2$ with ethyl acetate/hexane (1:1 to 2:1) to yield the intermediate alcohol (9.55 g, 84%) as a slightly yellow oil. To a stirred suspension of MnO$_2$ (70.88 g, 0.82 mol) in CH$_2$Cl$_2$ (100 ml) a solution of the above intermediate (9.55 g) in CH$_2$Cl$_2$ (30 ml) is added at 4° C. The reaction mixture is stirred for 1 h at 4° C., and filtered over a plug of MgSO$_4$. The filter is washed several times with CH$_2$Cl$_2$ and ethyl acetate, the combined filtrate evaporated and the residue dried under reduced pressure to yield the title compound (9.1 g, 96%) as a white solid. $^1$H-NMR (300 MHz, CDCl$_3$): 7.41 (s, 2H); 4.92 (br.s, $_1$H); 4.22 (d, J=5.8, 2H); 3.95 (s, MeO); 3.94 (s, 2MeO); 1.48 (s, tBu).

The following compounds are prepared according to Example 76 using the corresponding sulfonyl chloride R$^1$SO$_2$Cl:

TABLE 7

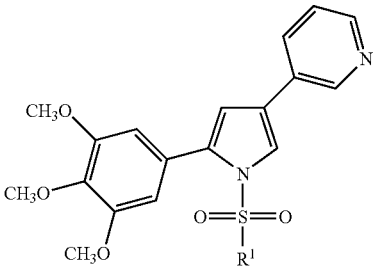

| No. | R$^1$ | HPLC: RT (program) | MS |
|---|---|---|---|
| 77 | CF$_3$O—⟨phenyl⟩— | 3.21 (3) | 534.6 |
| 78 | CH$_3$CH$_2$CH$_2$CH$_2$O—⟨phenyl⟩— | 3.59 (3) | 523.3 |
| 79 | ⟨phenyl⟩— | 3.72 (1) | 450.7 |
| 80 | F—⟨phenyl⟩— | 3.63 (7) | 469.0 |

TABLE 7-continued

| No. | R¹ | HPLC: RT (program) | MS |
|---|---|---|---|
| 81 | 4-Cl-C₆H₄ | 3.97 (1) | 484.8 |
| 82 | 4-CF₃-C₆H₄ | 4.06 (1) | 518.6 |
| 83 | 4-(CH₃)₃C-C₆H₄ | 3.45 (3) | 506.7 |
| 84 | 2-Cl-C₆H₄ | 3.74 (1) | 484.7 |
| 85 | 2,6-diCl-C₆H₃ | 3.65 (7) | 518.6 / 520.6 |
| 86 | 5-methyl-2,3-dihydrobenzofuran-yl | 2.65 (3) | 492.7 |
| 87 | 1-methyl-4-methyl-imidazol-yl | 3.22 (1) | 454.7 |
| 88 | benzyl (C₆H₅-CH₂-) | 3.73 (1) | 464.8 |
| 89 | styryl (C₆H₅-CH=CH-) | 3.94 (1) | 476.7 |
| 90 | 2-thienyl | 3.67 (1) | 456.6 |
| 91 | 4-CF₃O-3-CH₃O-C₆H₃ | 3.87 (6) | 511.2 |
| 92 | 4-O₂N-C₆H₄ | 3.74 (6) | 495.6 |
| 93 | 4-H₂N-C₆H₄ | 3.60 (6) | 465.7 |

Example 94

1-p-Methoxyphenylsulfonyl-4-p-morpholinophenylaminomethyl-2-(3,4,5-trimethoxyphenyl)-pyrrole To a stirred solution of 1-p-methoxyphenylsulfonyl-2-(3,4,5-trimethoxyphenyl)pyrrole-4-carbaldehyde (50 mg, 0.12 mmol, Example 94a) in THF (1 ml) acetic acid (21 mg, 3 equiv.), 4-morpholinoaniline (21 mg, 1.05 equiv.) and NaBH(OAc)₃ (61 mg, 2.5 equiv.) are added. The reaction mixture is stirred at room temperature for 16 h, and diluted with aqueous 1 M Na₂CO₃ solution and ethyl acetate. The organic layer is dried (MgSO₄) and purified by flash chromatography and preparative HPLC. RT (program 2) 3.52. MS: 593.7.

Example 94a 1-p-Methoxyphenylsulfonyl-2-(3,4,5-trimethoxyphenyl)-pyrrole-4-carbaldehyde To a stirred solution of 4bromo-1-p-methoxyphenylsulfonyl-2-(3,4,5-trimethoxyphenyl)-pyrrole (0.30 g, 0.62 mmol, Example 94b) in ethyl ether/THF (5 ml, 1:1 v/v) tert-butyl-lithium (1.5 equiv., 1.7 M in pentane) is added at −78° C. The reaction mixture is stirred for 20 min at −78° C., and DMF (255 mg, 5 equiv.) is added drop wise. The reaction mixture is kept for 1 h at −78° C., allowed to come to 4° C., and poured onto ice, 1 M aqueous HCl and ethyl acetate. The organic layer is dried (MgSO₄), the solvents are evaporated, and the residue chromatographed on SiO₂ with ethyl acetate/hexane to yield the title compound (0.196 g, 73%) as a light yellow solid. ¹H-NMR (300 MHz, DMSO-d₆): 9.86 (s, CHO); 8.44 (d, J=1.9, 1H); 7.38 (d, J=9.0, 2H); 7.01 (d, J=9.0, 2H); 6.56 (d, J=1.9, 1H); 6.36 (s, 2H); 3.82 (s, MeO); 3.72 (s, MeO); 3.67 (s, 2MeO).

Example 94b

4Bromo-1-p-methoxyphenylsulfonyl-2-(3,4,5-trimethoxyphenyl)-pyrrole

To a stirred solution of 3-(p-methoxyphenylsulfonylamino)-1-propinyl 3,4,5-trimethoxy-phenyl ketone (2.02 g, 2.78 mmol, Example 94c) in $CH_2Cl_2$ (10 ml) a solution of HBr (732 µl, 1.5 equiv., 33% in acetic acid) is added at 4° C. The reaction mixture is stirred for 45 min at 4° C., and poured onto ice, saturated aqueous $NaHCO_3$ solution and ethyl acetate. The organic layer is dried ($MgSO_4$), the solvents are evaporated and the residue chromatographed on $SiO_2$ with ethyl acetate/hexane (1:3) to yield the title compound (2.0 g, 86.3%) as a pink solid. $^1$H-NMR (300 MHz, DMSO-$d_6$): 7.65 (d, J=1.9, 1H); 7.38 (d, J=9.0, 2H); 7.02 (d, J=9.0, 2H); 6.40 (m, 3H); 3.82 (s, MeO); 3.72 (s, MeO); 3.69 (s, 2MeO).

Example 94c

3-(p-Methoxyphenylsulfonylamino)-1-propinyl 3,4,5-trimethoxyphenyl ketone

To a stirred solution of propargyl p-methoxyphenylsulfonylamide (1.13 g, 5.0 mmol, Example 94d) in dry THF (15 ml) lithium diisopropylamide solution (5.5 ml, 2.2 equiv., 2 M in THF) is added under argon at −78° C. The reaction mixture is stirred for 1 h at −78° C. followed by addition of 3,4,5-trimethoxybenzaldehyde (1.15 g, 6 mmol, 2 equiv.), then again stirred for 30 min at −78° C. and allowed to come to 4° C. After stirring for 1 h at 4° C. and for 1 h at room temperature, the reaction mixture is poured onto ice, saturated ammonium chloride solution and ethyl acetate. The organic layer is extracted with brine, dried ($MgSO_4$), the solvents are evaporated and the residue chromatographed on $SiO_2$ with ethyl acetate/hexane (1:1 to 2:1) to yield the intermediate alcohol as a slightly yellow oil. To a stirred suspension of $MnO_2$ (13.0 g) in $CH_2Cl_2$ (20 ml) a solution of the above intermediate in $CH_2Cl_2$ (5 ml) is added at 4° C. The reaction mixture is stirred for 1 h at 4° C., and filtered over a plug of $MgSO_4$. The filter is washed several times with $CH_2Cl_2$ and ethyl acetate, the combined filtrate is evaporated and the residue dried under reduced pressure to yield the title compound (1.51 g, 71.9%) as a slightly brownish solid. $^1$H-NMR (300 MHz, $CDCl_3$): 7.85 (d, J=8.9, 2H); 7.32 (s, 2H); 6.95 (d, J=8.9, 2H); 5.01 (t, J=6.2, 1H); 4.10 (d, J=6.2, 2H); 3.96 (s, MeO); 3.94 (s, 2MeO); 3.80 (s, MeO).

Example 94d

Propargyl p-methoxyphenylsulfonylamide

To a stirred solution of p-methoxyphenylsulfonyl chloride (8.0 g, 38.71 mmol) and pyridine (7.82 ml, 2.5 equiv.) in $CH_2Cl_2$ (100 ml) propargylamine (2.73 ml, 1.1 equiv.) is added at 4° C. The reaction mixture is stirred for 6 h at room temperature, and poured onto 1 N aqueous HCl solution and $CH_2Cl_2$. The organic layer is dried ($MgSO_4$) and the solvents are evaporated. The residue is suspended in ethyl acetate/hexane (1:8), stirred for 1 h, filtered, and the solid residue washed with ethyl acetate/hexane (1:8) and dried under reduced pressure to yield the title compound (6.1 g, 71%) as a pale yellowish solid. $^1$H-NMR (300 MHz, $CDCl_3$): 7.86 (d, J=8.9, 2H); 7.00 (d, J=8.9, 2H); 4.65 (br.s, 1H); 3.89 (s, MeO); 3.84 (~d, J=2.3, 2H); 2.12 (~t, J=2.3, 1H).

The following compounds are prepared according to Example 94:

TABLE 8

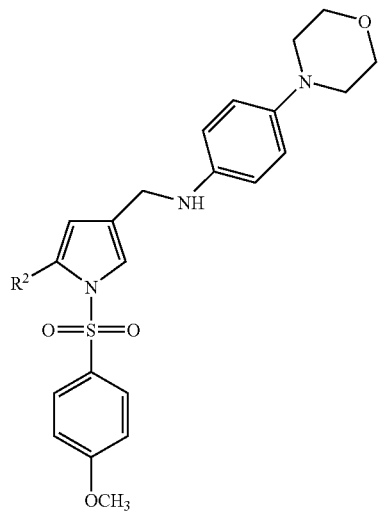

| No. | R$^2$ | HPLC: RT (program) | MS |
|---|---|---|---|
| 95 | 2-OCH$_3$, 4-CH$_3$O-phenyl | 3.67 (2) | 563.7 |
| 96 | 2-OCH$_3$, 4-CH$_3$O-phenyl | 3.67 (2) | 563.7 |
| 97 | 2-OCH$_3$-phenyl | 3.68 (2) | 533.7 |
| 98 | 3-CH$_3$O-phenyl | 3.44 (2) | 534.2 |
| 99 | 2-OCH$_3$, 4-CH$_3$O, 3-OCH$_3$-phenyl | 3.26 (2) | 593.7 |

Example 100
4-(2-Aminopyrid-5-yl)-1-p-methoxyphenylsulfonyl-2-(3,4,5-trimethoxyphenyl)-pyrrole A mixture of 1-p-methoxyphenylsulfonyl-2-(3,4,5-trimethoxyphenyl)-pyrrole-4-boronic acid 2,2-dimethylprop-1,3-diyl ester (50 mg, 0.1 mmol, Example 100a), Pd(PPh$_3$)$_4$ (115 mg, 0.1 equiv.), K$_3$PO$_4$ (41 mg, 3 equiv.) and 2-amino-5-bromopyridine (17 mg, 1.0 equiv.) are evacuated for 20 min and set under argon atmosphere, followed by addition of degassed dimethoxyethane (DME, 1 ml). The reaction mixture is heated for 16 h to 80° C., cooled to room temperature and diluted with water and ethyl acetate. The organic layer is dried (MgSO$_4$), and purified by flash chromatography and preparative HPLC. RT (program 1) 3.84. MS: 495.8.

Example 100a
1-p-Methoxyphenylsulfonyl-2-(3,4,5-trimethoxyphenyl)-pyrrole)-4-boronic acid 2,2-dimethylprop-1,3-diyl ester A mixture of 4-bromo-1-p-methoxyphenylsulfonyl-2-(3,4,5-trimethoxyphenyl)-pyrrole (46 mg, 0.9 mmol, Example 100b), bis(neopentylglycolato)diboron (37 mg, 1.8 equiv.), potassium acetate (274 mg, 3.1 equiv.) and PdCl$_2$(DPPF) ([1,1'-bis(diphenylphosphino)-ferrocene]palladium (II) dichloromethane adduct, 74 mg, 0.1 equiv.) is evacuated for 10 min and set under argon atmosphere, followed by addition of degassed dioxane (8 ml). The reaction mixture is heated for 17 h at 80° C., cooled to room temperature and diluted with water and ethyl acetate. The organic layer is dried (MgSO$_4$), filtered and the solvents are evaporated. The residue is chromatographed with ethyl acetate/hexane to yield the title compound (0.3 g, 70%) as a white foam. $^1$H-NMR (300 MHz, DMSO-d$_6$): 7.61 (d, J=1.7, 1H); 7.33 (d, J=9.0, 2H); 6.99 (d, J=9.0, 2H); 6.36 (s, 2H); 6.30 (d, J=1.7, 1H); 3.80 (s, MeO); 3.71 (s, MeO); 3.70 (s, 2CH$_2$); 3.67 (s, 2MeO); 0.95 (s, 2CH$_3$).

The following compounds are prepared according to Example 100:

TABLE 9

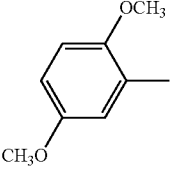

| No. | R$^2$ | HPLC: RT (program) | MS |
|---|---|---|---|
| 101 | OCH$_3$, CH$_3$O-phenyl-methyl | 3.93 (1) | 466.1 |
| 102 | OCH$_3$, CH$_3$O-phenyl-methyl | 4.10 (6) | 465.8 |
| 103 | OCH$_3$-phenyl-methyl | 4.13 (6) | 435.7 |

Example 104
4-(3-Aminocarbonylpyrid-5-yl)-1-p-methoxyphenylsulfonyl-2-(3,4,5-trimethoxyphenyl)-pyrrole A mixture of 1-p-methoxyphenylsulfonyl-2-(3,4,5-trimethoxyphenyl)-pyrrole-4-boronic acid 2,2-dimethylprop-1,3-diyl ester (50 mg, 0.1 mmol, Example 100a), Pd(PPh$_3$)$_4$ (11 mg, 0.1 equiv.), K$_3$PO$_4$ (40 mg, 3 equiv.) and 5-bromonicotinamide (19 mg 1.0 equiv.) are evacuated for 20 min and set under argon atmosphere, followed by addition of degassed dimethoxyethane (DME, 1 ml). The reaction mixture is heated for 16 h to 80° C., cooled to room temperature and diluted with water and ethyl acetate. The organic layer is dried (MgSO$_4$), and purified by flash chromatography and preparative HPLC. RT (program 1) 3.87; MS: 523.7

The following compounds are prepared according to Example 104:

TABLE 10

[Structure: pyrrole with N-sulfonyl-(4-methoxyphenyl) group, 3-position substituted with 5-(pyridin-3-yl)-with CONH2, and 2-position with R²]

| No. | R² | HPLC: RT (program) | MS |
|---|---|---|---|
| 105 | 2-methyl-4-methoxy-phenyl (OCH3, CH3O) | 3.97 (1) | 493.8 |
| 106 | 2-methoxy-4-methoxy-phenyl (OCH3, CH3O) | 4.13 (6) | 493.9 |
| 107 | 2-methyl-phenyl with OCH3 | 4.14 (6) | 463.7 |

Example 108

Cell Cultures and Cell Lines

Cell lines are cultured in RPMI-1640 tissue culture medium containing either 5% or 10% fetal calf serum, 0.05 mM 2-mercaptoethanol, 2 mM glutamine and penicillin/streptomycin 50 µg/ml (complete medium) (Sigma, Buchs, Switzerland). General growth conditions are 37° C. and 7.5% $CO_2$.

The following mouse cell lines (either EGFP transfected or not) are being used: A20.2J (ATCC: TIB-208), MC57G (ATCC: CRL-2295).

The following human cell lines (either EGFP transfected or not) are being used: HeLa (ATCC: CCL-2), KB (ATCC: CCL-17), MCF7 (ATCC: HTB-22), SK-BR-3 (ATCC: HTB-30), SK-Mel 1 (ATCC: HTB-67), SK-Mel 28 (ATCC: HTB-72), PC-3 (ATCC: CRL-1435), SW 480 (ATCC: CCL-228), NCI-H460 (ATCC: HTB-177), NCI-H1792 (ATCC: CRL-5895), HT1080 (ATCC: CCL-21), Jurkat (ATCC: TIB-152), Ramos (ATCC: CRL-1596), Raji (ATCC: CCL-86), H9 (ATCC: HTB-176), Hut78 (ATCC: TIB-161), K562 (ATCC: CCL 243), HL-60 (ATCC: CCL 240), U-87MG (ATCC: HTB-14), HepG2 (ATCC: HB-8065), U-2 OS (ATCC: HTB-96), Saos-2 (ATCC: HTB-85), U937 (ATCC: CRL 1593), Hs 578T (ATCC: HTB 126), HBL-100 (ATCC: HTB 124), Molt-4 (ATCC: CRL 1582).

Example 109

Primary Screening Setup

All the manipulations are performed under sterile conditions. The assays are being performed in commercially available 96 or 384 well flat bottom clear microtiter plates (Greiner, Germany) respectively, which are suitable for tissue culture techniques. A defined number of EGFP transfected adherent test cells (96 well plates: $10^4$-$10^5$, 384 well plates: 1500-2*$10^4$) are plated out 24 h before treatment either in 75 µl (96 well plates) or 60 µl (384 well plates) complete medium per well in order to ensure appropriate cell spreading. For this purpose a peristaltic pump (e.g. Multidrop by Thermo-Labsystems, Finland) or another suitable device is used. Cells in suspension are plated out according to the same procedure but 1 h prior to treatment. Between seeding out and treatment or addition of compounds the cells are incubated at 37° C. under 7.5% $CO_2$. Subsequently, the compounds under investigation are added at defined concentrations (40-80 µM in either 25 µl (96 well plates) or 20 µl (384 well plates) complete medium containing max 4% DMSO) with an appropriate device (e.g. liquid handling system, multi channel pipette etc.) resulting in a final concentration in the test well of 10-20 µM compound in max 1% DMSO.

Immediately after the addition of the compounds to the cells the zero fluorescence value (t=0 h) is determined by using a fluorescence microplate reader in order to be able to normalize the fluorescence activities. Afterwards, the test plates are further incubated for a total of 48 h at 37° C. under 7.5% $CO_2$ and are shortly removed only for the purpose of measurement at 8 h, 24 h and 48 h, respectively.

Example 110

Measurement and Quantification of the Primary Screening

Relative fluorescence activities of EGFP in compound treated test cells in relation to control cells and cells treated with standard drugs are measured by using a BMG Fluostar microplate fluorescence reader equipped with a filter pair for excitation/emission at 485 nm/520 nm. The optimum signal to noise ratio is detected by using the time-resolved mode of measurement with a delay of 20 µs and an integration time over 1 ms. The gain is adjusted in such a way that the control cells produce a fluorescence activity of 90% of the maximum. Kinetics is performed by measuring the relative fluorescence activities at t=0 h, 8 h, 24 h and 48 h. Crude fluorescence activities are individually normalized for different cell numbers and various optical activities of the test compounds/plate-wells by dividing each value from t=8 h, 24 h and 48 h by the value of t=0 h resulting in E(8), E(24) and E(48) values. Subsequently, the E(x) values are further processed by forming the inverse (Q-value) of the products E(8)*E(24)*E(48) which result in numbers>1 for apoptotic/necrotic activities of the compounds and numbers<1 for proliferative activities of the compounds. Controls (untreated) show values similar to 1. Compounds producing Q values>2 are being considered relevant in terms of apoptotic/necrotic activity and are subsequently tested in the secondary screening setup.

Example 111

Secondary Screening Setup

All the manipulations are performed under sterile conditions. The assays are being performed in case of adherent cells in commercially available 24 well flat bottom tissue culture plates (Greiner, Germany) and in case of suspension cells in polypropylene tubes (P-tubes) 1.4 ml (Matrix, UK), respectively.

Adherent test cells: $2*10^4$-$4*10^4$ of EGFP transfected cells in 0.5 ml complete medium are plated out 24 h before treatment. At t=0 the medium is removed and 450 µl new complete medium is added. Subsequently, 50 µl complete medium containing the test compound in max. 5% DMSO is added resulting in final concentrations of 20 µM, 10 µM, 3 µM, 1 µM and 0.3 µM of the test compounds, respectively. After 48 h incubation the cells are harvested and analyzed with fluorescence activated cell scanning device (FACSCalibur™, BD Biosciences) according to standard procedures.

Suspension cells: $10^5$ test cells in 450 µl complete medium are pipetted into P-tubes. 50 µl complete medium containing the compounds (see adherent cells) is added immediately. After 48 h of incubation the test cells are analyzed directly on a FACSCalibur™.

Example 112

Quantification of the Secondary Screening

By monitoring the EGFP fluorescence activity in FL1 on a FACSCalibur™, it is possible to distinguish between proliferating cells, apoptotic cells and necrotic cells within the same cell population. The proliferating cells show a high GFP fluorescence activity, the apoptotic population shows an intermediate fluorescence activity whereas the necrotic cells demonstrate a residual fluorescence activity comparable to mock-transfected cells. Within the CellQuest Software (BD Biosciences) three regions are defined in the histogram: M1 comprising the proliferating cells, M2 comprising the apoptotic cell population and M3 comprising the necrotic cell population. As readout the relative abundance of the cells belonging either to M1, M2 or M3 are expressed. Compounds inducing M2 values>50% and M3 values<30% are being considered relevant and are further tested and characterized in the tertiary/advanced screening setup.

Example 113

Tertiary Screening Setup

A) Hoechst 33342 Nuclear Staining

This assay is performed in 96 well tissue culture plates. Appropriate number of cells (adherent cells: $3-5*10^3$, suspension cells: $8-10*10^3$) are being seeded out in 80 µl complete medium. Adherent cells are incubated for 24 h for proper spreading out before addition of test compounds while suspension cells are immediately treated with test compounds after seeding out. The test compounds are added in 20 µl complete medium containing max 5% DMSO. The final compound concentrations in the assays are 10 µM, 3 µM, 1 µM and 0.3 µM, respectively. After 24 h or 48 h incubation at culture conditions, 10 µl medium containing Hoechst 33342 dye (Sigma B-2261) at 2-5 µg/ml are added to each well. The assay plates are then further incubated for 30 min and subsequently analyzed with a standard inverted fluorescence microscope.

The readout allows the determination of the fraction of apoptotic nuclei as well as other morphological criteria specific for apoptosis as a function of the treatment. Results are indicated in Table 11. The following scores are used: 0 relating to no activity, 1 relating to weak activity comprising less than 50% of the cells and score 2 relating to strong activity comprising more than 50% of the cells.

TABLE 11

| | | Hoechst 33342 nuclear staining | | | | | |
|---|---|---|---|---|---|---|---|
| Example | conc | Jurkat | Jily | PBLs | HeLa | H460 | MRC5 |
| 2 | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 2 × 2HCl | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 7 | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 8 | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 9 | 3 | 2 | nd | nd | 1 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 10 | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 11 | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 12 | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 13 | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 14 | 3 | 2 | nd | nd | 2 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 15 | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 16 | 3 | 0 | nd | nd | 1 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 17 | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 18 | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 19 | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 20 | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 21 | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 22 | 3 | 0 | nd | nd | 0 | nd | nd |
| | 1 | 0 | nd | nd | 0 | nd | nd |
| | 0.3 | 0 | nd | nd | 0 | nd | nd |
| | 0.1 | 0 | nd | nd | 0 | nd | nd |
| 22 | 3 | 0 | nd | nd | 0 | nd | nd |
| | 1 | 0 | nd | nd | 0 | nd | nd |

TABLE 11-continued

Hoechst 33342 nuclear staining

| Example | conc | Jurkat | Jily | PBLs | HeLa | H460 | MRC5 |
|---|---|---|---|---|---|---|---|
|  | 0.3 | 0 | nd | nd | 0 | nd | nd |
|  | 0.1 | 0 | nd | nd | 0 | nd | nd |
| 23 | 3 | 0 | nd | nd | 0 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 24 | 3 | 0 | nd | nd | 0 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 25 | 3 | 0 | nd | nd | 1 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 26 | 3 | 0 | nd | nd | 0 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 27 | 3 | 0 | nd | nd | 0 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 28 | 3 | 0 | nd | nd | 0 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 29 | 3 | 0 | nd | nd | 0 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 30 | 3 | 0 | nd | nd | 0 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 31 | 3 | 0 | nd | nd | 0 | nd | nd |
|  | 1 | 0 | nd | nd | 0 | nd | nd |
|  | 0.3 | 0 | dn | dn | 0 | dn | dn |
|  | 0.1 | 0 | nd | nd | 0 | nd | nd |
| 32 | 3 | 0 | nd | nd | 0 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 33 | 3 | 0 | nd | nd | 0 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 34 | 3 | 0 | nd | nd | 0 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 35 | 10 | 0 | nd | nd | 0 | nd | nd |
|  | 3 | 0 | nd | nd | 0 | nd | nd |
|  | 1 | 0 | nd | nd | 0 | nd | nd |
|  | 0.3 | 0 | nd | nd | 0 | nd | nd |
| 36 | 10 | 0 | nd | nd | 0 | nd | nd |
|  | 3 | 0 | nd | nd | 0 | nd | nd |
|  | 1 | 0 | nd | nd | 0 | nd | nd |
|  | 0.3 | 0 | nd | nd | 0 | nd | nd |
| 37 | 10 | 0 | nd | nd | 0 | nd | nd |
|  | 3 | 0 | nd | nd | 0 | nd | nd |
|  | 1 | 0 | nd | nd | 0 | nd | nd |
|  | 0.3 | 0 | nd | nd | 0 | nd | nd |
| 38 | 10 | 0 | nd | nd | 0 | nd | nd |
|  | 3 | 0 | nd | nd | 0 | nd | nd |
|  | 1 | 0 | nd | nd | 0 | nd | nd |
|  | 0.3 | 0 | nd | nd | 0 | nd | nd |
| 39 | 10 | 0 | nd | nd | 0 | nd | nd |
|  | 3 | 0 | nd | nd | 0 | nd | nd |
|  | 1 | 0 | nd | nd | 0 | nd | nd |
|  | 0.3 | 0 | nd | nd | 0 | nd | nd |
| 40 | 10 | 0 | nd | nd | 0 | nd | nd |
|  | 3 | 0 | nd | nd | 0 | nd | nd |
|  | 1 | 0 | nd | nd | 0 | nd | nd |
|  | 0.3 | 0 | nd | nd | 0 | nd | nd |
| 41 | 10 | 0 | nd | nd | 0 | nd | nd |
|  | 3 | 0 | nd | nd | 0 | nd | nd |
|  | 1 | 0 | nd | nd | 0 | nd | nd |
|  | 0.3 | 0 | nd | nd | 0 | nd | nd |
| 42 | 10 | 0 | nd | nd | 0 | nd | nd |
|  | 3 | 0 | nd | nd | 0 | nd | nd |
|  | 1 | 0 | nd | nd | 0 | nd | nd |
|  | 0.3 | 0 | nd | nd | 0 | nd | nd |
| 43 | 10 | 0 | nd | nd | 0 | nd | nd |
|  | 3 | 0 | nd | nd | 0 | nd | nd |
|  | 1 | 0 | nd | nd | 0 | nd | nd |
|  | 0.3 | 0 | nd | nd | 0 | nd | nd |
| 44 | 10 | 2 | nd | nd | 2 | nd | nd |
|  | 3 | 0 | nd | nd | 0 | nd | nd |
|  | 1 | 0 | nd | nd | 0 | nd | nd |
|  | 0.3 | 0 | nd | nd | 0 | nd | nd |
| 45 | 10 | 2 | nd | nd | 1 | nd | nd |
|  | 3 | 0 | nd | nd | 0 | nd | nd |
|  | 1 | 0 | nd | nd | 0 | nd | nd |
|  | 0.3 | 0 | nd | nd | 0 | nd | nd |
| 46 | 10 | 0 | nd | nd | 0 | nd | nd |
|  | 3 | 0 | nd | nd | 0 | nd | nd |
|  | 1 | 0 | nd | nd | 0 | nd | nd |
|  | 0.3 | 0 | nd | nd | 0 | nd | nd |
| 47 | 3 | 0 | nd | nd | 2 | nd | nd |
|  | 1 | 0 | nd | nd | 2 | nd | nd |
|  | 0.3 | 0 | nd | nd | 0 | nd | nd |
|  | 0.1 | 0 | nd | nd | 0 | nd | nd |
| 48 | 3 | 0 | nd | nd | 0 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 49 | 3 | 0 | nd | nd | 0 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 50 | 3 | 2 | nd | nd | 2 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 51 | 3 | 2 | 2 | 0 | 2 | 2 | 1 |
|  | 1 | 2 | 2 | 0 | 2 | 2 | 1 |
|  | 0.3 | 0 | 0 | 0 | 0 | 0 | 0 |
|  | 0.1 | 0 | 0 | 0 | 0 | 0 | 0 |
| 52 | 3 | 0 | nd | nd | 0 | nd | nd |
|  | 1 | 0 | nd | nd | 0 | nd | nd |
|  | 0.3 | 0 | nd | nd | 0 | nd | nd |
|  | 0.1 | 0 | nd | nd | 0 | nd | nd |
| 53 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 54 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 55 | 3 | 2 | 2 | 0 | 2 | 2 | 1 |
|  | 1 | 2 | 2 | 0 | 1 | 0 | 0 |
|  | 0.3 | 0 | 0 | 0 | 0 | 0 | 0 |
|  | 0.1 | 0 | 0 | 0 | 0 | 0 | 0 |
| 56 | 3 | 2 | 2 | 0 | 2 | 2 | 2 |
|  | 1 | 2 | 2 | 0 | 2 | 2 | 2 |
|  | 0.3 | 2 | 2 | 0 | 0 | 2 | 2 |
|  | 0.1 | 0 | 0 | 0 | 0 | 0 | 0 |
| 56 × 2HCl | 3 | 2 | 2 | 0 | 2 | 2 | 2 |
|  | 1 | 2 | 2 | 0 | 2 | 2 | 2 |
|  | 0.3 | 1 | 2 | 0 | 0 | 0 | 0 |
|  | 0.1 | 0 | 0 | 0 | 0 | 0 | 0 |
| 57 | 3 | 2 | nd | 0 | 2 | nd | nd |
|  | 1 | 1 | nd | 0 | 0 | nd | nd |
|  | 0.3 | 0 | nd | 0 | 0 | nd | nd |
|  | 0.1 | 0 | nd | 0 | 0 | nd | nd |
| 58 | 3 | 2 | 2 | 0 | 2 | 2 | 2 |
|  | 1 | 2 | 2 | 0 | 2 | 2 | 1 |

TABLE 11-continued

Hoechst 33342 nuclear staining

| Example | conc | Jurkat | Jily | PBLs | HeLa | H460 | MRC5 |
|---|---|---|---|---|---|---|---|
|  | 0.3 | 2 | 0 | 0 | 0 | 0 | 0 |
|  | 0.1 | 0 | 0 | 0 | 0 | 0 | 0 |
| 59 | 3 | 2 | 0 | 0 | 0 | 2 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 60 | 3 | 2 | 2 | 0 | 2 | 2 | 2 |
|  | 1 | 2 | 2 | 0 | 1 | 2 | 0 |
|  | 0.3 | 2 | 0 | 0 | 0 | 0 | 0 |
|  | 0.1 | 0 | 0 | 0 | 0 | 0 | 0 |
| 61 | 3 | 2 | 0 | 0 | 2 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 62 | 3 | 2 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 63 | 3 | 2 | 0 | 0 | 2 | 0 | 0 |
|  | 1 | 2 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 64 | 3 | 2 | 2 | 0 | 2 | 2 | 2 |
|  | 1 | 2 | 2 | 0 | 2 | 2 | 2 |
|  | 0.3 | 0 | 0 | 0 | 0 | 0 | 0 |
|  | 0.1 | 0 | 0 | 0 | 0 | 0 | 0 |
| 65 | 3 | 2 | 2 | 0 | 2 | 2 | 2 |
|  | 1 | 2 | 2 | 0 | 0 | 2 | 2 |
|  | 0.3 | 0 | 0 | 0 | 0 | 0 | 0 |
|  | 0.1 | 0 | 0 | 0 | 0 | 0 | 0 |
| 66 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 67 | 3 | nd | nd | nd | nd | nd | nd |
|  | 1 | nd | nd | nd | nd | nd | nd |
|  | 0.3 | nd | nd | nd | nd | nd | nd |
|  | 0.1 | nd | nd | nd | nd | nd | nd |
| 68 | 3 | 2 | 2 | 0 | 2 | 2 | 2 |
|  | 1 | 2 | 2 | 0 | 0 | 2 | 0 |
|  | 0.3 | 0 | 0 | 0 | 0 | 0 | 0 |
|  | 0.1 | 0 | 0 | 0 | 0 | 0 | 0 |
| 69 | 3 | 2 | 2 | 0 | 2 | 2 | 2 |
|  | 1 | 2 | 1 | 0 | 0 | 0 | 0 |
|  | 0.3 | 0 | 0 | 0 | 0 | 0 | 0 |
|  | 0.1 | 0 | 0 | 0 | 0 | 0 | 0 |
| 70 | 3 | 2 | 2 | 0 | 0 | 2 | 2 |
|  | 1 | 2 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 71 | 3 | 2 | 2 | 0 | 2 | 2 | 2 |
|  | 1 | 2 | 2 | 0 | 2 | 2 | 2 |
|  | 0.3 | 2 | 0 | 0 | 0 | 0 | 0 |
|  | 0.1 | 0 | 0 | 0 | 0 | 0 | 0 |
| 72 | 3 | 1 | 1 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 73 | 3 | 2 | 1 | 0 | 0 | 2 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 74 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 75 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 76 | 3 | 2 | 2 | 0 | 2 | 2 | 1 |
|  | 1 | 2 | 2 | 0 | 2 | 2 | 1 |
|  | 0.3 | 2 | 2 | 0 | 2 | 2 | 1 |
|  | 0.1 | 2 | 2 | 0 | 1 | 2 | 1 |
| 77 | 3 | 2 | 1 | 0 | 0 | 1 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 78 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 79 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 80 | 3 | 2 | 2 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 81 | 3 | 2 | 1 | 0 | 1 | 2 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 82 | 3 | 2 | 2 | 0 | 2 | 2 | 1 |
|  | 1 | 2 | 1 | 0 | 2 | 2 | 1 |
|  | 0.3 | 0 | 0 | 0 | 0 | 0 | 0 |
|  | 0.1 | 0 | 0 | 0 | 0 | 0 | 0 |
| 83 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 84 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 85 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 86 | 3 | 2 | 2 | 0 | 1 | 2 | 1 |
|  | 1 | 2 | 1 | 0 | 0 | 0 | 0 |
|  | 0.3 | 0 | 0 | 0 | 0 | 0 | 0 |
|  | 0.1 | 0 | 0 | 0 | 0 | 0 | 0 |
| 87 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 88 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 89 | 3 | 1 | 1 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 90 | 3 | 2 | 1 | 0 | 2 | 2 | 0 |
|  | 1 | 2 | 1 | 0 | 0 | 0 | 0 |
|  | 0.3 | 0 | 0 | 0 | 0 | 0 | 0 |
|  | 0.1 | 0 | 0 | 0 | 0 | 0 | 0 |
| 91 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 92 | 3 | 2 | 2 | 0 | 0 | 1 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 93 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 94 | 3 | 2 | 2 | 0 | 2 | 2 | 2 |
|  | 1 | 2 | 2 | 0 | 2 | 2 | 2 |
|  | 0.3 | 2 | 2 | 0 | 2 | 2 | 0 |
|  | 0.1 | 0 | 0 | 0 | 0 | 0 | 0 |
| 95 | 3 | 2 | 2 | 0 | 2 | 2 | 0 |
|  | 1 | 0 | 0 | 0 | 0 | 0 | 0 |

TABLE 11-continued

Hoechst 33342 nuclear staining

| Example | conc | Jurkat | Jily | PBLs | HeLa | H460 | MRC5 |
|---|---|---|---|---|---|---|---|
|  | 0.3 | 0 | 0 | 0 | 0 | 0 | 0 |
|  | 0.1 | 0 | 0 | 0 | 0 | 0 | 0 |
| 96 | 3 | 0 | 1 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 97 | 3 | 0 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 98 | 3 | 1 | 0 | 0 | 0 | 0 | 0 |
|  | 1 | 0 | 0 | 0 | 0 | 0 | 0 |
|  | 0.3 | 0 | 0 | 0 | 0 | 0 | 0 |
|  | 0.1 | 0 | 0 | 0 | 0 | 0 | 0 |
| 99 | 3 | 2 | 2 | 0 | 2 | 2 | 1 |
|  | 1 | 2 | 2 | 0 | 2 | 2 | 1 |
|  | 0.3 | 0 | 0 | 0 | 0 | 0 | 0 |
|  | 0.1 | 0 | 0 | 0 | 0 | 0 | 0 |
| 100 | 3 | 2 | 2 | 0 | 2 | 2 | 2 |
|  | 1 | 2 | 2 | 0 | 2 | 2 | 2 |
|  | 0.3 | 2 | 2 | 0 | 2 | 2 | 1 |
|  | 0.1 | 0 | 0 | 0 | 0 | 0 | 0 |
| 101 | 3 | 2 | 2 | 0 | 2 | 2 | 2 |
|  | 1 | 2 | 2 | 0 | 2 | 2 | 2 |
|  | 0.3 | 2 | 2 | 0 | 2 | 2 | 2 |
|  | 0.1 | 0 | 0 | 0 | 0 | 0 | 0 |
| 102 | 3 | 2 | 2 | 0 | 2 | 2 | 2 |
|  | 1 | 2 | 2 | 0 | 1 | 1 | 0 |
|  | 0.3 | 0 | 0 | 0 | 0 | 0 | 0 |
|  | 0.1 | 0 | 0 | 0 | 0 | 0 | 0 |
| 103 | 3 | 2 | 2 | 0 | 2 | 2 | 1 |
|  | 1 | 2 | 2 | 0 | 0 | 0 | 0 |
|  | 0.3 | 0 | 0 | 0 | 0 | 0 | 0 |
|  | 0.1 | 0 | 0 | 0 | 0 | 0 | 0 |
| 104 | 3 | 2 | 2 | 0 | 2 | 2 | 2 |
|  | 1 | 2 | 2 | 0 | 2 | 2 | 2 |
|  | 0.3 | 2 | 2 | 0 | 2 | 2 | 1 |
|  | 0.1 | 0 | 0 | 0 | 0 | 0 | 0 |
| 105 | 3 | 2 | 2 | 0 | 2 | 2 | 1 |
|  | 1 | 2 | 2 | 0 | 0 | 0 | 0 |
|  | 0.3 | 0 | 0 | 0 | 0 | 0 | 0 |
|  | 0.1 | 0 | 0 | 0 | 0 | 0 | 0 |
| 106 | 3 | 2 | 2 | 0 | 2 | 2 | 1 |
|  | 1 | 2 | 1 | 0 | 1 | 1 | 0 |
|  | 0.3 | 0 | 0 | 0 | 0 | 0 | 0 |
|  | 0.1 | 0 | 0 | 0 | 0 | 0 | 0 |
| 107 | 3 | 2 | 2 | 0 | 2 | 2 | 0 |
|  | 1 | 2 | 2 | 0 | 0 | 1 | 0 |
|  | 0.3 | 0 | 0 | 0 | 0 | 0 | 0 |
|  | 0.1 | 0 | 0 | 0 | 0 | 0 | 0 |

0 no effect
1 weak effect
2 strong effect

B) MTS Proliferation Assay

The assay is performed in 96 well tissue culture plates. The cells (range: $1.5*10^3$-$10^4$) are seeded out in 80 l complete medium 24 h prior to compound treatment. The test compounds are added in 20 µl complete medium containing max 5% DMSO. The final compound concentrations in the assays are 10 µM, 3 µM, 1 µM and 0.3 µM, respectively. The assay plates are incubated for 72 h at culture conditions. The MTS reagent is prepared according to the manufacturer's protocol (Promega G1111). 20 µl MTS reagent are added to each well, the assay plates are quickly spun and incubated for another 3 h at culture conditions. Subsequently, the plates are shortly shacked and absorption measured with a microplate-reader at 492 nm. $IC_{50}$ values are determined by graphical analysis and are indicated in the Table 12 in µM concentration.

TABLE 12

MTS proliferation assay (IC50 at 72 h)

| Example | Jurkat | Jily | HeLa | MRC5 |
|---|---|---|---|---|
| 1 | nd | nd | 0 | 0 |
| 2 | nd | nd | 0 | 0 |
| 3 | 0 | nd | 0 | 0 |
| 4 | 0 | nd | 0 | 0 |
| 5 | 0 | nd | 0 | 0 |
| 6 | 2 | nd | 1 | 1 |
| 7 | nd | nd | 0 | nd |
| 8 | nd | nd | 0 | nd |
| 9 | nd | nd | 0 | nd |
| 10 | nd | nd | 0 | 0 |
| 11 | nd | nd | 0 | nd |
| 12 | 0 | nd | 0 | 0 |
| 13 | 0 | nd | 0 | 0 |
| 14 | 0 | nd | 0 | 0 |
| 15 | 0 | nd | 0 | 0 |
| 16 | 0 | nd | 0 | 0 |
| 17 | 0 | nd | 0 | 0 |
| 18 | 0 | nd | 0 | 0 |
| 19 | 0 | nd | 0 | 0 |
| 20 | 0 | nd | 0 | 0 |
| 21 | 0 | nd | 0 | 0 |
| 22 | 0 | nd | 0 | 0 |
| 23 | 0 | nd | 0 | 0 |
| 24 | 0 | nd | 0 | 0 |
| 25 | 0 | nd | 0 | 0 |
| 26 | 0 | nd | 0 | 0 |
| 27 | 0 | nd | 0 | 0 |
| 28 | 0 | nd | 0 | 0 |
| 29 | 0 | nd | 0 | 0 |
| 30 | 0 | nd | 0 | 0 |
| 31 | 0 | nd | 0 | 0 |
| 32 | 0 | nd | 0 | 0 |
| 33 | 0 | nd | 0 | 0 |
| 34 | 0 | nd | 0 | 0 |
| 35 | 0 | nd | 0 | 0 |
| 36 | 0 | nd | 0 | 0 |
| 37 | 0 | nd | 0 | 0 |
| 38 | 0 | nd | 0 | 0 |
| 39 | 0 | nd | 0 | 0 |
| 40 | 0 | nd | 0 | 0 |
| 41 | nd | nd | 0 | 0 |
| 42 | 0 | nd | 0 | 0 |
| 43 | nd | nd | 0 | 0 |
| 44 | nd | nd | 0 | 0 |
| 45 | nd | nd | 0 | 0 |
| 46 | 0 | nd | 0 | 0 |
| 47 | 0 | nd | 0 | nd |
| 48 | 0 | nd | 0 | 0 |
| 49 | 0 | nd | 0 | 0 |
| 50 | 1 | nd | 0 | 0 |
| 51 | 1 | 1 | 1 | 1 |
| 52 | 0 | nd | 0 | 0 |
| 53 | 1 | nd | 0 | 0 |
| 54 | 1 | nd | 0 | 0 |
| 55 | 1 | 0 | 0 | 1 |
| 56 | 2 | 1 | 1 | 1 |
| 57 | 2 | 1 | 1 | 1 |
| 58 | 1 | 1 | 1 | 0 |
| 59 | nd | nd | 0 | 0 |
| 60 | 1 | 1 | 1 | 1 |
| 61 | 0 | nd | 0 | 0 |
| 62 | 0 | nd | 0 | 0 |
| 63 | 1 | 1 | 1 | 1 |
| 64 | 1 | 1 | 1 | 1 |
| 65 | 1 | 1 | 1 | 1 |
| 66 | 0 | nd | 0 | 0 |
| 67 | nd | nd | nd | nd |
| 68 | 1 | nd | 1 | 0 |
| 69 | 1 | nd | 0 | 0 |
| 70 | 1 | nd | 0 | 0 |
| 71 | 1 | nd | 1 | 1 |
| 72 | 0 | nd | 0 | 0 |
| 73 | 0 | 0 | 0 | 0 |
| 74 | 0 | nd | 0 | 0 |
| 75 | 0 | nd | 0 | 0 |

TABLE 12-continued

MTS proliferation assay (IC50 at 72 h)

| Example | Jurkat | Jily | HeLa | MRC5 |
|---|---|---|---|---|
| 76 | 2 | 2 | 2 | 2 |
| 77 | 0 | nd | 0 | 0 |
| 78 | 0 | nd | 0 | 0 |
| 79 | 1 | 0 | 0 | 0 |
| 80 | 0 | 0 | 0 | 0 |
| 81 | 0 | 0 | 0 | 0 |
| 82 | 1 | 0 | 0 | 0 |
| 83 | 0 | 0 | 0 | 0 |
| 84 | 0 | 0 | 0 | 0 |
| 85 | 0 | 0 | 0 | 0 |
| 86 | 1 | 1 | 0 | 0 |
| 87 | 0 | 0 | 0 | 0 |
| 88 | 0 | 0 | 0 | 0 |
| 89 | 0 | 0 | 0 | 0 |
| 90 | 1 | 1 | 0 | 0 |
| 91 | 0 | 0 | 0 | 0 |
| 92 | 0 | 0 | 0 | 0 |
| 93 | 0 | 0 | 0 | 0 |
| 94 | 2 | 2 | 2 | 2 |
| 95 | 0 | 0 | 0 | 0 |
| 96 | 0 | 0 | 0 | 0 |
| 97 | 0 | 0 | 0 | 0 |
| 98 | 0 | 0 | 0 | 0 |
| 99 | 1 | 1 | 1 | 0 |
| 100 | 2 | 2 | 2 | 2 |
| 101 | 2 | 2 | 1 | 1 |
| 102 | 1 | 1 | 0 | 0 |
| 103 | 1 | 1 | 0 | 0 |
| 104 | 2 | 2 | 1 | 2 |
| 105 | 1 | 1 | 0 | 0 |
| 106 | 0 | 0 | 0 | 0 |
| 107 | 1 | 1 | 0 | 0 |

0 IC50 > 1 μM
1 IC50 < 1 μM
2 IC50 < 0.2 μM

C) AnnexinV/7-AAD Staining

Adherent cells (1-2*10$^5$) are 24 h prior to compound treatment seeded into 24 well tissue culture plates. Suspension cells are pipetted into P-tubes immediately before treatment. Test compounds are added leading to a final concentrations of 10 μM. After 24 h treatment cells are harvested (in case of adherent cells by trypsinization) and transferred to FACS tubes (BD Biosciences). After centrifugation and removal of the supernatant, 100 μl complete medium containing AnnexinV-GST (10 μg) is added, mixed and incubated at 4° C. for 30 min. Subsequently, the cells are washed once with medium and incubated with 100 μl anti-GST Alexa 488 (Molecular Probes A-11131) in medium diluted 1:500 for 30 min at 4° C. Then, cells are washed once and stained with 1 μg/ml 7-aminoactinomycin D (7-MD) (Molecular Probes A-1310) in 250 μl medium and analyzed on the FACSCalibur™. AnnexinV is measured in FL1 whereas 7-AAD is measured in FL3.

D) PI Staining for Cell Cycle Distribution 1-2*10$^5$ cells are seeded into 24 well tissue culture plates and incubated for 24 h prior to compound addition. Compounds are added for 24 h in a final concentration of 3 μM or 10 μM. Adherent cells are harvested by trypsinization. The cell suspensions are fixed by adding 2 parts ice cold ethanol 100% while vortexing. Then the samples are stored for >2 h at −20° C. Subsequently the cells are washed with PBS once and resuspended in 250 μl PBS containing 50 μg/ml PI (Calbiochem # 537059), then the samples are incubated at 37° C. for 30 min and subsequently analyzed on a FACSCalibur™ monitoring linear PI fluorescence activity on FL2. The readout allows the detection of a possible direct or indirect influence of the tested compounds on the cell cycle. The following events can occur: a) Generation of a subG1 peak indicative for DNA fragmentation, b) increase of the cell population arrested in G2M phase. Both events are scored by 1 for weak and 2 for strong occurrence. 0 indicates no occurrence at all. In Table 13 the influences of several tested compounds are demonstrated.

TABLE 13

PI staining for cell cycle distribution (48 h)

| | HeLa 10μM | | Jurkat 3μM | |
|---|---|---|---|---|
| No | subG1 | G2M | subG1 | G2M |
| 6 | 0 | 2 | 0 | 1 |
| 51 | 0 | 2 | 0 | 1 |
| 53 | 0 | 2 | 0 | 1 |
| 55 | 0 | 2 | 0 | 1 |
| 56 | 0 | 2 | 0 | 1 |

0: no effect
1: weak effect
2: strong effect

E) BrdU Incorporation (Proliferation)

Adherent cells are seeded out at 2-4*10$^4$ cells/well/ml in 24 well tissue culture plates 24 h prior to treatment. Suspension cells are seeded out at 2*10$^5$ cells/ml/well in 24 well plates. Compounds are added leading to final concentrations of 3 μM and 10 μM, respectively. Subsequently, BrdU (Molecular Probes #B-23151) at 10 μM final concentration is added and the plates are incubated for 48 h. After the incubation cells are processed according to standard procedures. The detection of the incorporated BrdU is done with the anti-bromodeoxyuridine Mab PRB-1, Alexa Fluor 660 conjugate (Molecular Probes #A-21306). The analysis is performed on a FACSCalibur™ by monitoring the fluorescence activity on FL3. The readout reflects DNA synthesis which is a hallmark for proliferation.

F) Caspase Dependencies

Caspase dependencies are being evaluated by combining the compound treatment with the pan-caspase inhibitor zVAD or its control peptide zFA (ICN Pharmaceuticals # FK009 and FK029, respectively). Both peptides are being used at 20 μM concentration. In case of caspase dependencies a clear inhibition of the specific readout in all apoptosis tests should be detected. By comparing the readout of zVAD and zFA treated samples with the compound control it is possible to detect caspase resp. cystein proteinase dependencies. In case of inhibition by zVAD but not by zFA a clear caspase dependency is obvious. An inhibition by zVAD as well as by zFA points towards the involvement of cystein proteinases in the apoptotic cascade.

Example 114

Soft Capsules 5000 soft gelatin capsules, each comprising as active ingredient 0.05 g of one of the compounds of formula (I) mentioned in the preceding Examples, are prepared as follows: 250 g pulverized active ingredient is suspended in 2 liter Lauroglykol® (propylene glycol laurate, GattefosséS.A., Saint Priest, France) and ground in a wet pulverizer to produce a particle size of about 1 to 3 μm. 0.419 g portions of the mixture are then introduced into soft gelatin capsules using a capsule-filling machine.

The invention claimed is:

1. A compound of formula (I)

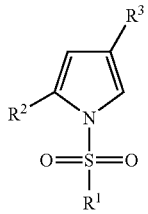

wherein

R$^1$ represents C$_{5-10}$ aryl, C$_{5-10}$ aryl-C$_{1-4}$ alkyl, C$_{5-10}$ aryl-C$_{2-4}$ alkenyl or 5 or 6-membered heteroaryl containing 1, 2, 3, or 4 heteroatoms selected from at least one of nitrogen, sulfur, and oxygen, wherein the aryl and the heteroaryl may be substituted by one to five substituents independently selected from C$_{1-4}$ alkyl, halo-C$_{1-4}$ alkyl, C$_{1-4}$ alkoxy, di C$_{1-7}$ alkylamino, halogen, and nitro;

and wherein two adjacent substituents together with atoms of the aryl or the heteroaryl may form a 5 membered heterocyclic ring containing at least one oxygen atom;

R$^2$ is C$_{5-10}$ aryl or 5 or 6-membered heteroaryl containing 1, 2, 3, or 4 heteroatoms selected from at least one of nitrogen, sulfur, and oxygen, wherein the aryl or the heteroaryl may be substituted by one to five substituents independently selected from C$_{1-4}$ alkyl, C$_{1-4}$ alkoxy, and halogen;

and wherein two adjacent substituents together with atoms of the aryl or the heteroaryl may form a 5 membered heterocyclic ring containing two oxygen atoms;

R$^3$ represents a group CH$_2$NR$^6$R$^7$;

R$^6$ represents hydrogen, C$_{1-7}$ alkyl, phenyl-C$_{1-4}$ alkyl optionally substituted by C$_{1-4}$ alkoxy, or amino-C$_{1-7}$ alkyl, wherein a nitrogen of the amino-C$_{1-7}$ alkyl can be substituted by up to two substituents selected from C$_{1-4}$ alkyl;

C$_{5-10}$ aryl substituted by one substituent selected from 5 or 6-membered heteroaryl containing 1, 2, 3 or 4 heteroatoms selected from at least one of nitrogen, sulfur, and oxygen, heterocyclyl containing 4-10 atoms compromising 1, 2, or 3 heteroatoms selected from at least one of nitrogen, sulfur, and oxygen, and a sulfamoyl group SO$_2$NR$^4$R$^5$, wherein said substituent on the aryl may be directly linked or linked via a spacer selected from C$_{1-4}$ alkylidene; and optionally one or two further substituents selected from C$_{1-4}$ alkyl;

C$_{5-10}$ aryl substituted by cyano; or 5 or 6-membered heteroaryl containing 1, 2, 3 or 4 heteroatoms selected from at least one of nitrogen, sulfur, and oxygen;

R$^4$ represents hydrogen;

R$^5$ represents hydrogen; and

R$^7$ represents hydrogen, C$_{1-4}$ alkyl, or C$_{1-4}$ alkylcarbonyl;

or salts thereof.

2. A compound of formula (I) according to claim 1, wherein

R$^1$ represents C$_{5-10}$ aryl or 5 or 6-membered heteroaryl containing 1, 2, 3 or 4 heteroatoms selected from at least one of nitrogen, sulfur, and oxygen, wherein the aryl and the heteroaryl may be substituted by one to five substituents independently selected from C$_{1-4}$ alkyl, halo-C$_{1-4}$ alkyl, C$_{1-4}$ alkoxy, di C$_{1-7}$ alkylamino, halogen, and nitro;

R$^2$ is C$_{5-10}$ aryl or 5 or 6-membered heteroaryl containing 1, 2, 3 or 4 heteroatoms selected from at least one of nitrogen, sulfur, and oxygen, wherein the aryl or the heteroaryl may be substituted by one to five substituents independently selected from C$_{1-4}$ alkyl, C$_{1-4}$ alkoxy, and halogen;

and wherein two adjacent substituents together with atoms of the aryl or the heteroaryl may form a 5membered heterocyclic ring containing two oxygen atoms;

R$^3$ represents a group CH$_2$NR$^6$R$^7$;

R$^6$ represents hydrogen, C$_{1-7}$ alkyl, phenyl-C$_{1-4}$ alkyl optionally substituted by C$_{1-4}$ alkoxy, or amino-C$_{1-7}$ alkyl, wherein a nitrogen of the amino-C$_{1-7}$ alkyl can be substituted by up to two substituents selected from C$_{1-4}$ alkyl; or C$_{5-10}$ aryl substituted by one substituent selected from 5 or 6-membered heteroaryl containing 1, 2, 3 or 4 heteroatoms selected from at least one of nitrogen, sulfur, and oxygen, heterocyclyl containing 4-10 atoms comprising 1, 2, or 3 heteroatoms selected from at least one of nitrogen, sulfur, and oxygen, and a sulfamoyl group SO$_2$NR$^4$R$^5$, wherein said substituent on the aryl may be directly linked or linked via a spacer selected from C$_{1-4}$ alkylidene; and optionally one or two further substituents selected from C$_{1-4}$ alkyl, or C$_{5-10}$ aryl substituted by cyano; or 5 or 6-membered heteroaryl containing 1, 2, 3 or 4 heteroatoms selected from at least one of nitrogen, sulfur, and oxygen;

R$^4$ represents hydrogen;

R$^5$ represents hydrogen; and

R$^7$ represents hydrogen, C$_{1-4}$ alkyl, or C$_{1-4}$ alkylcarbonyl;

or salts thereof.

3. A compound of formula (I) according to claim 1, wherein

R$^1$ represents C$_{5-10}$ aryl or 5 or 6-membered heteroaryl containing 1, 2, 3 or 4 heteroatoms selected from at least one of nitrogen, sulfur, and oxygen, wherein the aryl and the heteroaryl may be substituted by one to five substituents independently selected from C$_{1-4}$ alkyl, halo-C$_{1-4}$ alkyl, C$_{1-4}$ alkoxy, di C$_{1-7}$ alkylamino, and halogen;

R$^2$ is C$_{5-10}$ aryl or 5 or 6-membered heteroaryl containing 1, 2, 3 or 4 heteroatoms selected from at least one of nitrogen, sulfur, and oxygen, wherein the aryl or the heteroaryl may be substituted by one to five substituents independently selected from C$_{1-4}$ alkyl, C$_{1-4}$ alkoxy, and halogen;

and wherein two adjacent substituents together with atoms of the aryl or the heteroaryl may form a 5 membered heterocyclic ring containing two oxygen atoms;

R$^3$ represents a group CH$_2$NR$^6$R$^7$;

R$^6$ represents hydrogen, C$_{1-7}$ alkyl, phenyl-C$_{1-4}$ alkyl optionally substituted by C$_{1-4}$ alkoxy, or amino-C$_{1-7}$ alkyl, wherein a nitrogen of the amino-C$_{1-7}$ alkyl can be substituted by up to two substituents selected from C$_{1-4}$ alkyl; or phenyl substituted by one substituent selected from 5 or 6-membered heteroaryl containing 1, 2, 3 or 4 heteroatoms selected from at least one of nitrogen, sulfur, and oxygen, heterocyclyl containing 4-10 atoms comprising 1, 2 or 3 heteroatoms selected from at least one of nitrogen, sulfur, and oxygen, and a sulfamoyl group SO$_2$NR$^4$R$^5$, wherein said substituent on the phenyl may be directly linked or linked via a spacer selected from $C_{1-4}$ alkylidene; and optionally one or two further substituents selected from $C_{1-4}$ alkyl; or phenyl substituted by cyano; or pyridyl;

$R^4$ represents hydrogen;

$R^5$ represents hydrogen; and $R^7$ represents hydrogen, $C_{1-4}$ alkyl, or $C_{1-4}$ alkylcarbonyl;

or salts thereof.

4. A compound of formula (I) according to claim 1, wherein $R^1$ represents $C_{5-10}$ aryl or 5 or 6-membered heteroaryl containing 1, 2, 3 or 4 heteroatoms selected from at least one of nitrogen, sulfur, and oxygen, wherein the aryl and the heteroaryl may be substituted by one to five substituents independently selected from $C_{1-4}$ alkyl, halo-$C_{1-4}$ alkyl, $C_{1-4}$ alkoxy, di $C_{1-7}$ alkylamino, and halogen;

$R^2$ is $C_{5-10}$ aryl or 5 or 6-membered heteroaryl containing 1, 2, 3 or 4 heteroatoms selected from at least one of nitrogen, sulfur, and oxygen, wherein the aryl or the heteroaryl may be substituted by one to five substituents independently selected from $C_{1-4}$ alkyl, and halogen;

and wherein two adjacent substituents together with atoms of the aryl or the heteroaryl may form a 5 membered heterocyclic ring containing two oxygen atoms;

$R^3$ represents a group $CH_2NR^6R^7$;

$R^6$ represents hydrogen, $C_{1-4}$ alkyl, or amino-$C_{1-7}$ alkyl, wherein a nitrogen of the amino-$C_{1-7}$ alkyl can be substituted by up to two substituents selected from $C_{1-4}$ alkyl; or phenyl substituted by one substituent selected from 5 or 6-membered heteroaryl containing 1, 2, 3 or 4 heteroatoms selected from at least one of nitrogen, sulfur, and oxygen, heterocyclyl containing 4-10 atoms comprising 1, 2 or 3 heteroatoms selected from at least one of nitrogen, sulfur, and oxygen, and a sulfamoyl group $SO_2NR^4R^5$, wherein said substituent on the phenyl may be directly linked or linked via a spacer selected from $C_{1-4}$ alkylidene; and optionally one or two further substituents selected from $C_{1-4}$ alkyl; or phenyl substituted by cyano; or pyridyl;

$R^4$ represents hydrogen;

$R^5$ represents hydrogen; and $R^7$ represents hydrogen, $C_{1-4}$ alkyl;

or salts thereof.

5. A compound of formula (I) according to claim 1, wherein $R^1$ represents phenyl substituted by up to two substituents independently selected from $C_{1-4}$ alkyl, $C_{1-4}$ alkoxy, and halogen;

$R^2$ is $C_{5-10}$ aryl optionally substituted by one to three substituents independently selected from $C_{1-4}$ alkyl, and halogen;

and wherein two adjacent substituents together with atoms of the aryl may form a 5 membered heterocyclic ring containing two oxygen atoms;

$R^3$ represents a group $CH_2NR^6R^7$;

$R^6$ represents phenyl substituted by one substituent selected from 5 or 6-membered heteroaryl containing 1, 2, 3 or 4 heteroatoms selected from at least one of nitrogen, sulfur, and oxygen heterocyclyl containing 4-10 atoms comprising 1, 2 or 3 heteroatoms selected from at least one of nitrogen, sulfur, and oxygen, and a sulfamoyl group $SO_2NR^4R^5$, wherein said substituent on the phenyl may be directly linked or linked via a spacer selected from $C_{1-4}$ alkylidene; or pyridyl;

$R^4$ represents hydrogen;

$R^5$ represents hydrogen; and $R^7$ represents hydrogen or $C_{1-4}$ alkyl;

or salts thereof.

6. A compound of formula (I) according to claim 1 selected from the group consisting of (p-1-imidazolylphenyl)-(1-[p-toluenesulfonyl]-2-[3,4,5-trimethoxyphenyl]-4-pyrrolylmethyl)-amine;

(p-1,2,4-triazolylphenyl)-(1-[p-toluenesulfonyl]-2-[3,4,5-trimethoxyphenyl]-4-pyrrolylmethyl)-amine;

(p-morpholinophenyl)-(1-[p-toluenesulfonyl]-2-[3,4,5-trimethoxyphenyl]-4-pyrrolylmethyl)-amine; and (p-morpholinophenyl)-(1-[p-toluenesulfonyl]-2-[3,4,5-trimethoxyphenyl]-4-pyrrolylmethyl)-amine.

7. A compound of formula (I) according to claim 1 selected from the group consisting of (p-1-imidazolylphenyl)-(1-[p-toluenesulfonyl]-2-[3,4,5-trimethoxyphenyl]-4-pyrrolylmethyl)-amine; and (p-morpholinophenyl)-(1[p-methoxyphenyl]-2-[3,4,5-trimethoxyphenyl]-4-pyrrolylmethyl)-amine.

8. The compound of formula (I) according to claim 1 which is (p-1-imidazolylphenyl)-(1-[p-toluenesulfonyl]-2-[3,4,5-trimethoxyphenyl]-4-pyrrolylmethyl)-amine.

9. A pharmaceutical composition comprising a compound of formula (I) according to claim 1 and a pharmaceutically acceptable carrier.

* * * * *

UNITED STATES PATENT AND TRADEMARK OFFICE
CERTIFICATE OF CORRECTION

PATENT NO. : 7,612,064 B2
APPLICATION NO. : 10/557664
DATED : November 3, 2009
INVENTOR(S) : Eberle et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 5 days.

Signed and Sealed this

Nineteenth Day of October, 2010

David J. Kappos
*Director of the United States Patent and Trademark Office*

UNITED STATES PATENT AND TRADEMARK OFFICE
CERTIFICATE OF CORRECTION

PATENT NO.        : 7,612,064 B2
APPLICATION NO.   : 10/557664
DATED             : November 3, 2009
INVENTOR(S)       : Martin Eberle et al.

It is certified that error appears in the above-identified patent and that said Letters Patent is hereby corrected as shown below:

Title page, item (75) Inventors: "Frank Lach" should be --Franck Lach--.
Title page, item (75) Inventors: "Allessandro Strebel" should be --Alessandro Strebel--.
Column 1, line 9: "a diseases" should be --diseases--.
Column 2, line 21, "a compounds" should be --compounds--.
Column 9, line 65, "Grave" should be --Grave's--.
Column 36, line 45, "$^1$H NMR" should read --$^1$H-NMR--.
Column 50, lines 33-34, delete formula 73 and replace with -- 73 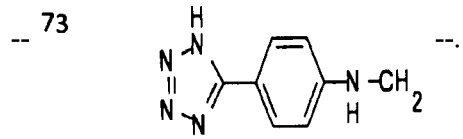 --.

Column 52, line 31, "br.s, $_1$H" should be --br.s, 1H--.
Column 54, line 53, "4bromo" should be --4-bromo--.
Column 55, line 2, "4Bromo" should be --4-Bromo--.
Column 69, line 42, "concentrations" should be --concentration--.
Column 70, line 32, "After" should be --after--.
Column 70, line 63, "GattefosséS.A." should be --Gattefossé S.A.--.
Column 72, line 11, "5membered" should be --5 membered--.
Column 72, line 28, "alkyl," should be --alkyl;--.

Signed and Sealed this

Thirtieth Day of November, 2010

David J. Kappos
*Director of the United States Patent and Trademark Office*